US007696352B2

(12) United States Patent
Zhu et al.

(10) Patent No.: US 7,696,352 B2
(45) Date of Patent: *Apr. 13, 2010

(54) FACTOR XA INHIBITORS

(75) Inventors: Bing-Yan Zhu, Palo Alto, CA (US); Shawn M. Bauer, Pacifica, CA (US); Zhaozhong J. Jia, San Mateo, CA (US); Yonghong Song, Foster City, CA (US); Gary D. Probst, San Francisco, CA (US); Yanchen Zhang, Union City, CA (US); Robert M. Scarborough, Half Moon Bay, CA (US); Carroll Anna Crew Scarborough, legal representative, Half Moon Bay, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 293 days.

This patent is subject to a terminal disclaimer.

(21) Appl. No.: 11/620,615

(22) Filed: Jan. 5, 2007

(65) Prior Publication Data
US 2007/0185092 A1 Aug. 9, 2007

Related U.S. Application Data

(63) Continuation-in-part of application No. 11/158,274, filed on Jun. 20, 2005, now Pat. No. 7,521,470.

(60) Provisional application No. 60/580,899, filed on Jun. 18, 2004.

(51) Int. Cl.
C07D 409/14 (2006.01)
C07D 401/14 (2006.01)
C07D 409/12 (2006.01)
A61K 31/4436 (2006.01)

(52) U.S. Cl. ............... 546/268.4; 546/272.4; 548/255; 548/266.6; 514/383; 514/359; 514/342

(58) Field of Classification Search ............ 546/279.9, 546/272.4, 268.4; 548/255, 266.6; 514/342, 514/383, 359
See application file for complete search history.

(56) References Cited

U.S. PATENT DOCUMENTS

| 6,423,713 | B1 | 7/2002 | Anantanarayan et al. |
| 7,157,456 | B2 | 1/2007 | Straub et al. |
| 2005/0171358 | A1 | 8/2005 | Shimozono et al. |
| 2006/0100193 | A1 | 5/2006 | Zhu et al. |
| 2007/0066615 | A1 | 3/2007 | Gerdes et al. |

FOREIGN PATENT DOCUMENTS

| CA | 2453846 A1 | 1/2003 |
| DE | 10322469 A1 | 12/2004 |
| WO | WO 99/28317 | 6/1999 |
| WO | WO 01/21160 A2 | 3/2001 |
| WO | WO 01/47919 A1 | 7/2001 |
| WO | WO 01/91558 A1 | 12/2001 |
| WO | WO 02/00651 A2 | 1/2002 |
| WO | WO 03/008395 A1 | 1/2003 |
| WO | WO 03/059894 | 7/2003 |
| WO | WO 2004/101531 | 11/2004 |
| WO | WO 2004/101557 A1 | 11/2004 |
| WO | WO 2004/106329 | 12/2004 |
| WO | WO 2005/032468 A2 | 4/2005 |
| WO | WO 2005/035528 | 4/2005 |
| WO | WO 2005/082892 | 9/2005 |
| WO | WO 2006/002099 | 1/2006 |
| WO | WO 2007/025940 | 3/2007 |
| WO | WO 2007/131179 | 11/2007 |

OTHER PUBLICATIONS

Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Smallheer. et. al. "Sulfonamidolactam inhibitors of coagulation factor Xa" Bioorganic & Medicinal Chemistry Letters 2008, 18, 2428-2433.*
Qiao et. al. "SAR and X-ray structures of enantiopure 1,2-cis-(1R,2S)-cyclopentyldiamine and cyclohexyldiamine derivatives as inhibitors of coagulation Factor Xa" Bioorganic & Medicinal Chemistry Letters 2007, 17, 4419-4427.*
Roehrig et. al. "Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor" Journal of Medicinal Chemistry 2005, 48, 5900-5908.*
Shi et. al. "Cyanoguanidine-based lactam derivatives as a novel class of orally bioavailable factor Xa inhibitors" Bioorganic & Medicinal Chemistry Letters 19 (2009) 4034-4041.*
Song et. al. "Substituted Acrylamides as Factor Xa Inhibitors: Improving Bioavailability by P1 Modification" Bioorganic & Medicinal Chemistry Letters 12 (2002) 2043-2046.*
In the Pipeline, online, accessed Jun. 16, 2008, "http://pipeline.corante.com/archives/2006/01/24/the_examiner_finally_snaps.php".*
International Search Report, PCT/US2008/050244, dated Apr. 1, 2008.
Roehrig S et al., "Discovery of the Novel Antithrombotic Agent 5-Chloro-N-(((5S)-2-oxo-3[4-(3-oxomorpholin-4-yl)phenyl]-1,3-oxazolidin-5-yl)methyl)thiophene 2-carboxamide (BAY 59-7939): An Oral, Direct Factor Xa Inhibitor", *J. Med. Chem.* 2005, 48.
Ostrovsky, et al., "Analyses of Activity for Factory Xa Inhibitors Based on Monte Carlo Simulations", *J. Med. Chem.* 2003, 46, 5691-5699.

* cited by examiner

*Primary Examiner*—Rita J Desai
*Assistant Examiner*—David K O'Dell
(74) *Attorney, Agent, or Firm*—Swiss Tanner, P.C.

(57) ABSTRACT

The present invention is directed to compounds represented by Formula (I) or a pharmaceutically acceptable salt, ester, or prodrug thereof which are inhibitors of Factor Xa. The present invention is also directed to and intermediates used in making such compounds, pharmaceutical compositions containing such compounds, methods to prevent or treat a number of conditions characterized by undesired thrombosis and methods of inhibiting the coagulation of a blood sample.

16 Claims, No Drawings

FACTOR XA INHIBITORS

CROSS-REFERENCES TO RELATED APPLICATIONS

This application is a continuation-in-part application of U.S. patent application Ser. No. 11/158,274, filed Jun. 20, 2005, which claims the benefit of U.S. Provisional Application No. 60/580,899, filed Jun. 18, 2004, which applications are incorporated herein by reference in their entireties.

BACKGROUND OF THE INVENTION

1. Field of the Invention

This invention is directed to novel compounds which act as inhibitors of Factor Xa. This invention is also directed to pharmaceutical compositions containing the compounds and methods of using the compounds or compositions to treat a condition characterized by undesired thrombosis. The invention is also directed to methods of making the compounds described herein.

2. State of the Art

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in restoring hemostasis and in thrombotic diseases, certain components of the coagulation cascade are primarily responsible for the amplification and acceleration of the processes involved in platelet aggregation and fibrin deposition which are major events in thrombosis and hemostasis.

Clot formation involves the conversion of fibrinogen to fibrin which polymerizes into a network to restore hemostasis after injury. A similar process results in occluded blood vessels in thrombotic diseases. The conversion of fibrinogen to fibrin is catalyzed by thrombin, the end product of a series of reactions in the blood coagulation cascade. Thrombin is also a key player in activating platelets, thereby contributing to thrombosis under conditions of both arterial and venous blood flow. For these reasons, it has been postulated that efficient regulation of thrombin can lead to efficient regulation of thrombosis. Several classes of currently used anticoagulants directly or indirectly affect thrombin (i.e. unfractionated heparins, low-molecular weight heparins, heparin-like compounds, pentasaccharide and warfarin). Direct or indirect inhibition of thrombin activity has also been the focus of a variety of anticoagulants in clinical development (reviewed by Eriksson and Quinlan, *Drugs* 11: 1411-1429, 2006).

Prothrombin, the precursor for thrombin, is converted to the active enzyme by factor Xa. Localized activation of tissue factor/factor VIa mediated factor Xa generation is amplified by the factor IXa/factor VIIIa complex and leads to prothrombinase assembly on activated platelets. Factor Xa, as a part of the prothrombinase complex, is the sole enzyme responsible for sustained thrombin formation in the vasculature. Factor Xa is a serine protease, the activated form of its precursor Factor X, and a member of the calcium ion binding, gamma carboxyglutamic acid (GLA)-containing, vitamin K dependent, blood coagulation factors. Unlike thrombin, which acts on a variety of protein substrates including fibrinogen and the PAR receptors (Protease activated receptors, Coughlin, *J Thrombosis Haemostasis* 3: 1800-1814, 2005), factor Xa appears to have a single physiologic substrate, namely prothrombin. Since one molecule of factor Xa may be able to generate greater than 1000 molecules of thrombin (Mann, et al., *J. Thrombosis. Haemostasis* 1: 1504-1514, 2003), direct inhibition of factor Xa as a way of indirectly inhibiting the formation of thrombin is considered an efficient anticoagulant strategy. This assertion is based on the key role of prothrombinase in thrombin synthesis and on the fact that inhibition of prothrombinase will have a pronounced effect on the overall platelet aggregation and clotting pathways. Activated proteases such as factor VIIa, factor IXa or factor Xa have poor proteolytic activity on their own. However, their assembly into cofactor-dependent, membrane-bound complexes significantly enhances their catalytic efficiencies. This effect is most dramatic for factor Xa, where the efficiency is increased by a factor of $10^5$ (Mann, et al., *Blood* 76(1): 1-16, 1990). Due to the higher concentration of the zymogens present in blood (1.4 micromolar prothrombin versus 150 nanomolar factor X) and the kinetics of activation, a smaller amount of factor Xa than thrombin needs to be inhibited to achieve an anticoagulant effect. Indirect proof of the hypothesis of superiority of factor Xa as a therapeutic target compared to thrombin can also be found in clinical trials for the prevention of deep vein thrombosis. Fondaparinux, an anti-thrombin III dependent factor Xa inhibitor, was proven to be superior to enoxaparin (a low molecular weight heparin that inhibits both thrombin and factor Xa) in four trials of orthopedic surgery (Turpie, et al., *Archives Internal Medicine* 162 (16): 1833-1840, 2002). Therefore, it has been suggested that compounds which selectively inhibit factor Xa may be useful as in vitro diagnostic agents, or for therapeutic administration in certain thrombotic disorders, see e.g., WO 94/13693.

Several Factor Xa inhibitors have been reported as polypeptides derived from hematophagous organisms, as well as compounds which are not large polypeptide-type inhibitors. Additional Factor Xa inhibitors include small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naphthyl group via a straight or branched chain alkylene, —C(=O) or —S(=O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group. Additional reported Factor Xa inhibitors include those having a structure comprising a phenyl-amidino, phenyl and halo-phenyl connected via amide linkages (U.S. Pat. No. 6,844,367 B1). Other Factor Xa inhibitors by the same group have replaced the halo-phenyl with a halo-pyridyl (see U.S. Pat. Nos. 6,376,515 B2 and 6,835,739 B2).

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

BRIEF SUMMARY OF THE INVENTION

The present invention provides in one aspect, compounds having the formula:

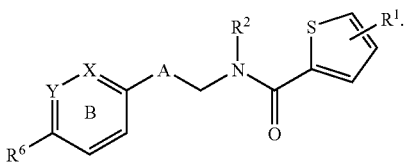

In formula (I), the symbol $R^1$ is halogen, $C_{1-8}$ alkyl, $C_{2-8}$ alkenyl, and $C_{2-8}$ alkynyl.

The symbol $R^2$ is hydrogen or $C_{1-4}$ alkyl.

The symbol A is selected from the group consisting of:

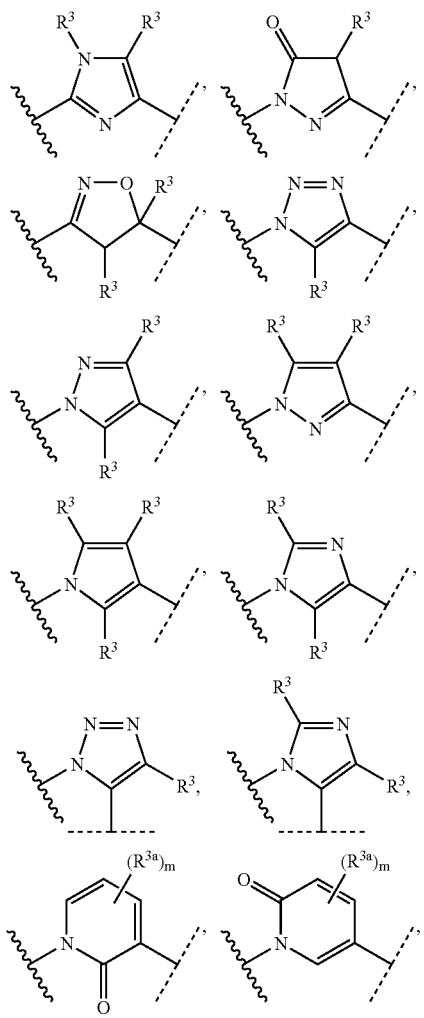

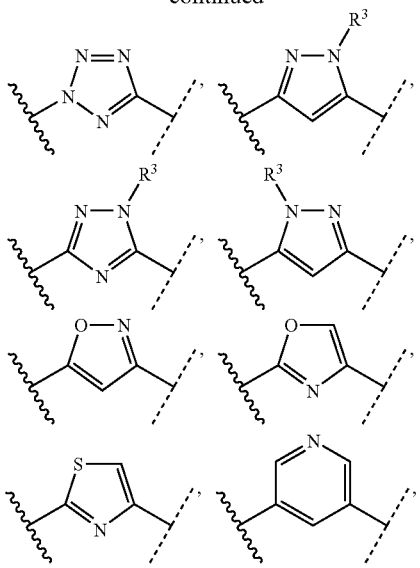

wherein the wavy line indicates the point of attachment to ring B and the dashed line indicates the point of attachment to the rest of the molecule;

The symbol $R^3$ is independently hydrogen or $R^{3a}$, wherein $R^{3a}$ is independently selected from the group consisting of halogen, $C_{1-8}$ alkyl, $C_{2-8}$ alkenyl, and $C_{2-8}$ alkynyl.

The subscript m is 0, 1, 2, or 3.

The symbol X is C—$R^4$ or N.

The symbol Y is C—$R^5$ or N provided that X and Y are not both N.

In some embodiments, X and Y are C and are fused to form a 6-membered aryl, heteroaryl, or heterocyclic ring.

The symbol $R^4$ is selected from the group consisting of hydrogen, halogen, and

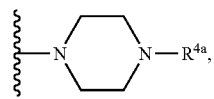

wherein $R^{4a}$ is hydrogen or $C_{1-8}$ alkyl.

The symbol $R^5$ is selected from the group consisting of hydrogen, halogen, and $C_{1-8}$ alkoxy.

The symbol $R^6$ is selected from the group consisting of —$R^{6a}$, —$NR^{7a}R^{7b}$, —$NR^{7a}C(O)R^{7c}$, —$NR^{7a}C(O)OR^{7c}$, —$CONR^{8a}R^{8b}$, —$OR^{7c}$, —$SR^{7c}$, —$C(=NR^{7a})NR^{8a}R^{8b}$, —$S(O)_2NR^{8a}R^{8b}$, and —$S(O)_2R^{7c}$.

In some embodiments, $R^5$ and $R^6$ join together with the atoms bound thereto to form a 6-membered aryl, heteroaryl, or heterocyclic ring fused to ring B.

The symbol $R^{6a}$ is selected from the group consisting of

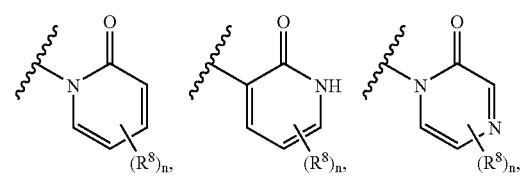

-continued

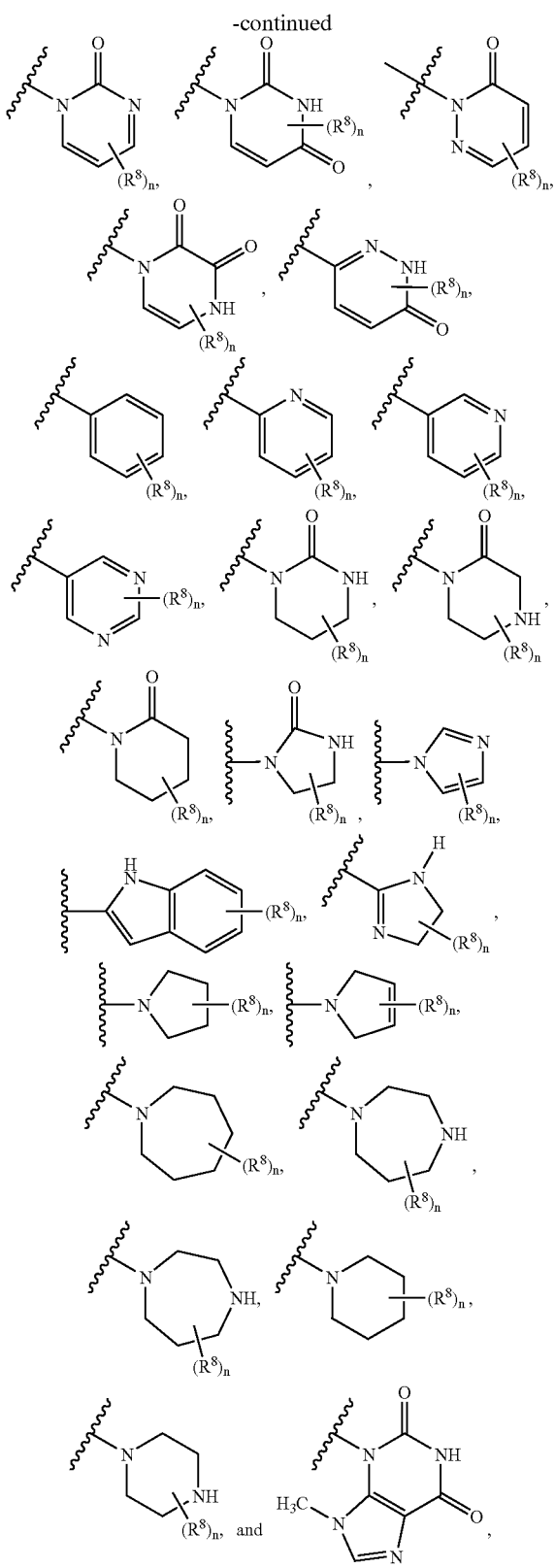

wherein $R^8$ can be at any position suitable for a substituent, and if $R^8$ is attached to a nitrogen atom, then it replaces the hydrogen atom attached thereto.

The symbol $R^{7a}$ and $R^{7b}$ are independently selected from the group consisting of hydrogen, $C_{1-8}$ alkyl, and $C_{1-8}$ alkyl substituted with one to three $R^9$.

The symbol $R^{7c}$ is selected from the group consisting of aryl, heteroaryl, $C_{1-8}$ alkyl, and $C_{1-8}$ alkyl substituted with one to three $R^9$.

The symbol $R^8$ is independently selected from the group consisting of nitro, hydroxy, $-CO_2H$, $-C(O)R^{8c}$, $-C(O)NR^{8a}R^{8b}$, $NR^{8a}R^{8b}$, $-SO_2NR^{8a}R^{8b}$, halogen, $C_{1-8}$ alkyl, and $C_{1-8}$ alkoxy wherein said $C_{1-8}$ alkyl and $C_{1-8}$ alkoxy are optionally substituted with one to three $R^9$.

The symbol $R^{8a}$ and $R^{8b}$ are independently selected from the group consisting of hydrogen, $C_{1-8}$ alkyl, and $C_{1-8}$ alkyl substituted with one to three $R^9$, or $R^{8a}$ and $R^{8b}$ join together along with the atom bound thereto to form a 5 to 7 membered heterocyclic ring optionally substituted with one to three $R^9$ and optionally having one additional ring heteroatom selected from N, O, or S.

The symbol $R^{8c}$ is selected from the group consisting of $C_{1-8}$ alkyl and $C_{1-8}$ alkyl substituted with one to three $R^9$.

The symbol $R^9$ is independently selected from the group consisting of halogen, heterocyclic, heteroaryl, $-OH$, $-R^{10}$, $-OR^{10}$, $-SR^{10}$, $-S(O)R^{10}$, $-S(O)_2R^{10}$, $-SO_2NH_2$, $-C(O)NH_2$, $-C(O)R^{10}$, $-C(NH)R^{10}$, $-NHC(O)R^{10}$, $-NHC(NH)R^{10}$, $-NHC(O)NH_2$, $-CO_2H$, $-NH_2$, $-NHR^{10}$, $-N(R^{10})_2$, and $-N(R^{10})_3^+$.

The symbol $R^{10}$ is independently $C_{1-6}$ alkyl.

The subscript n is 0, 1, 2, or 3.

Formula (I) is with the proviso that when X is $C-R^4$, Y is $C-R^5$, $R^6$ is $R^{6a}$, and A is

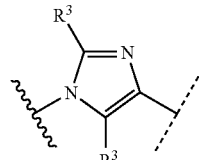

then $R^{6a}$ is bound to ring B through a carbon atom.

The present invention also contemplates pharmaceutically acceptable salts, esters, and prodrugs of formula (I).

The present invention further provides chemical intermediates, pharmaceutical compositions and methods for preventing or treating a condition in a mammal characterized by undesired thrombosis comprising the step of administering to said mammal a therapeutically effective amount of a compound of the present invention. Such conditions include but are not limited to acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

The present invention further provides methods for inhibiting the coagulation of a blood sample comprising contacting said sample with a compound of the present invention.

DETAILED DESCRIPTION OF THE INVENTION

Abbreviations and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more, preferably 1 to 3, double bonds. Similarly, the term "alkynyl" refers to an unsaturated alkyl group having one or more, preferably 1 to 3, triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "cycloalkyl" refers to hydrocarbon rings having the indicated number of ring atoms (e.g., $C_{3-6}$ cycloalkyl) and being fully saturated between ring vertices. The term "cycloalkenyl" refers to a cycloalkyl group that has at least one point of alkenyl unsaturation between the ring vertices. The term "cycloalkynyl" refers to a cycloalkyl group that has at least one point of alkynyl unsaturation between the ring vertices. When "cycloalkyl" is used in combination with "alkyl", as in $C_{3-5}$ cycloalkyl-alkyl, the cycloalkyl portion is meant to have the stated number of carbon atoms (e.g., from three to five carbon atoms), while the alkyl portion is an alkylene moiety having from one to three carbon atoms (e.g., $—CH_2—$, $—CH_2CH_2—$ or $—CH_2CH_2CH_2—$).

The term "alkylene" by itself or as part of another substituent means a divalent radical derived from an alkane, as exemplified by $—CH_2CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The terms "alkoxy," "alkylamino," and "alkylthio" (or thioalkoxy) are used in their conventional sense, and refer to those alkyl groups attached to the remainder of the molecule via an oxygen atom (—O-alkyl), an amino group, or a sulfur atom (—S-alkyl), respectively. Additionally, for dialkylamino groups (typically provided as —NR$^a$R$^b$ or a variant thereof, where R$^a$ and R$^b$ are independently alkyl or substituted alkyl), the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl up to the maximum number of halogens permitted. For example, the term "$C_{1-4}$ haloalkyl" is mean to include trifluoromethyl, 2,2,2-trifluoroethyl, 4-chlorobutyl, 3-bromopropyl, and the like.

The term "hydroxy" or "hydroxyl" refers to the group —OH.

The term "aryl" means, unless otherwise stated, a polyunsaturated, aromatic, hydrocarbon group containing from 6 to 14 carbon atoms, which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. If not specifically stated, substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl or heteroaryl group is attached to an alkyl group (e.g., benzyl, phenethyl, pyridylmethyl and the like).

The term "heterocycle" or "heterocyclyl" or "hetreocyclic" refers to a saturated or unsaturated non-aromatic cyclic group containing at least one sulfur, nitrogen or oxygen heteroatom. Each heterocycle can be attached at any available ring carbon or heteroatom. Each heterocycle may have one or more rings. When multiple rings are present, they can be fused together or linked covalently. Each heterocycle must contain at least one heteroatom (typically 1 to 5 heteroatoms) selected from nitrogen, oxygen or sulfur. Preferably, these groups contain 1-10 carbon atoms, 0-5 nitrogen atoms, 0-2 sulfur atoms and 0-2 oxygen atoms, wherein the nitrogen and sulfur atoms are optionally oxidized, and the nitrogen atom(s) are optionally quaternized. More preferably, these groups contain 0-3 nitrogen atoms, 0-1 sulfur atoms and 0-1 oxygen atoms.

Non-limiting examples of heterocycle and heteroaryl groups include pyridine, pyridimidine, pyrazine, morpholin-3-one, piperazine-2-one, pyridine-2-one, piperidine, morpholine, piperazine, isoxazole, isothiazole, pyrazole, imidazole, oxazole, thiazole, isoxazoline, pyrazoline, imidazoline, 1,2,3-triazole, 1,2,4-triazole, 1,3,4-oxadiazole, 1,3,4-thiadiazole, 1,2,4-oxadiazole, 1,2,4-thiadiazole, pyrazol-5-one, pyrrolidine-2,5-dione, imidazolidine-2,4-dione, pyrrolidine, pyrrole, furan, thiophene, and the like.

The term "heterocycloalkyl" refers to the group alkyleneheterocycle, wherein both heterocycle and alkylene are as defined above.

The above terms (e.g., "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below.

Substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)

R', —S(O)₂R', —S(O)₂NR'R", —NR'S(O)₂R", —N₃, perfluoro(C₁-C₄)alkoxy, and perfluoro(C₁-C₄)alkyl, in a number ranging from zero to the total number of open valences on the aromatic ring system; and where R', R" and R''' are independently selected from hydrogen, C₁₋₈alkyl, C₃₋₆cycloalkyl, C₂₋₈alkenyl, C₂₋₈alkynyl, unsubstituted aryl and heteroaryl, (unsubstituted aryl)-C₁₋₄alkyl, and unsubstituted aryloxy-C₁₋₄alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH₂)_q—U—, wherein T and U are independently —NH—, —O—, —CH₂— or a single bond, and q is an integer of from 0 to 2. Alternatively, two of the substituents on adjacent atoms of the aryl or heteroaryl ring may optionally be replaced with a substituent of the formula -A-(CH₂)_r—B—, wherein A and B are independently —CH₂—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)_s—X—(CH₂)_t—, where s and t are independently integers of from 0 to 3, and X is —O—, —NR'—, —S—, —S(O)—, —S(O)₂—, or —S(O)₂NR'—. The substituent R' in —NR'— and —S(O)₂NR'— is selected from hydrogen or unsubstituted C₁₋₆alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium (³H), iodine-125 (¹²⁵I) or carbon-14 (¹⁴C). All isotopic variations of the compounds of the present invention, whether radioactive or not, are intended to be encompassed within the scope of the present invention.

Accordingly, in one embodiment provided is a compound having Formula (I) or a pharmaceutically acceptable salt, ester, or prodrug thereof:

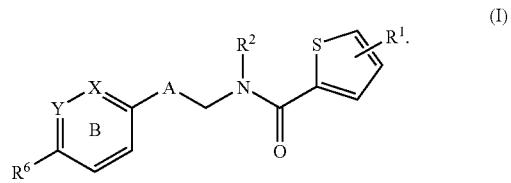

In Formula (I), the symbol R¹ is halogen, C₁₋₈ alkyl, C₂₋₈ alkenyl, and C₂₋₈ alkynyl.

The symbol R² is hydrogen or C₁₋₄ alkyl.

The symbol A is selected from the group consisting of:

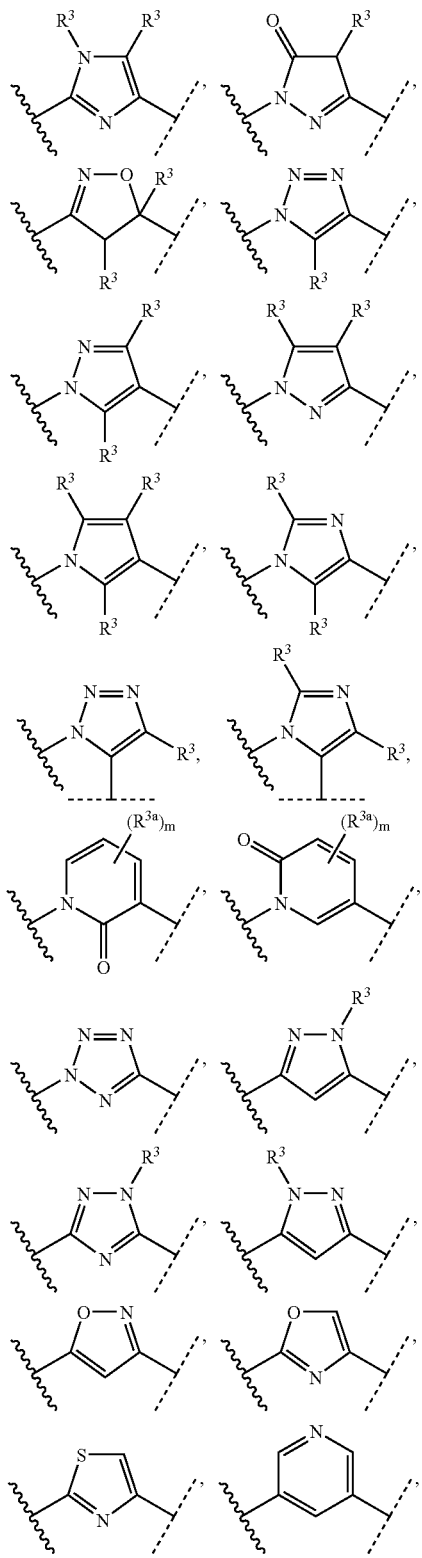

wherein the wavy line indicates the point of attachment to ring B and the dashed line indicates the point of attachment to the rest of the molecule.

The symbol $R^3$ is independently hydrogen or $R^{3a}$, wherein $R^{3a}$ is independently selected from the group consisting of halogen, $C_{1-8}$ alkyl, $C_{2-8}$ alkenyl, and $C_{2-8}$ alkynyl.

The subscript m is 0, 1, 2, or 3.

The symbol X is C—$R^4$ or N.

The symbol Y is C—$R^5$ or N provided that X and Y are not both N. In some embodiments, X and Y are C and are fused to form a 6-membered aryl, heteroaryl, or heterocyclic ring.

The symbol $R^4$ is selected from the group consisting of hydrogen, halogen, and

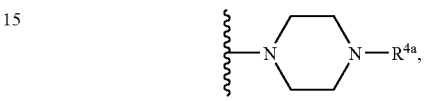

wherein $R^{4a}$ is hydrogen or $C_{1-8}$ alkyl.

The symbol $R^5$ is selected from the group consisting of hydrogen, halogen, and $C_{1-8}$ alkoxy; or $R^5$ and $R^6$ join together along with the atom bound thereto to form a 6-membered aryl, heteroaryl, or heterocyclic ring fused to ring B.

The symbol $R^6$ is selected from the group consisting of —$R^{6a}$, —$NR^{7a}R^{7b}$, —$NR^{7a}C(O)R^{7c}$, —$NR^{7a}C(O)OR^{7c}$, —$CONR^{8a}R^{8b}$, —$OR^{7c}$, —$SR^{7c}$—$C(=NR^{7a})NR^{8a}R^{8b}$, —$S(O)_2NR^{8a}R^{8b}$, and —$S(O)_2R^{7c}$.

The symbol $R^{6a}$ is selected from the group consisting of

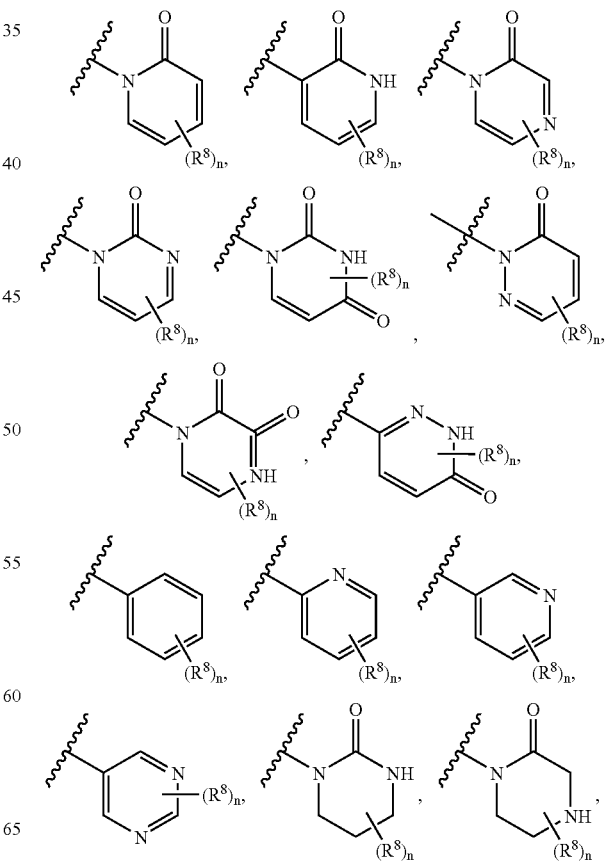

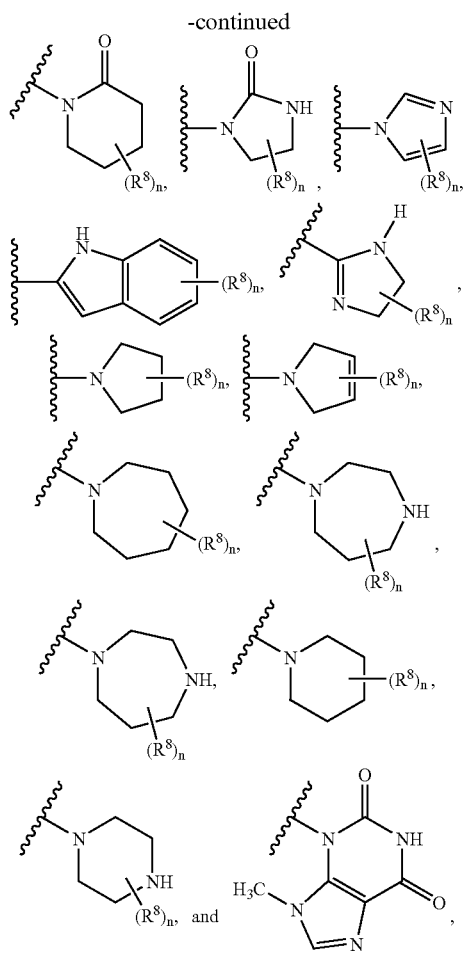

wherein R⁸ can be at any position suitable for a substituent, and if R⁸ is attached to a nitrogen atom, then it replaces the hydrogen atom attached thereto.

The symbol $R^{7a}$ and $R^{7b}$ are independently selected from the group consisting of hydrogen, $C_{1-8}$ alkyl, and $C_{1-8}$ alkyl substituted with one to three $R^9$.

The symbol $R^{7c}$ is selected from the group consisting of aryl, heteroaryl, $C_{1-8}$ alkyl, and $C_{1-8}$ alkyl substituted with one to three $R^9$.

The symbol $R^8$ is independently selected from the group consisting of nitro, hydroxy, —$CO_2H$, —$C(O)R^{8c}$, —$C(O)NR^{8a}R^{8b}$, $NR^{8a}R^{8b}$, —$SO_2NR^{8a}R^{8b}$, halogen, $C_{1-8}$ alkyl, and $C_{1-8}$ alkoxy wherein said $C_{1-8}$ alkyl and $C_{1-8}$ alkoxy are optionally substituted with one to three $R^9$.

The symbol $R^{8a}$ and $R^{8b}$ are independently selected from the group consisting of hydrogen, $C_{1-8}$ alkyl, and $C_{1-8}$ alkyl substituted with one to three $R^9$ or $R^{8a}$ and $R^{8b}$ together form a 5 to 7 membered heterocyclic ring optionally substituted with one to three $R^9$ and optionally having one additional ring heteroatom selected from N, O, or S.

The symbol $R^{8c}$ is selected from the group consisting of $C_{1-8}$ alkyl and $C_{1-8}$ alkyl substituted with one to three $R^9$.

The symbol $R^9$ is independently selected from the group consisting of halogen, heterocyclic, heteroaryl, —OH, —$R^{10}$, —$OR^{10}$, —$SR^{10}$, —$S(O)R^{10}$, —$S(O)_2R^{10}$, —$SO_2NH_2$, —$C(O)NH_2$, —$C(O)R^{10}$, —$C(NH)R^{10}$, —NHC(O)$R^{10}$, —NHC(NH)$R^{10}$, —$NHC(O)NH_2$, —$CO_2H$, —$NH_2$, —$NHR^{10}$, —$N(R^{10})_2$, and —$N(R^{10})_3^+$.

The symbol $R^{10}$ is independently $C_{1-6}$ alkyl.

The subscript n is 0, 1, 2, or 3.

Formula (I) is with the proviso that when X is C—$R^4$, Y is C—$R^5$, $R^6$ is $R^{6a}$, and A is

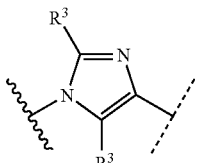

then $R^{6a}$ is bound to ring B through a carbon atom.

With respect to the above formula, there are a number of specific embodiments of the invention. In one group of embodiments, $R^1$ is 2-chloro.

In another group of embodiments, $R^2$ is hydrogen.

In another group of embodiments, X and Y are both CH.

In another group of embodiments, A is selected from the group consisting of:

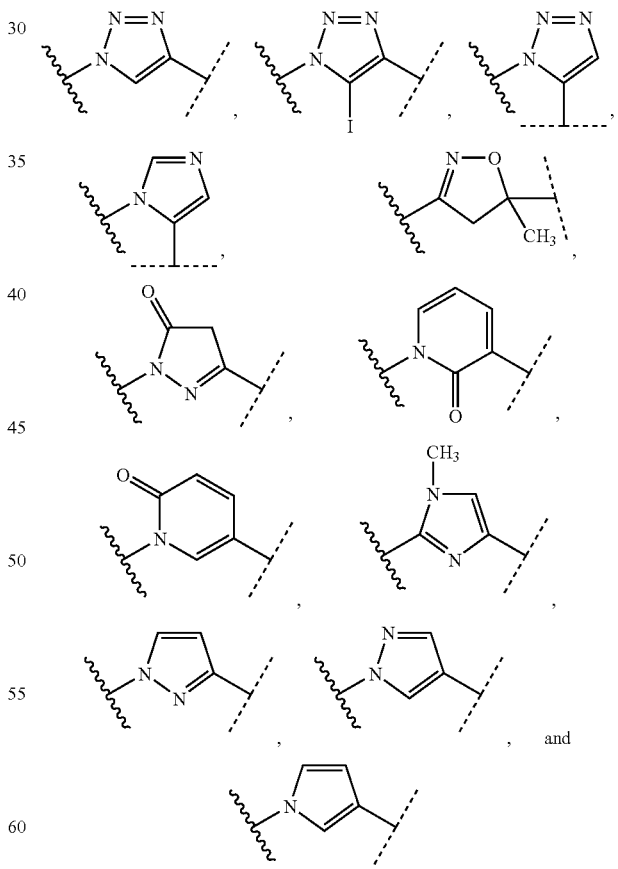

In another group of embodiments, $R^6$ is $R^{6a}$.

In another group of embodiments, $R^{6a}$ is selected from the group consisting of:

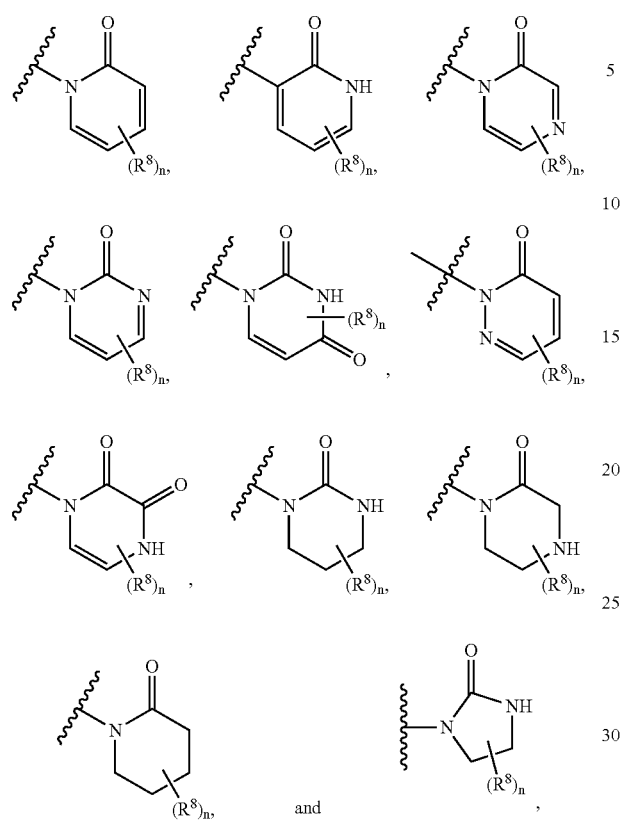
In another group of embodiments, $R^6$ is selected from the group consisting of:
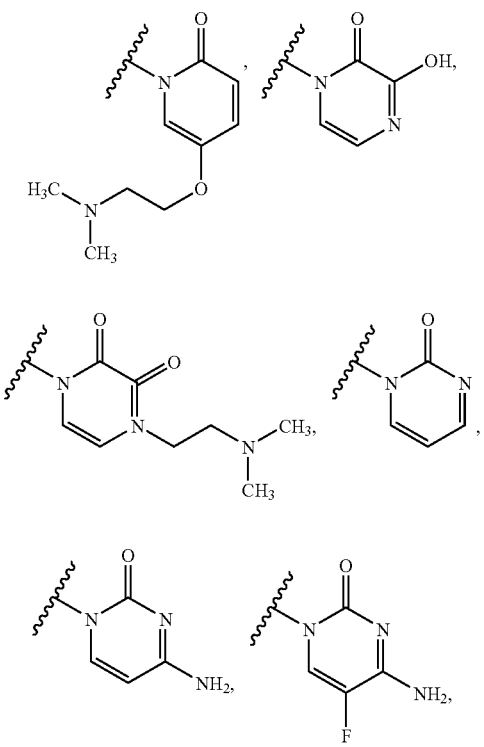
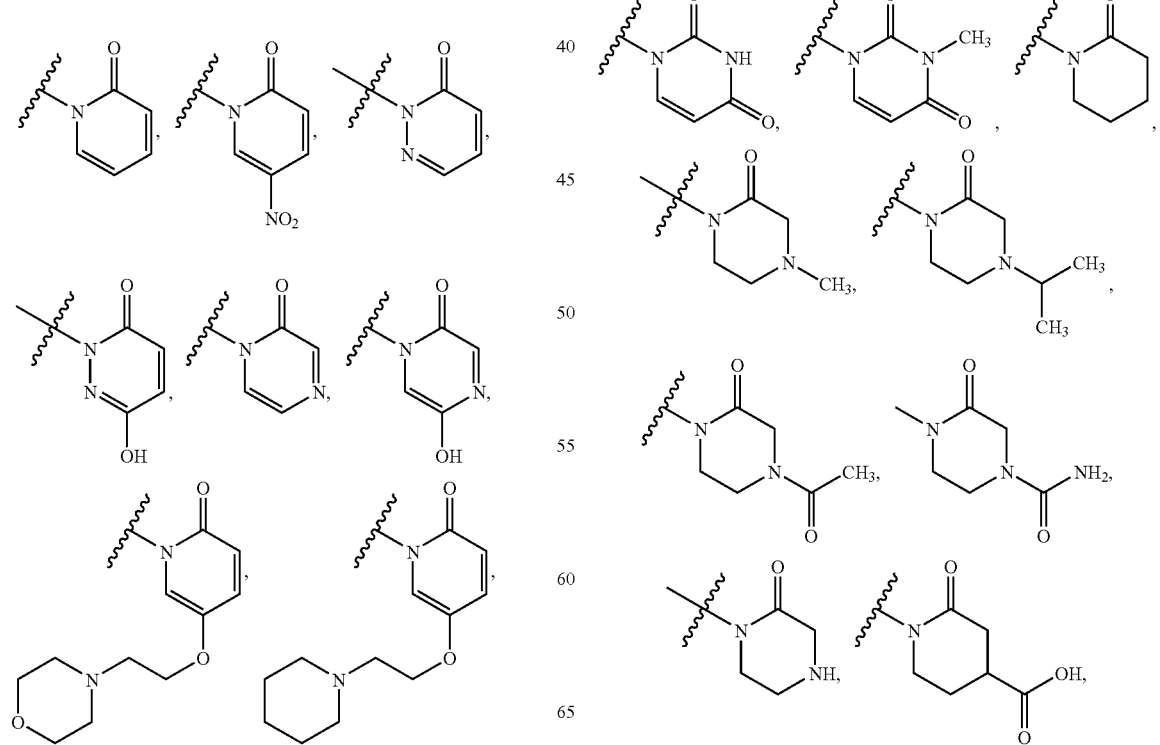
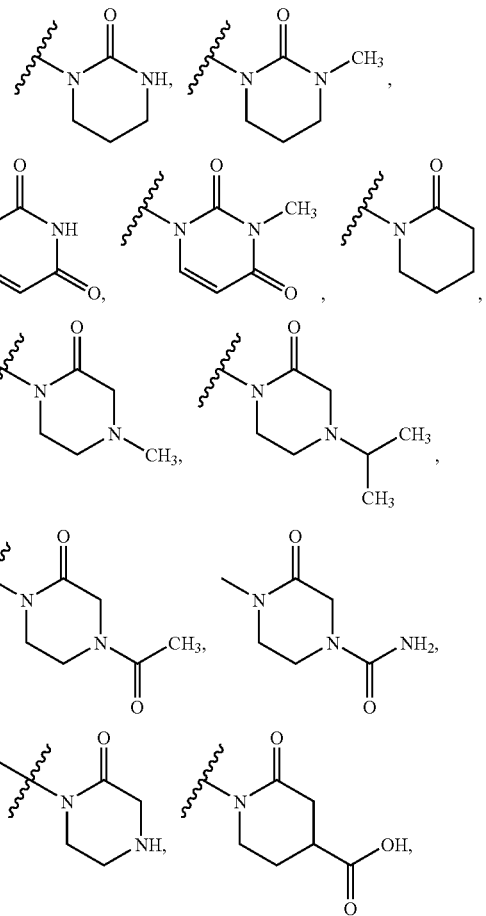

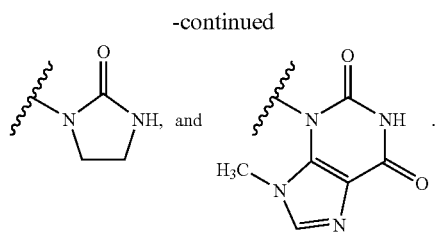
In another group of embodiments, $R^6$ is selected from the group consisting of:
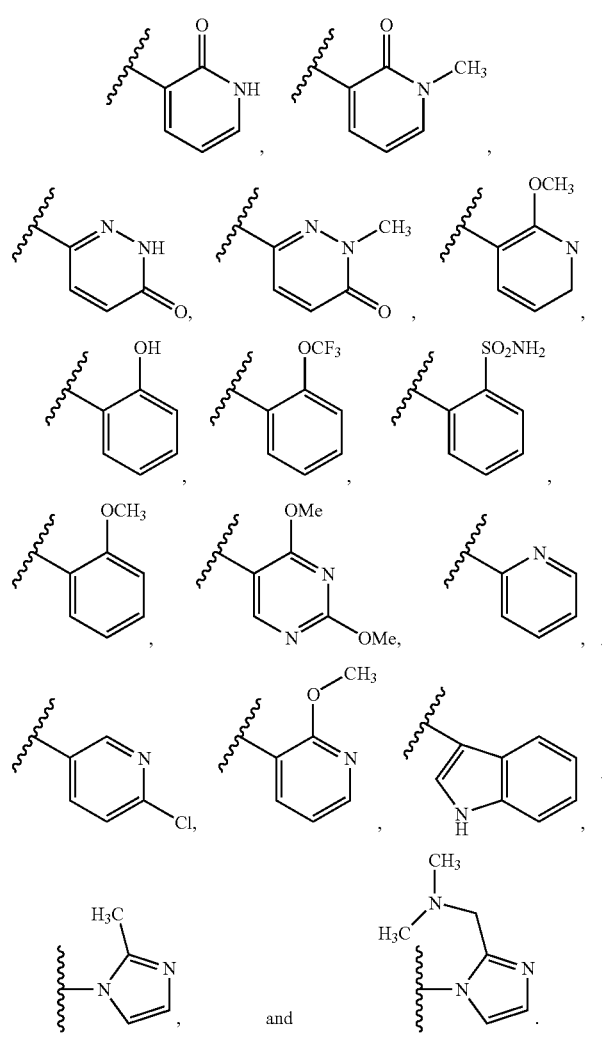
In another group of embodiments, $R^6$ is selected from the group consisting of:
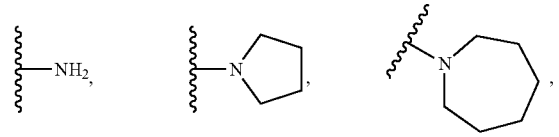
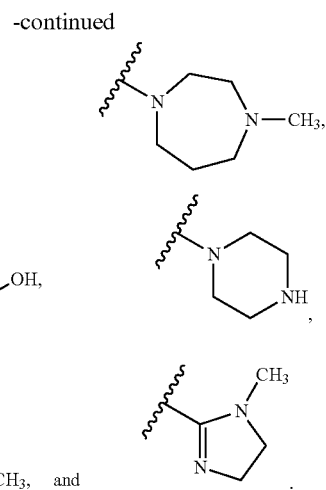
In another group of embodiments, $R^6$ is selected from the group consisting of:
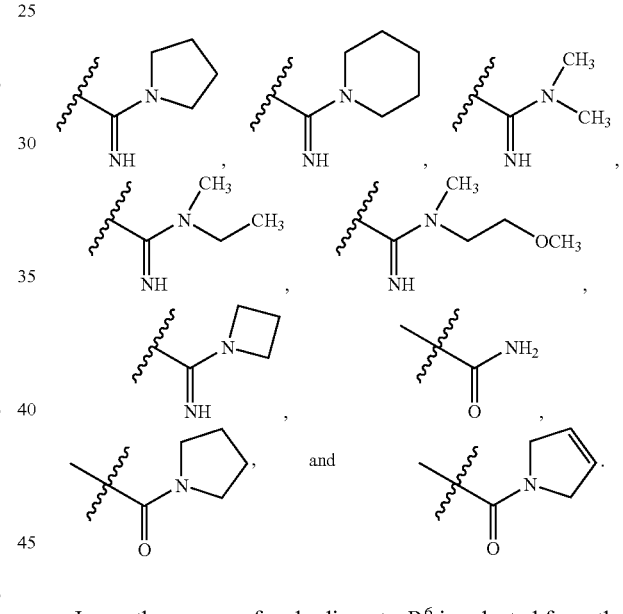
In another group of embodiments, $R^6$ is selected from the group consisting of:
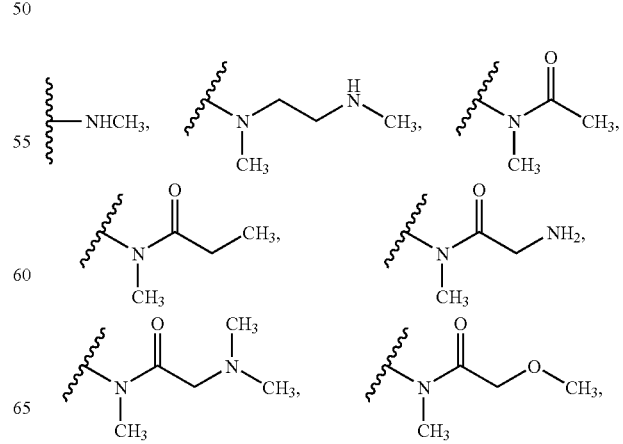

-continued

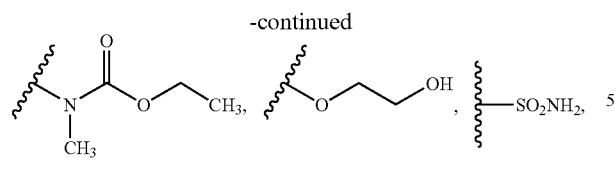

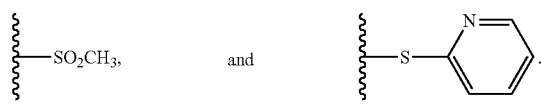

In another group of embodiments, $R^6$ is

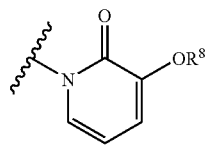

and $R^8$ is as previously defined. In still another group of embodiments, $R^8$ is selected from the group consisting of hydrogen,

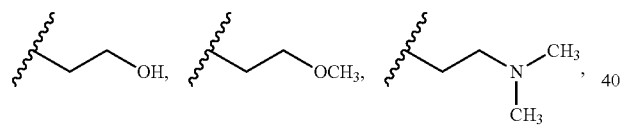

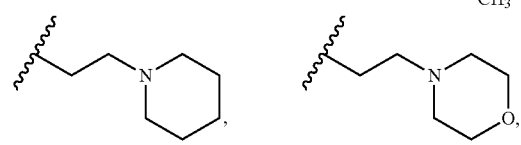

-continued

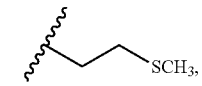

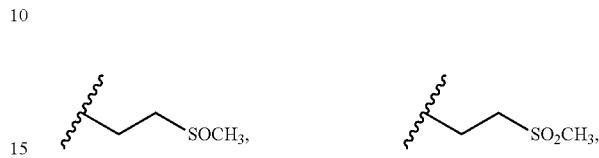

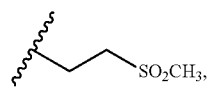

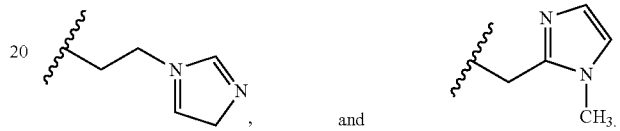

In another embodiment, ring B is

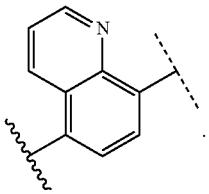

In another embodiment, the compound is a compound selected from Table 1 or a pharmaceutically acceptable salt, ester, or prodrug thereof.

TABLE 1

| Compound | Structure | Name |
| --- | --- | --- |
| 1 | 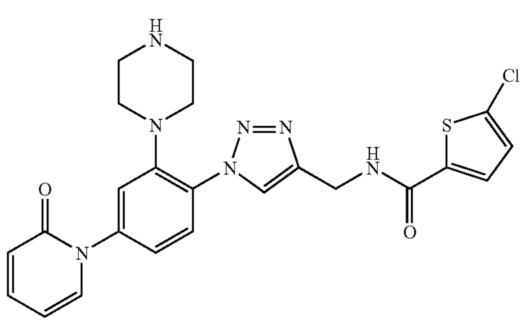 | 5-Chloro-N-((1-(4-(2-oxopyridin-1(2H)-yl)-2-(piperazin-1-yl)phenyl)-1H-1,2,3-triazol-4-yl)methyl)thiophene-2-carboxamide |

TABLE 1-continued

| Compound | Structure | Name |
| --- | --- | --- |
| 2 | 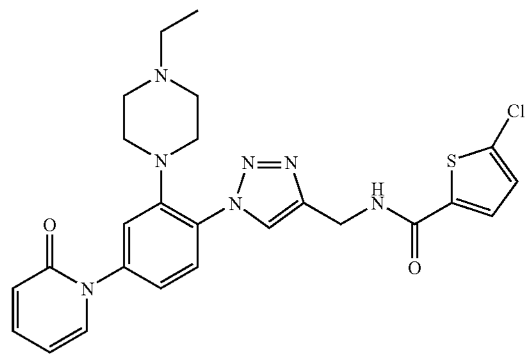 | 5-Chloro-N-((1-(2-(4-ethylpiperazin-1-yl)-4-(2-oxopyridin-1(2H)-yl)phenyl)-1H-1,2,3-triazol-4-yl)methyl)thiophene-2-carboxamide |
| 3 | 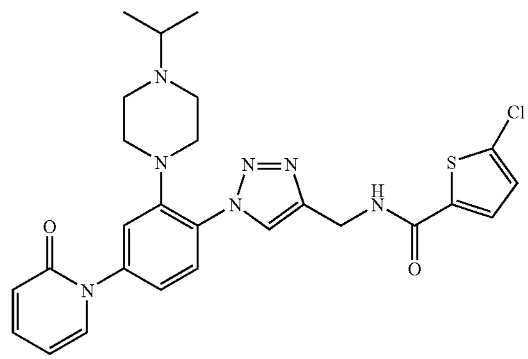 | 5-Chloro-N-((1-(2-(4-isopropylpiperazin-1-yl)-4-(2-oxopyridin-1(2H)-yl)phenyl)-1H-1,2,3-triazol-4-yl)methyl)thiophene-2-carboxamide |
| 4 | 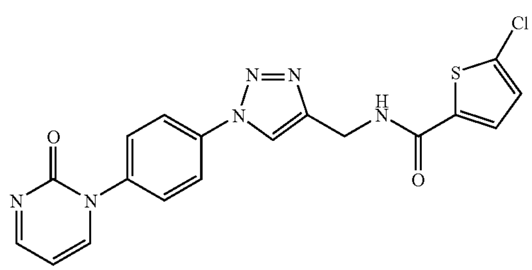 | 5-Chloro-N-((1-(4-(2-oxopyrimidin-1(2H)-yl)phenyl)-1H-1,2,3-triazol-4-yl)methyl)thiophene-2-carboxamide |
| 5 | 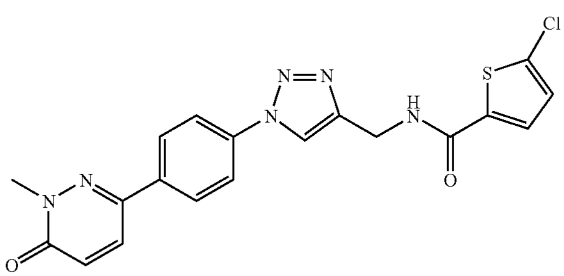 | 5-Chloro-N-((1-(4-(1-methyl-6-oxo-1,6-dihydropyridazin-3-yl)phenyl)-1H-1,2,3-triazol-4-yl)methyl)thiophene-2-carboxamide |
| 6 | 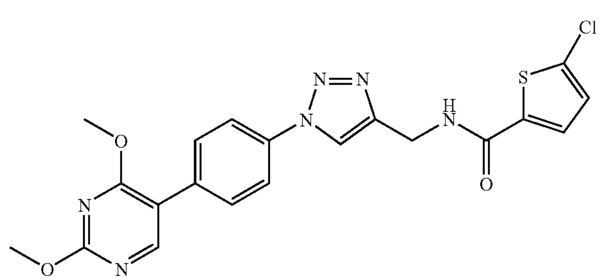 | 5-Chloro-N-((1-(4-(2,4-dimethoxypyrimidin-5-yl)phenyl)-1H-1,2,3-triazol-4-yl)methyl)thiophene-2-carboxamide |

TABLE 1-continued

| Compound | Structure | Name |
|---|---|---|
| 7 | 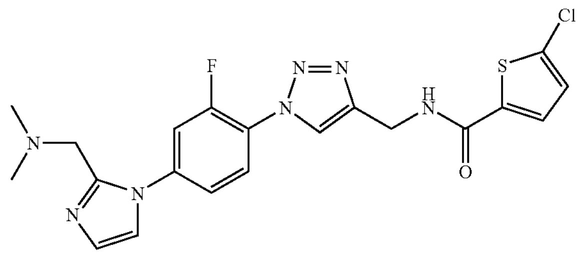 | 5-Chloro-N-((1-(4-(2-((dimethylamino)methyl)-1H-imidazol-1-yl)-2-fluorophenyl)-1H-1,2,3-triazol-4-yl)methyl)thiophene-2-carboxamide |
| 8 | 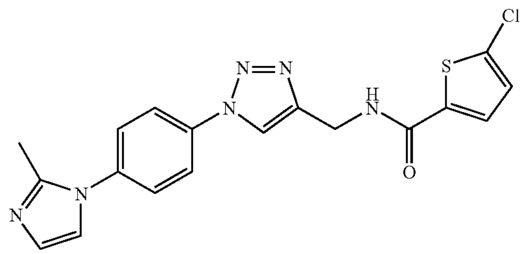 | 5-Chloro-N-((1-(4-(2-methyl-1H-imidazol-1-yl)phenyl)-1H-1,2,3-triazol-4-yl)methyl)thiophene-2-carboxamide |
| 9 | 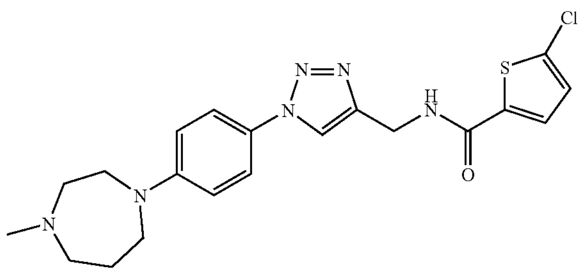 | 5-Chloro-N-((1-(4-(4-methyl-1,4-diazepan-1-yl)phenyl)-1H-1,2,3-triazol-4-yl)methyl)thiophene-2-carboxamide |
| 10 | 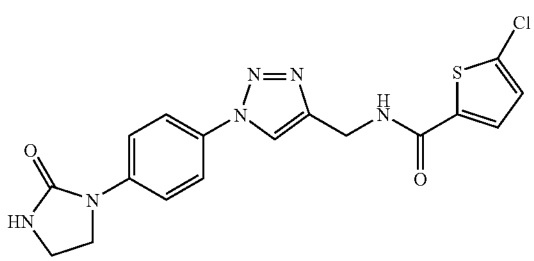 | 5-Chloro-N-((1-(4-(2-oxoimidazolidin-1-yl)phenyl)-1H-1,2,3-triazol-4-yl)methyl)thiophene-2-carboxamide |
| 11 | 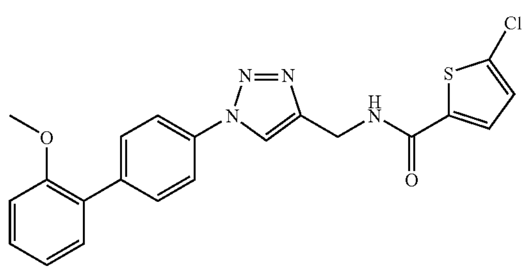 | 5-Chloro-N-((1-(2'-methoxybiphenyl-4-yl)-1H-1,2,3-triazol-4-yl)methyl)thiophene-2-carboxamide |
| 12 | 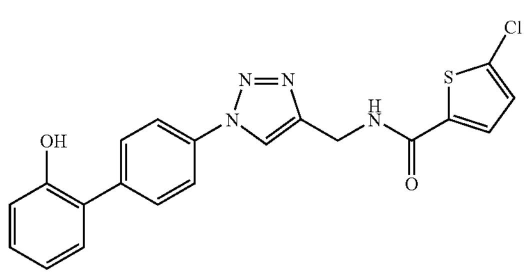 | 5-Chloro-N-((1-(2'-hydroxybiphenyl-4-yl)-1H-1,2,3-triazol-4-yl)methyl)thiophene-2-carboxamide |

TABLE 1-continued

| Compound | Structure | Name |
|---|---|---|
| 13 | 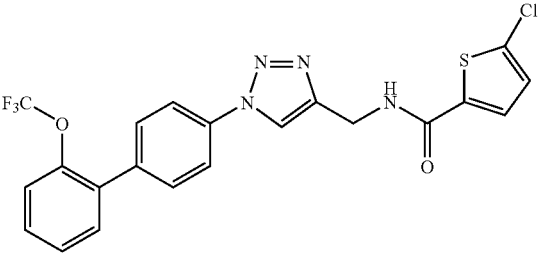 | 5-Chloro-N-((1-(2'-trifluoromethoxy)biphenyl-4-yl)-1H-1,2,3-triazol-4-yl)methyl)thiophene-2-carboxamide |
| 14 | 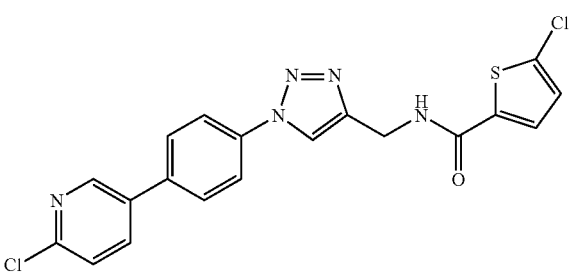 | 5-Chloro-N-((1-(4-(6-chloropyridin-3-yl)phenyl)-1H-1,2,3-triazol-4-yl)methyl)thiophene-2-carboxamide |
| 15 | 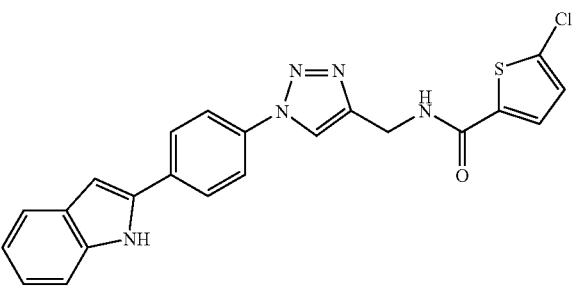 | N-((1-(4-(1H-Indol-2-yl)phenyl)-1H-1,2,3-triazol-4-yl)methyl)-5-chlorothiophene-2-carboxamide |
| 16 | 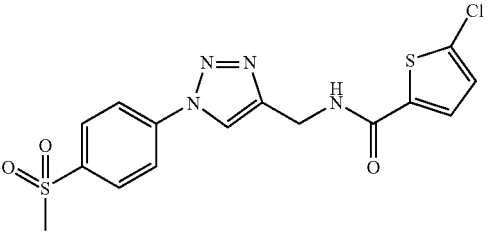 | 5-Chloro-N-((1-(4-(methylsulfonyl)phenyl)-1H-1,2,3-triazol-4-yl)methyl)thiophene-2-carboxamide |
| 17 | 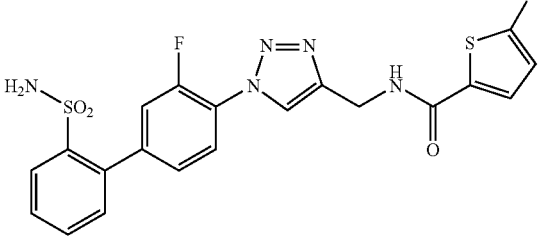 | 5-Chloro-N-((1-(3-fluoro-2'-sulfamoylbiphenyl-4-yl)-1H-1,2,3-triazol-4-yl)methyl)thiophene-2-carboxamide |

TABLE 1-continued

| Compound | Structure | Name |
|---|---|---|
| 18 | 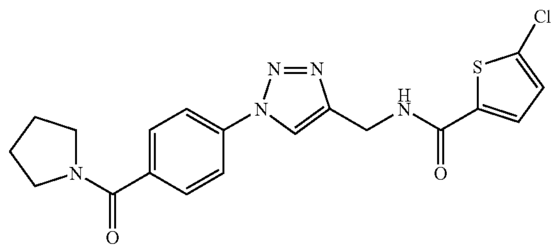 | 5-Chloro-N-((1-(4-(pyrrolidine-1-carbonyl)phenyl)-1H-1,2,3-triazol-4-yl)methyl)thiophene-2-carboxamide |
| 19 | 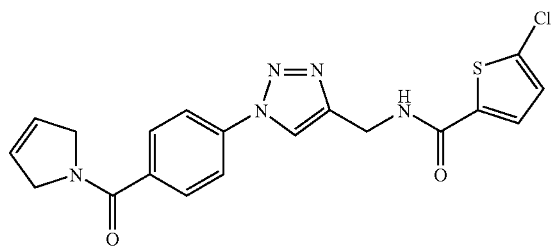 | 5-Chloro-N-((1-(4-(2,5-dihydro-1H-pyrrole-1-carbonyl)phenyl)-1H-1,2,3-triazol-4-yl)methyl)thiophene-2-carboxamide |
| 20 | 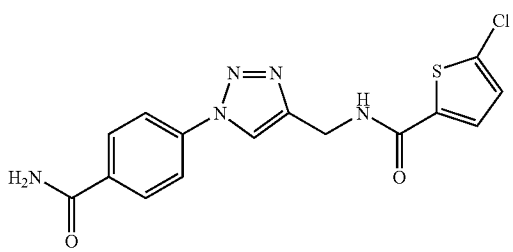 | N-((1-(4-Carbamoylphenyl)-1H-1,2,3-triazol-4-yl)methyl)-5-chlorothiophene-2-carboxamide |
| 21 | 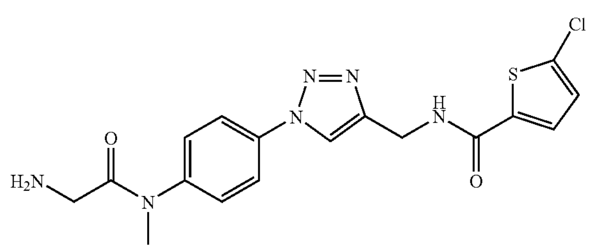 | N-((1-(4-(2-Amino-N-methylacetamido)phenyl)-1H-1,2,3-triazol-4-yl)methyl)-5-chlorothiophene-2-carboxamide |
| 22 | 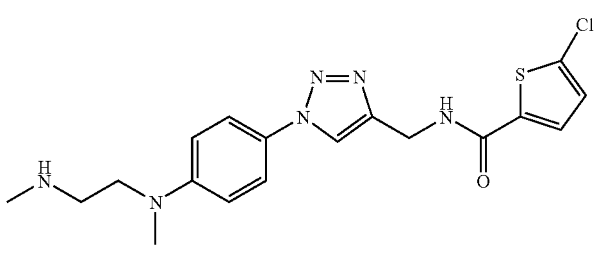 | 5-Chloro-N-((1-(4-(methyl(2-(methylamino)ethyl)amino)phenyl)-1H-1,2,3-triazol-4-yl)methyl)thiophene-2-carboxamide |
| 23 | 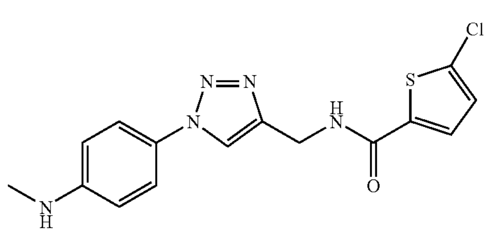 | 5-Chloro-N-((1-(4-(methylamino)phenyl)-1H-1,2,3-triazol-4-yl)methyl)thiophene-2-carboxamide |

TABLE 1-continued

| Compound | Structure | Name |
|---|---|---|
| 24 | 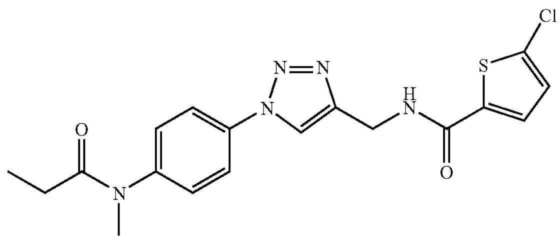 | 5-Chloro-N-((1-(4-(N-methylpropionamido)phenyl)-1H-1,2,3-triazol-4-yl)methyl)thiophene-2-carboxamide |
| 25 | 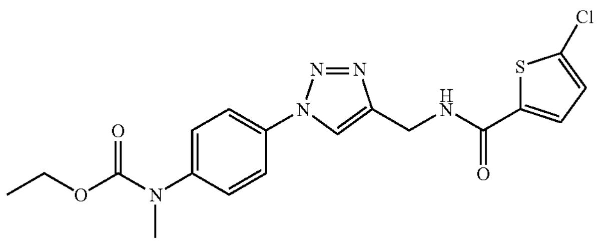 | Ethyl 4-(4-((5-chlorothiophene-2-carboxamido)methyl)-1H-1,2,3-triazol-1-yl)phenyl(methyl)carbamate |
| 26 | 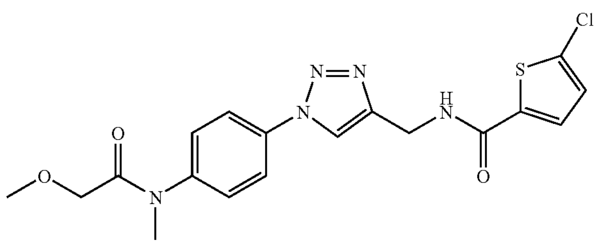 | 5-Chloro-N-((1-(4-(2-methoxy-N-methylacetamido)phenyl)-1H-1,2,3-triazol-4-yl)methyl)thiophene-2-carboxamide |
| 27 | 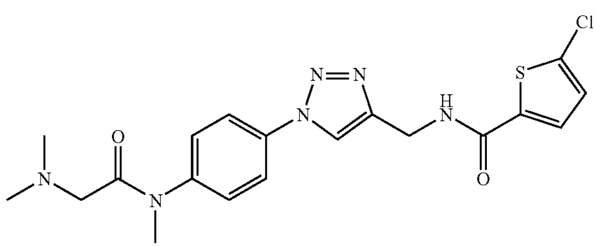 | 5-Chloro-N-((1-(4-(2-(dimethylamino)-N-methylacetamido)phenyl)-1H-1,2,3-triazol-4-yl)methyl)thiophene-2-carboxamide |
| 28 | 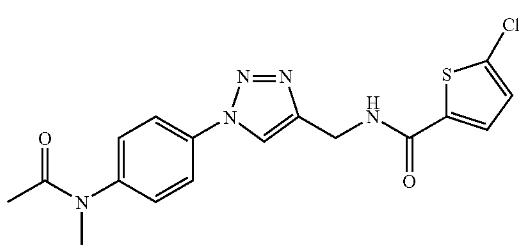 | 5-Chloro-N-((1-(4-(N-methylacetamido)phenyl)-1H-1,2,3-triazol-4-yl)methyl)thiophene-2-carboxamide |
| 29 | 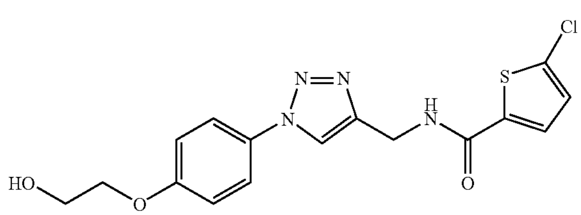 | 5-Chloro-N-((1-(4-(2-hydroxyethoxy)phenyl)-1H-1,2,3-triazol-4-yl)methyl)thiophene-2-carboxamide |

TABLE 1-continued

| Compound | Structure | Name |
|---|---|---|
| 30 | 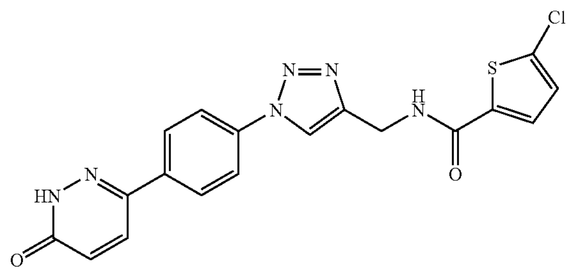 | 5-Chloro-N-((1-(4-(6-oxo-1,6-dihydropyridazin-3-yl)phenyl)-1H-1,2,3-triazol-4-yl)methyl)thiophene-2-carboxamide |
| 31 | 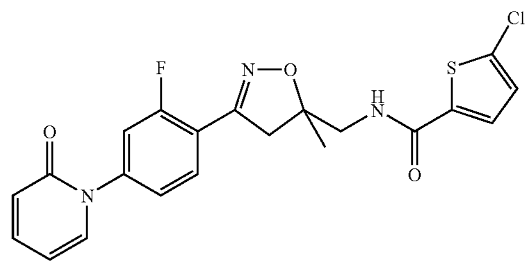 | 5-Chloro-N-((3-(2-fluoro-4-(2-oxopyridin-1(2H)-yl)phenyl)-5-methyl-4,5-dihydroisoxazol-5-yl)methyl)thiophene-2-carboxamide |
| 32 | 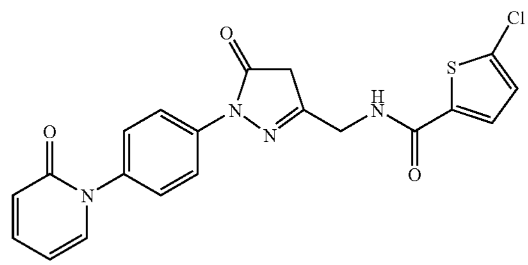 | 5-Chloro-N-((5-oxo-1-(4-(2-oxopyridin-1(2H)-yl)phenyl)-4,5-dihydro-1H-pyrazol-3-yl)methyl)thiophene-2-carboxamide |
| 33 | 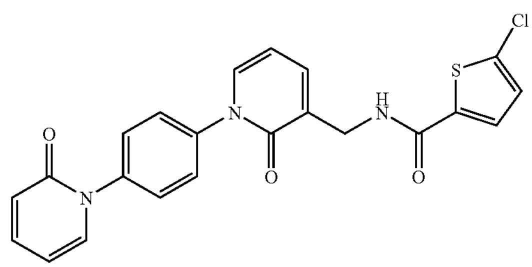 | 5-Chloro-N-((2-oxo-1-(4-(2-oxopyridin-1(2H)-yl)phenyl)-1,2-dihydropyridin-3-yl)methyl)thiophene-2-carboxamide |
| 34 | 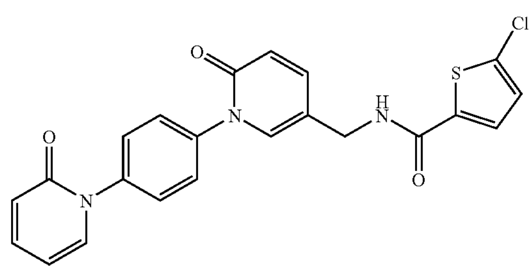 | 5-Chloro-N-((6-oxo-1-(4-(2-oxopyridin-1(2H)-yl)phenyl)-1,6-dihydropyridin-3-yl)methyl)thiophene-2-carboxamide |
| 35 | 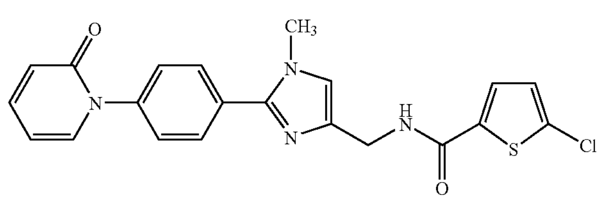 | 5-Chloro-N-((1-methyl-2-(4-(2-oxopyridin-1(2H)-yl)phenyl)-1H-imidazol-4-yl)methyl)thiophene-2-carboxamide |

TABLE 1-continued

| Compound | Structure | Name |
|---|---|---|
| 36 | 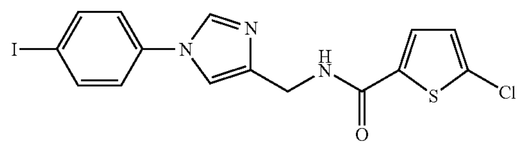 | 5-Chloro-N-((1-(4-iodophenyl)-1H-imidazol-4-yl)methyl)thiophene-2-carboxamide |
| 37 | 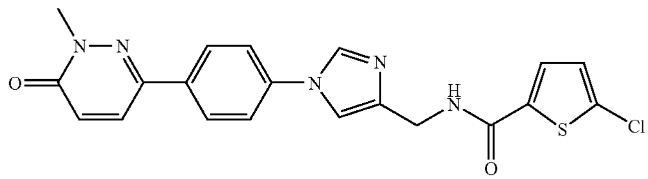 | 5-Chloro-N-((1-(4-(1-methyl-6-oxo-1,6-dihydropyridazin-3-yl)phenyl)-1H-imidazol-4-yl)methyl)thiophene-2-carboxamide |
| 38 | 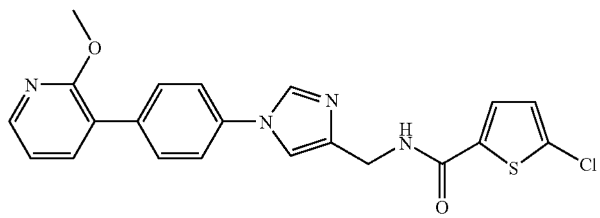 | 5-Chloro-N-((1-(4-(2-methoxypyridin-3-yl)phenyl)-1H-imidazol-4-yl)methyl)thiophene-2-carboxamide |
| 39 | 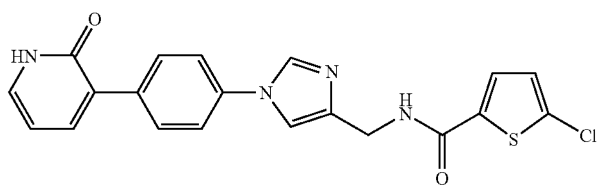 | 5-Chloro-N-((1-(4-(2-oxo-1,2-dihydropyridin-3-yl)phenyl)-1H-imidazol-4-yl)methyl)thiophene-2-carboxamide |
| 40 | 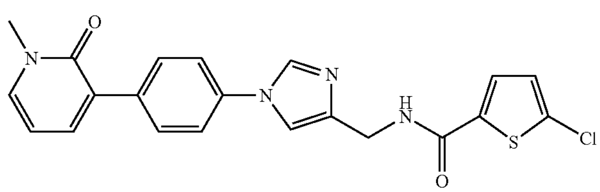 | 5-Chloro-N-((1-(4-(1-methyl-2-oxo-1,2-dihydropyridin-3-yl)phenyl)-1H-imidazol-4-yl)methyl)thiophene-2-carboxamide |
| 41 | 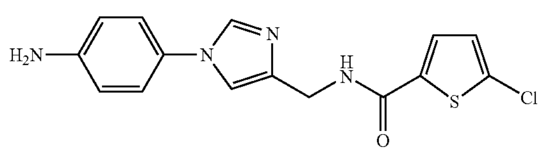 | N-((1-(4-Aminophenyl)-1H-imidazol-4-yl)methyl)-5-chlorothiophene-2-carboxamide |
| 42 | 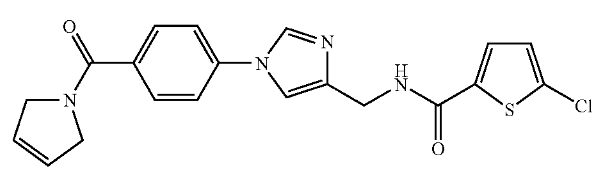 | 5-Chloro-N-((1-(4-(2,5-dihydro-1H-pyrrole-1-carbonyl)phenyl)-1H-imidazol-4-yl)methyl)thiophene-2-carboxamide |
| 43 | 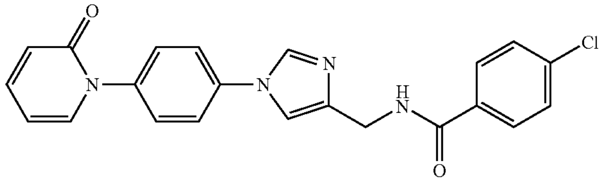 | 4-Chloro-N-((1-(4-(2-oxopyridin-1(2H)-yl)phenyl)-1H-imidazol-4-yl)methyl)benzamide |

TABLE 1-continued

| Compound | Structure | Name |
|---|---|---|
| 44 | 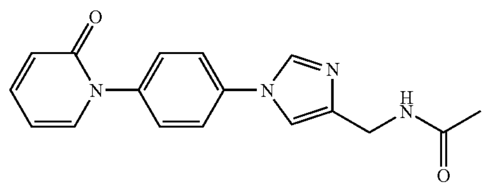 | N-((1-(4-(2-Oxopyridin-1(2H)-yl)phenyl)-1H-imidazol-4-yl)methyl)acetamide |
| 45 | 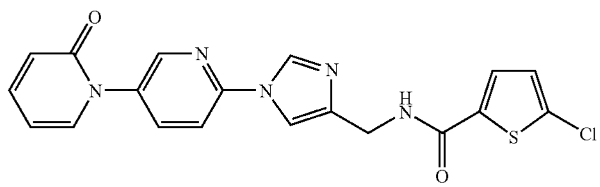 | 5-Chloro-N-((1-(5-(2-oxopyridin-1(2H)-yl)pyridin-2-yl)-1H-imidazol-4-yl)methyl)thiophene-2-carboxamide |
| 46 | 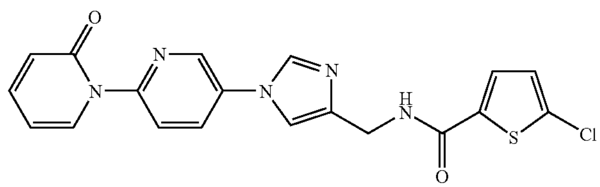 | 5-Chloro-N-((1-(6-(2-oxopyridin-1(2H)-yl)pyridin-3-yl)-1H-imidazol-4-yl)methyl)thiophene-2-carboxamide |
| 47 | 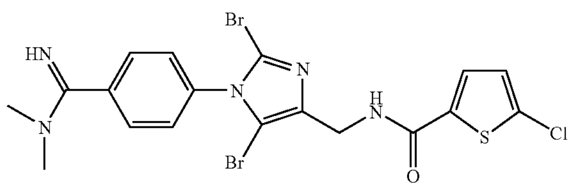 | 5-Chloro-N-((2,5-dibromo-1-(4-(N,N-dimethylcarbamimidoyl)phenyl)-1H-imidazol-4-yl)methyl)thiophene-2-carboxamide |
| 48 | 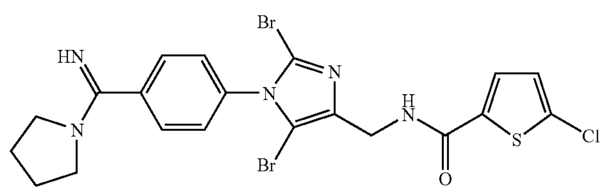 | 5-Chloro-N-((2,5-dibromo-1-(4-(imino(pyrrolidin-1-yl)methyl)phenyl)-1H-imidazol-4-yl)methyl)thiophene-2-carboxamide |
| 49 | 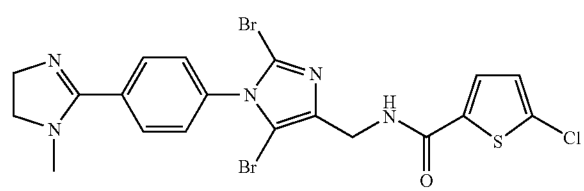 | 5-Chloro-N-((2,5-dibromo-1-(4-(1-methyl-4,5-dihydro-1H-imidazol-2-yl)phenyl)-1H-imidazol-4-yl)methyl)thiophene-2-carboxamide |
| 50 | 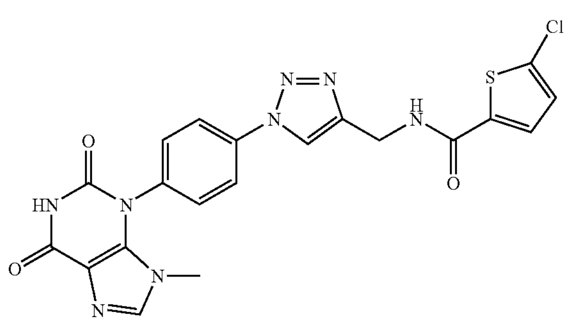 | 5-Chloro-N-((1-(4-(9-methyl-2,6-dioxo-1H-purin-3(2H,6H,9H)-yl)phenyl)-1H-1,2,3-triazol-4-yl)methyl)thiophene-2-carboxamide |

TABLE 1-continued

| Compound | Structure | Name |
|---|---|---|
| 51 | 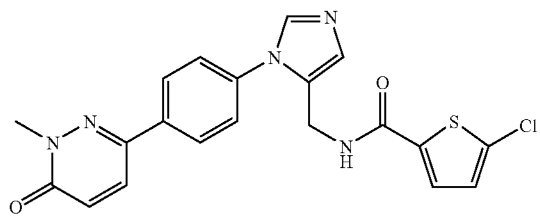 | 5-Chloro-N-((1-(4-(1-methyl-6-oxo-1,6-dihydropyridazin-3-yl)phenyl)-1H-imidazol-5 yl)methyl)thiophene-2-carboxamide |
| 52 | 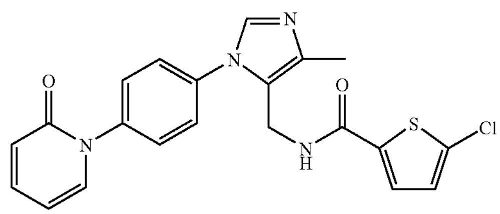 | 5-Chloro-N-((4-methyl-1-(4-(2-oxopyridin-1(2H)-yl)phenyl)-1H-imidazol-5-yl)methyl)thiophene-2-carboxamide |
| 53 | 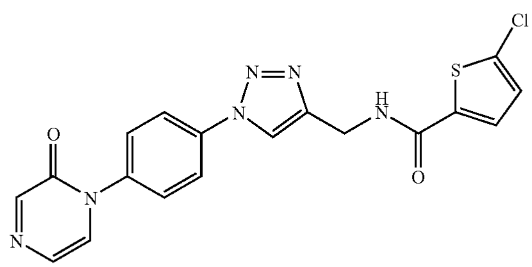 | 5-Chloro-N-((1-(4-(2-oxopyrazin-1(2H)-yl)phenyl)-1H-1,2,3-triazol-4-yl)methyl)thiophene-2-carboxamide |
| 54 | 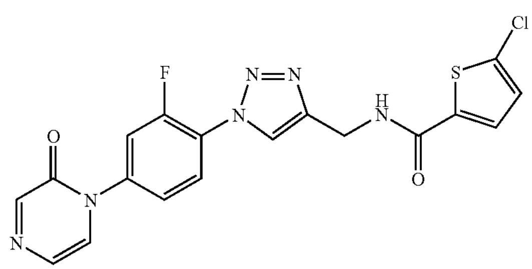 | 5-Chloro-N-((1-(2-fluoro-4-(2-oxopyrazin-1(2H)-yl)phenyl)-1H-1,2,3-triazol-4-yl)methyl)thiophene-2-carboxamide |
| 55 | 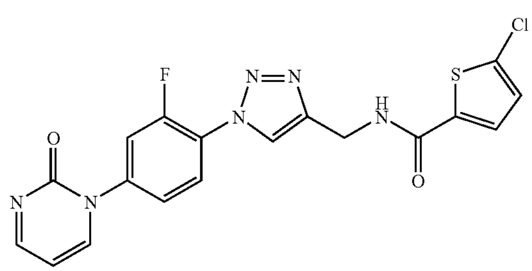 | 5-Chloro-N-((1-(2-fluoro-4-(2-oxopyrimidin-1(2H)-yl)phenyl)-1H-1,2,3-triazol-4-yl)methyl)thiophene-2-carboxamide |
| 56 | 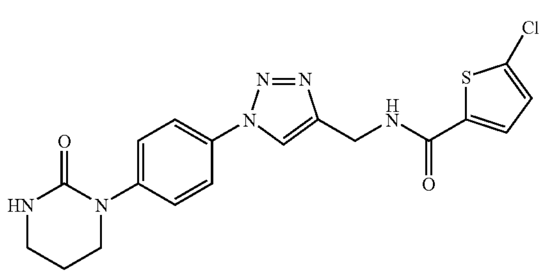 | 5-Chloro-N-((1-(4-(2-oxotetrahydropyrimidin-1(2H)-yl)phenyl)-1H-1,2,3-triazol-4-yl)methyl)thiophene-2-carboxamide |

TABLE 1-continued

| Compound | Structure | Name |
|---|---|---|
| 57 | 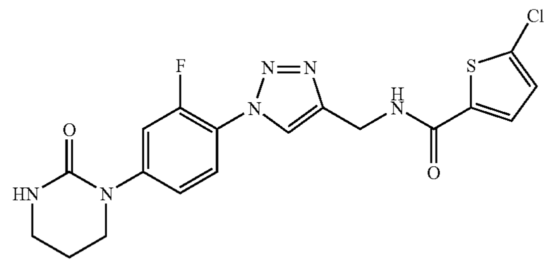 | 5-Chloro-N-((1-(2-fluoro-4-(2-oxo-tetrahydropyrimidin-1(2H)-yl)phenyl)-1H-1,2,3-triazol-4-yl)methyl)thiophene-2-carboxamide |
| 58 | 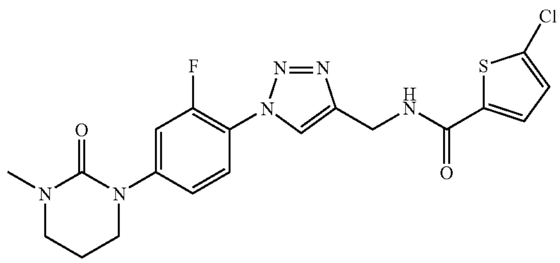 | 5-Chloro-N-((1-(2-fluoro-4-(3-methyl-2-oxo-tetrahydropyrimidin-1(2H)-yl)phenyl)-1H-1,2,3-triazol-4-yl)methyl)thiophene-2-carboxamide |
| 59 | 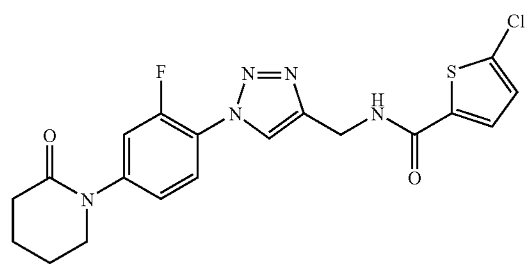 | 5-Chloro-N-((1-(2-fluoro-4-(2-oxopiperidin-1-yl)phenyl)-1H-1,2,3-triazol-4-yl)methyl)thiophene-2-carboxamide |
| 60 | 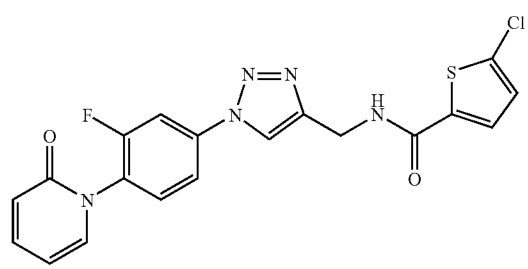 | 5-Chloro-N-((1-(3-fluoro-4-(2-oxopyridin-1(2H)-yl)phenyl)-1H-1,2,3-triazol-4-yl)methyl)thiophene-2-carboxamide |
| 61 | 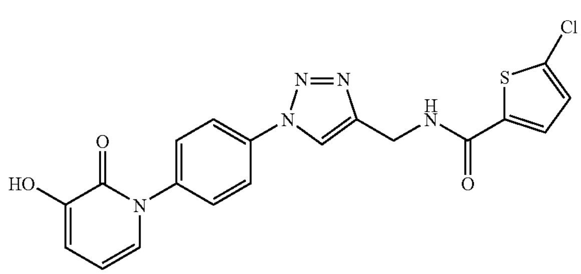 | 5-Chloro-N-((1-(4-(3-hydroxy-2-oxopyridin-1(2H)-yl)phenyl)-1H-1,2,3-triazol-4-yl)methyl)thiophene-2-carboxamide |

TABLE 1-continued

| Compound | Structure | Name |
| --- | --- | --- |
| 62 | 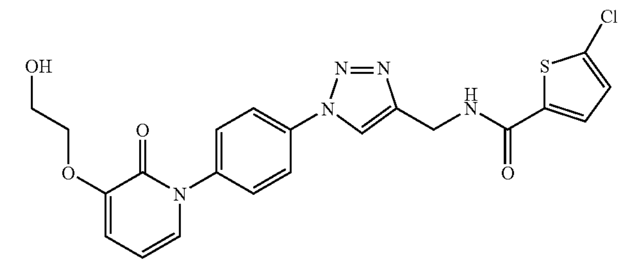 | 5-Chloro-N-((1-(4-(3-(2-hydroxyethoxy)-2-oxopyridin-1(2H)-yl)phenyl)-1H-1,2,3-triazol-4-yl)methyl)thiophene-2-carboxamide |
| 63 | 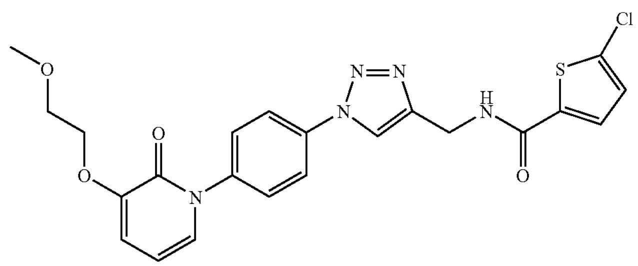 | 5-Chloro-N-((1-(4-(3-(2-methoxyethoxy)-2-oxopyridin-1(2H)-yl)phenyl)-1H-1,2,3-triazol-4-yl)methyl)thiophene-2-carboxamide |
| 64 | 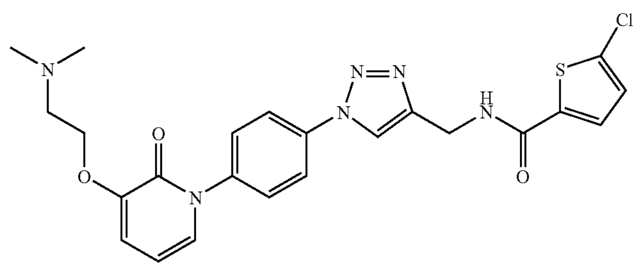 | 5-Chloro-N-((1-(4-(3-(2-(dimethylamino)ethoxy)-2-oxopyridin-1(2H)-yl)phenyl)-1H-1,2,3-triazol-4-yl)methyl)thiophene-2-carboxamide |
| 65 | 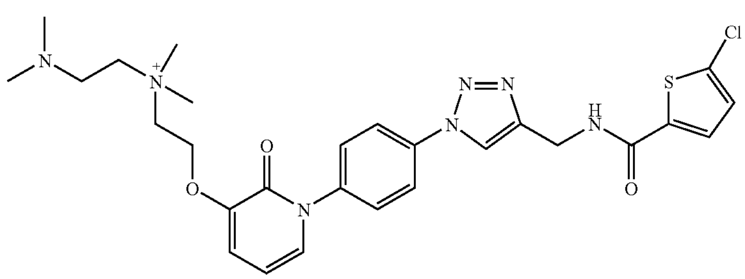 | 5-Chloro-N-((1-(4-(3-(2-(dimethyl(dimethylamino)amino)ethoxy)-2-oxopyridin-1(2H)-yl)phenyl)-1H-1,2,3-triazol-4-yl)methyl)thiophene-2-carboxamide |
| 66 | 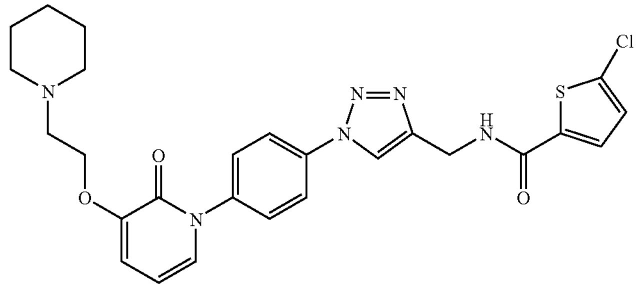 | 5-Chloro-N-((1-(4-(2-oxo-3-(2-(piperidin-1-yl)ethoxy)pyridin-1(2H)-yl)phenyl)-1H-1,2,3-triazol-4-yl)methyl)thiophene-2-carboxamide |

TABLE 1-continued

| Compound | Structure | Name |
|---|---|---|
| 67 | 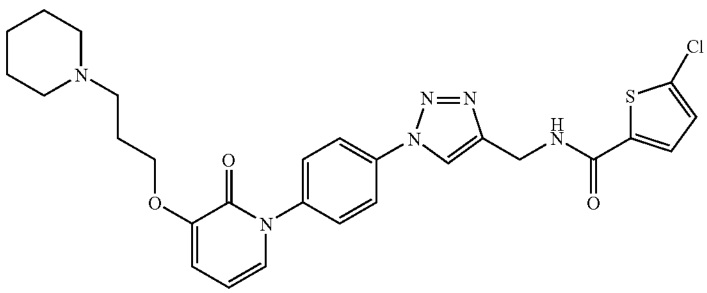 | 5-Chloro-N-((1-(4-(2-oxo-3-(3-(piperidin-1-yl)propoxy)pyridin-1(2H)-yl)phenyl)-1H-1,2,3-triazol-4-yl)methyl)thiophene-2-carboxamide |
| 68 | 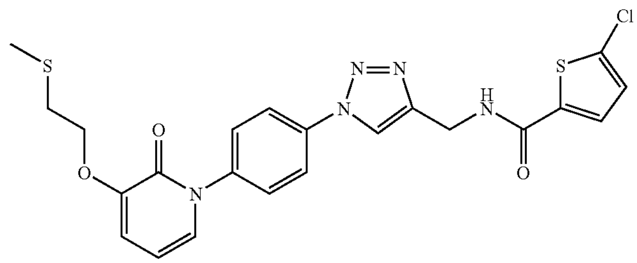 | 5-Chloro-N-((1-(4-(3-(2-(methylthio)ethoxy)-2-oxopyridin-1(2H)-yl)phenyl)-1H-1,2,3-triazol-4-yl)methyl)thiophene-2-carboxamide |
| 69 | 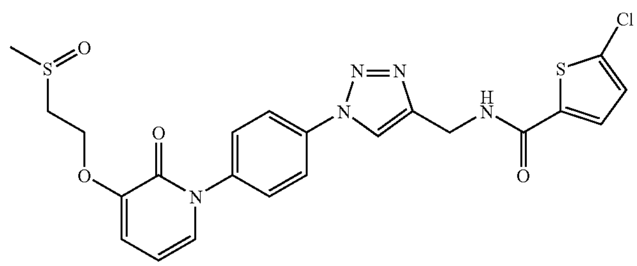 | 5-Chloro-N-((1-(4-(3-(2-(methylsulfinyl)ethoxy)-2-oxopyridin-1(2H)-yl)phenyl)-1H-1,2,3-triazol-4-yl)methyl)thiophene-2-carboxamide |
| 70 | 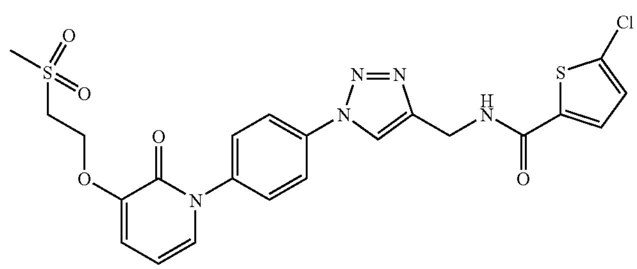 | 5-Chloro-N-((1-(4-(3-(2-(methylsulfonyl)ethoxy)-2-oxopyridin-1(2H)-yl)phenyl)-1H-1,2,3-triazol-4-yl)methyl)thiophene-2-carboxamide |
| 71 | 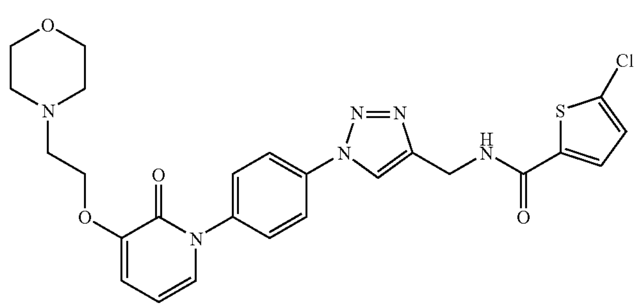 | 5-Chloro-N-((1-(4-(3-(2-morpholinoethoxy)-2-oxopyridin-1(2H)-yl)phenyl)-1H-1,2,3-triazol-4-yl)methyl)thiophene-2-carboxamide |

TABLE 1-continued

| Compound | Structure | Name |
|---|---|---|
| 72 | 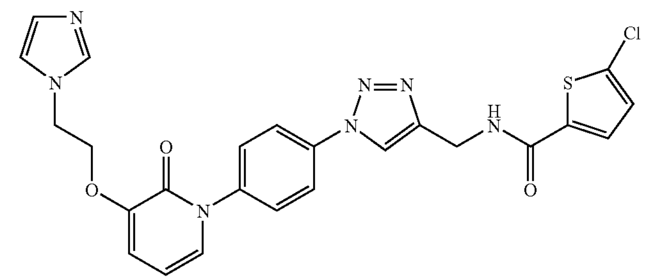 | N-((1-(4-(3-(2-(1H-Imidazol-1-yl)ethoxy)-2-oxopyridin-1(2H)-yl)phenyl)-1H-1,2,3-triazol-4-yl)methyl)-5-chlorothiophene-2-carboxamide |
| 73 | 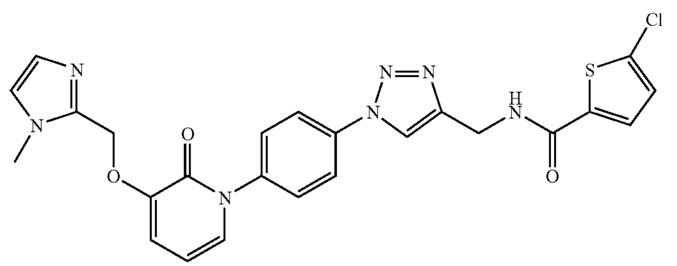 | 5-Chloro-N-((1-(4-(3-((1-methyl-1H-imidazol-2-yl)methoxy)-2-oxopyridin-1(2H)-yl)phenyl)-1H-1,2,3-triazol-4-yl)methyl)thiophene-2-carboxamide |
| 74 | 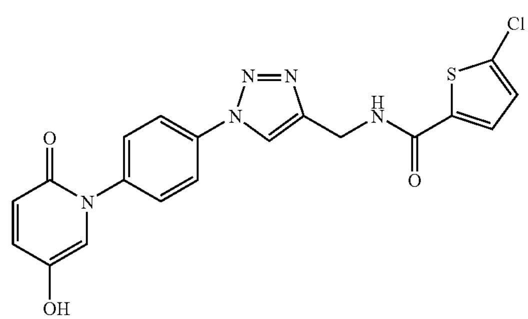 | 5-Chloro-N-((1-(4-(5-hydroxy-2-oxopyridin-1(2H)-yl)phenyl)-1H-1,2,3-triazol-4-yl)methyl)thiophene-2-carboxamide |
| 75 | 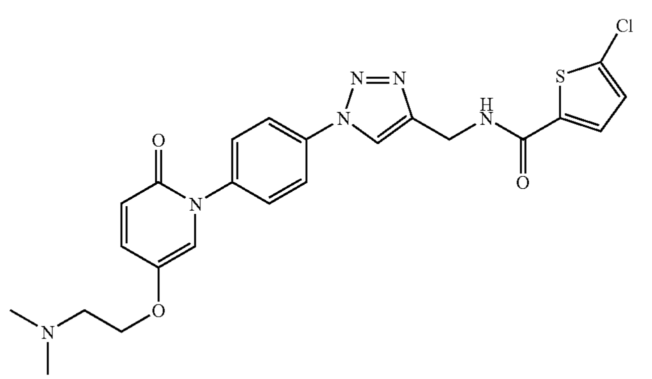 | 5-Chloro-N-((1-(4-(5-(2-(dimethylamino)ethoxy)-2-oxopyridin-1(2H)-yl)phenyl)-1H-1,2,3-triazol-4-yl)methyl)thiophene-2-carboxamide |

TABLE 1-continued

| Compound | Structure | Name |
|---|---|---|
| 76 | 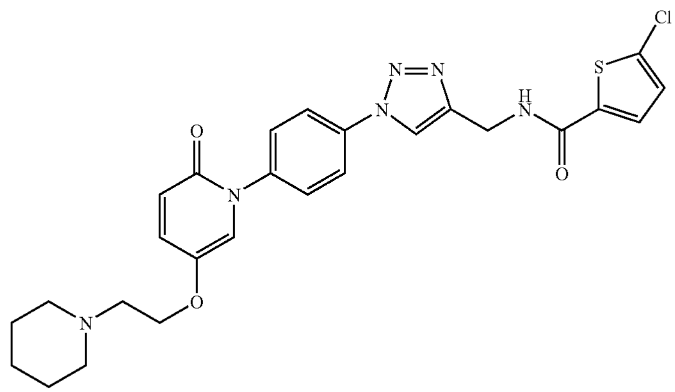 | 5-Chloro-N-((1-(4-(2-oxo-5-(2-(piperidin-1-yl)ethoxy)pyridin-1(2H)-yl)phenyl)-1H-1,2,3-triazol-4-yl)methyl)thiophene-2-carboxamide |
| 77 | 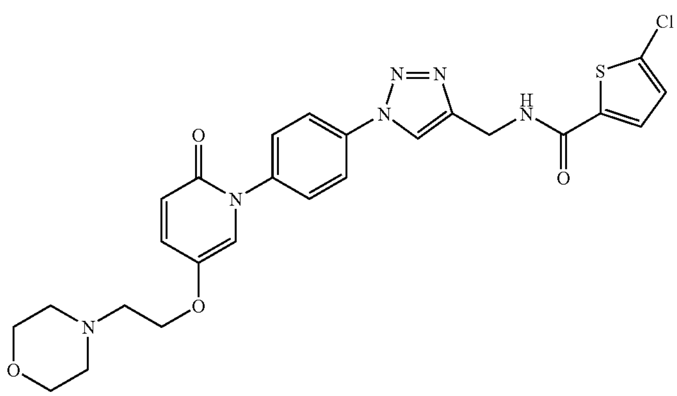 | 5-Chloro-N-((1-(4-(5-(2-morpholinoethoxy)-2-oxopyridin-1(2H)-yl)phenyl)-1H-1,2,3-triazol-4-yl)methyl)thiophene-2-carboxamide |
| 78 | 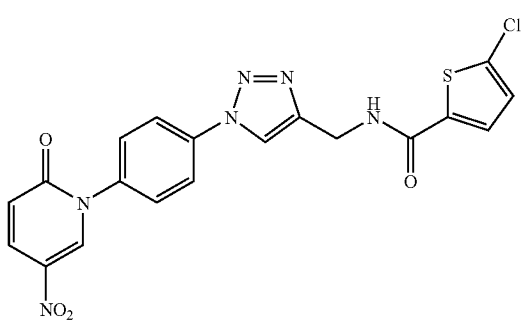 | 5-Chloro-N-((1-(4-(5-nitro-2-oxopyridin-1(2H)-yl)phenyl)-1H-1,2,3-triazol-4-yl)methyl)thiophene-2-carboxamide |
| 79 | 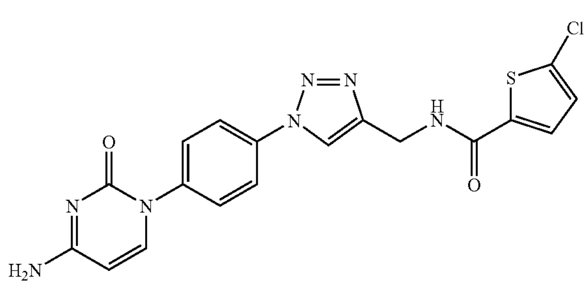 | N-((1-(4-(4-Amino-2-oxopyrimidin-1(2H)-yl)phenyl)-1H-1,2,3-triazol-4-yl)methyl)-5-chlorothiophene-2-carboxamide |

TABLE 1-continued

| Compound | Structure | Name |
|---|---|---|
| 80 | 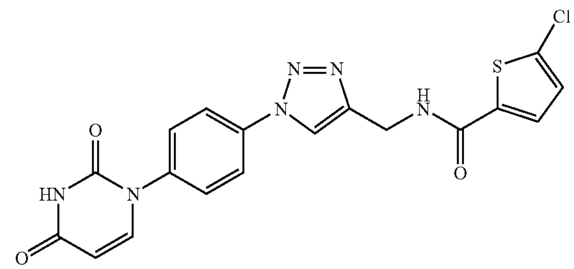 | 5-Chloro-N-((1-(4-(2,4-dioxo-3,4-dihydropyrimidin-1(2H)-yl)phenyl)-1H-1,2,3-triazol-4-yl)methyl)thiophene-2-carboxamide |
| 81 | 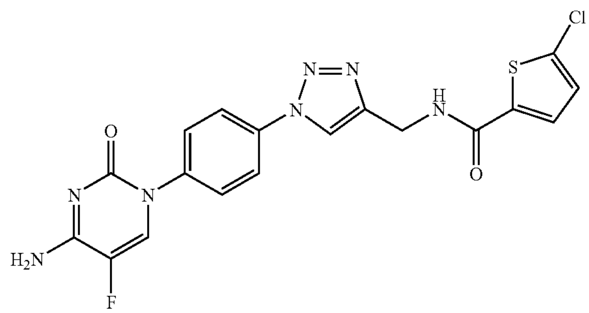 | N-((1-(4-(4-Amino-5-fluoro-2-oxopyrimidin-1(2H)-yl)phenyl)-1H-1,2,3-triazol-4-yl)methyl)-5-chlorothiophene-2-carboxamide |
| 82 | 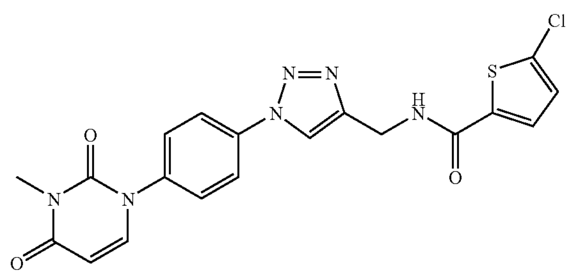 | 5-Chloro-N-((1-(4-(3-methyl-2,4-dioxo-3,4-dihydropyrimidin-1(2H)-yl)phenyl)-1H-1,2,3-triazol-4-yl)methyl)thiophene-2-carboxamide |
| 83 | 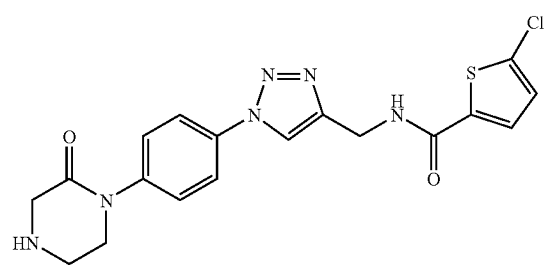 | 5-Chloro-N-((1-(4-(2-oxopiperazin-1-yl)phenyl)-1H-1,2,3-triazol-4-yl)methyl)thiophene-2-carboxamide |
| 84 | 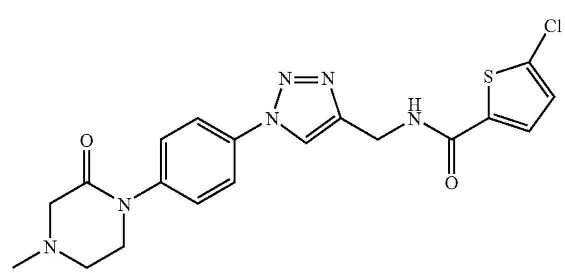 | 5-Chloro-N-((1-(4-(4-methyl-2-oxopiperazin-1-yl)phenyl)-1H-1,2,3-triazol-4-yl)methyl)thiophene-2-carboxamide |

TABLE 1-continued

| Compound | Structure | Name |
| --- | --- | --- |
| 85 | 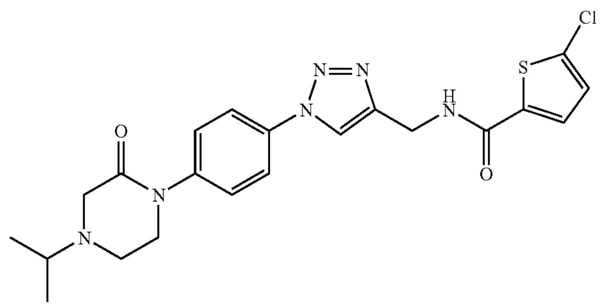 | 5-Chloro-N-((1-(4-(4-isopropyl-2-oxopiperazin-1-yl)phenyl)-1H-1,2,3-triazol-4-yl)methyl)thiophene-2-carboxamide |
| 86 | 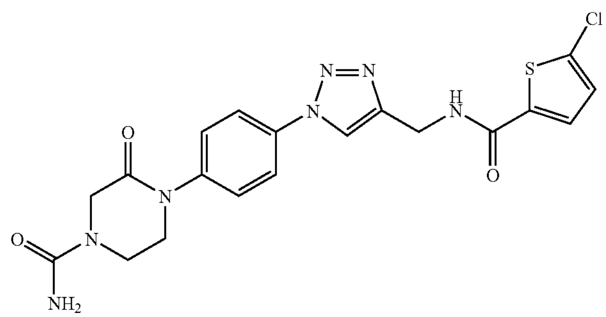 | 4-(4-(4-((5-Chlorothiophene-2-carboxamido)methyl)-1H-1,2,3-triazol-1-yl)phenyl)-3-oxopiperazine-1-carboxamide |
| 87 | 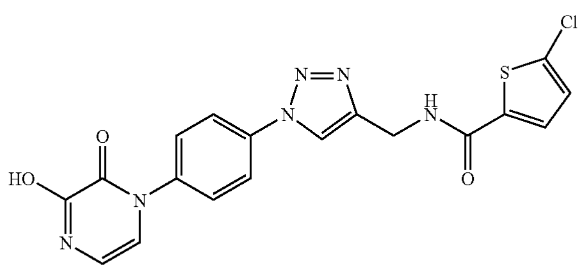 | 5-Chloro-N-((1-(4-(3-hydroxy-2-oxopyrazin-1(2H)-yl)phenyl)-1H-1,2,3-triazol-4-yl)methyl)thiophene-2-carboxamide |
| 88 | 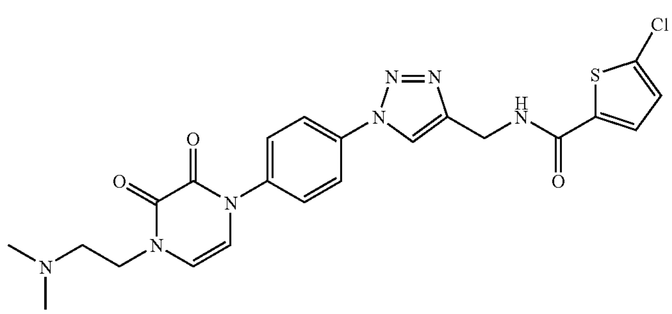 | 5-Chloro-N-((1-(4-(4-(2-(dimethylamino)ethyl)-2,3-dioxo-3,4-dihydropyrazin-1(2H)-yl)phenyl)-1H-1,2,3-triazol-4-yl)methyl)thiophene-2-carboxamide |
| 89 | 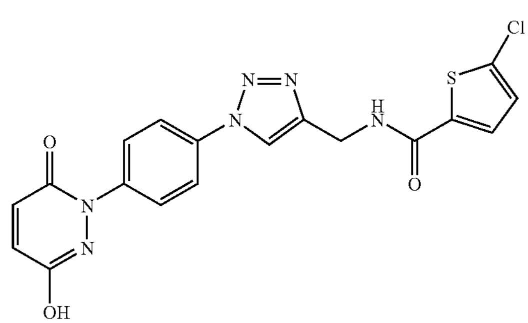 | 5-Chloro-N-((1-(4-(3-hydroxy-6-oxopyridazin-1(6H)-yl)phenyl)-1H-1,2,3-triazol-4-yl)methyl)thiophene-2-carboxamide |

TABLE 1-continued

| Compound | Structure | Name |
| --- | --- | --- |
| 90 | 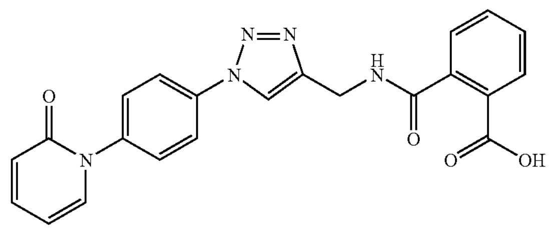 | 2-((1-(4-(2-Oxopyridin-1(2H)-yl)phenyl)-1H-1,2,3-triazol-4-yl)methylcarbamoyl)benzoic acid |
| 91 | 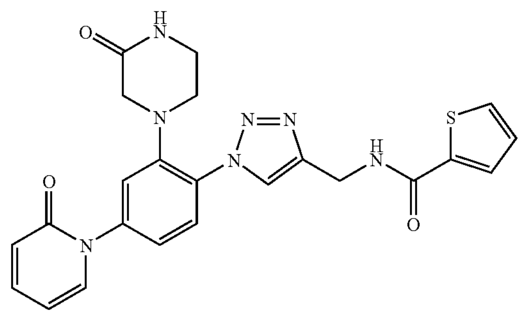 | N-((1-(2-(3-Oxopiperazin-1-yl)-4-(2-oxopyridin-1(2H)-yl)phenyl)-1H-1,2,3-triazol-4-yl)methyl)thiophene-2-carboxamide |
| 92 | 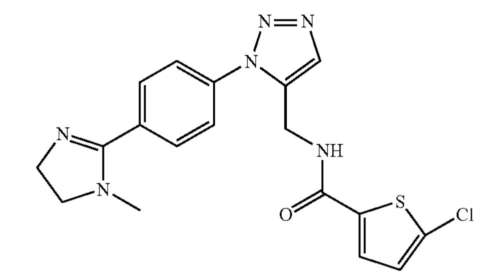 | 5-Chloro-N-((1-(4-(1-methyl-4,5-dihydro-1H-imidazol-2-yl)phenyl)-1H-1,2,3-triazol-5-yl)methyl)thiophene-2-carboxamide |
| 93 | 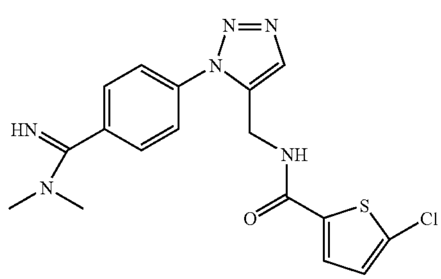 | 5-Chloro-N-((1-(4-(N,N-dimethylcarbamimidoyl)phenyl)-1H-1,2,3-triazol-5-yl)methyl)thiophene-2-carboxamide |
| 94 | 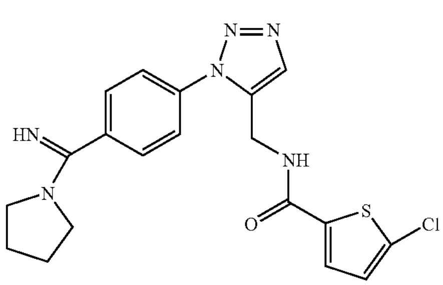 | 5-Chloro-N-((1-(4-(imino(pyrrolidin-1-yl)methyl)phenyl)-1H-1,2,3-triazol-5-yl)methyl)thiophene-2-carboxamide |

TABLE 1-continued

| Compound | Structure | Name |
|---|---|---|
| 95 | 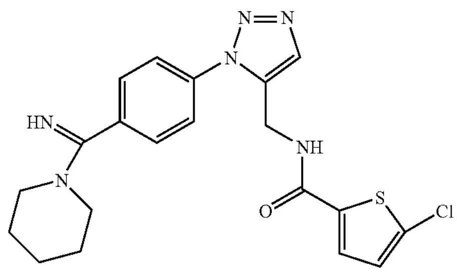 | 5-Chloro-N-((1-(4-(imino(piperidin-1-yl)methyl)phenyl)-1H-1,2,3-triazol-5-yl)methyl)thiophene-2-carboxamide |
| 96 | 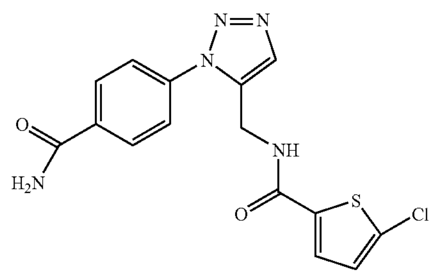 | N-((1-(4-Carbamoylphenyl)-1H-1,2,3-triazol-5-yl)methyl)-5-chlorothiophene-2-carboxamide |
| 97 | 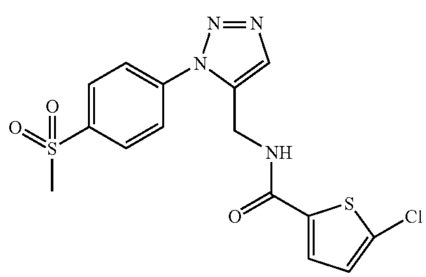 | 5-Chloro-N-((1-(4-(methylsulfonyl)phenyl)-1H-1,2,3-triazol-5-yl)methyl)thiophene-2-carboxamide |
| 98 | 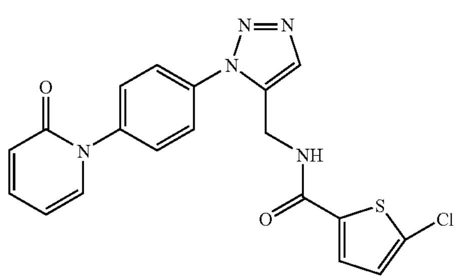 | 5-Chloro-N-((1-(4-(2-oxopyridin-1(2H)-yl)phenyl)-1H-1,2,3-triazol-5-yl)methyl)thiophene-2-carboxamide |
| 99 | 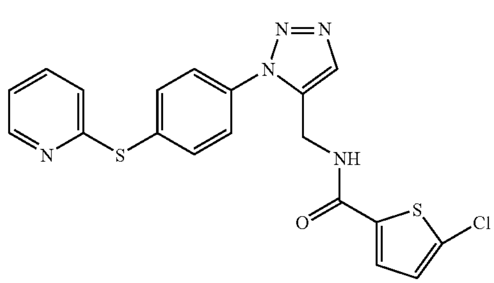 | 5-Chloro-N-((1-(4-(pyridin-2-ylthio)phenyl)-1H-1,2,3-triazol-5-yl)methyl)thiophene-2-carboxamide |

TABLE 1-continued

| Compound | Structure | Name |
| --- | --- | --- |
| 100 | 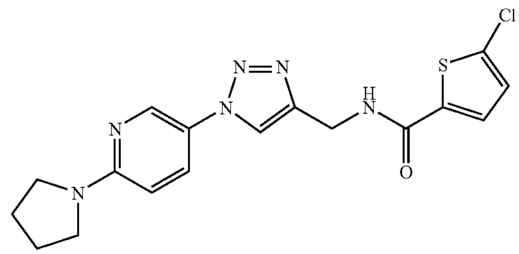 | 5-Chloro-N-((1-(6-(pyrrolidin-1-yl)pyridin-3-yl)-1H-1,2,3-triazol-4-yl)methyl)thiophene-2-carboxamide |
| 101 | 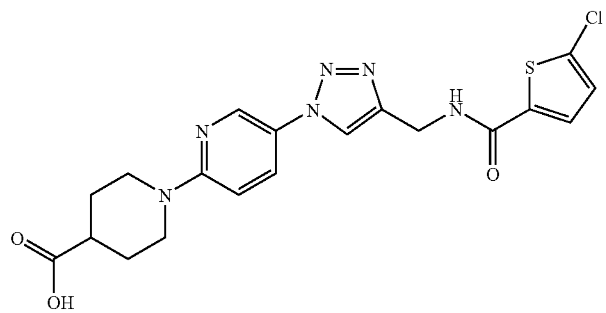 | 1-(5-(4-((5-Chlorothiophene-2-carboxamido)methyl)-1H-1,2,3-triazol-1-yl)pyridin-2-yl)piperidine-4-carboxylic acid |
| 102 | 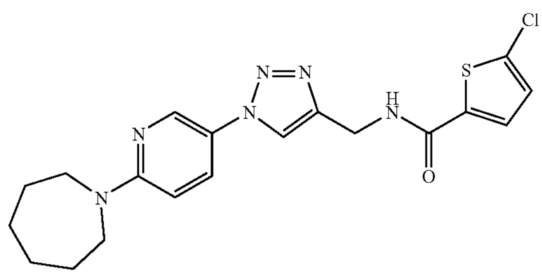 | N-((1-(6-(Azepan-1-yl)pyridin-3-yl)-1H-1,2,3-triazol-4-yl)methyl)-5-chlorothiophene-2-carboxamide |
| 103 | 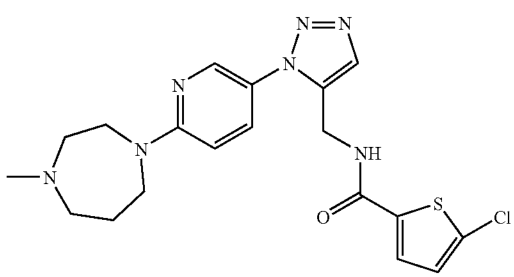 | 5-Chloro-N-((1-(6-(4-methyl-1,4-diazepan-1-yl)pyridin-3-yl)-1H-1,2,3-triazol-5-yl)methyl)thiophene-2-carboxamide |
| 104 | 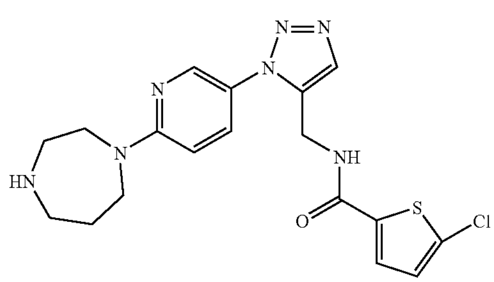 | N-((1-(6-(1,4-Diazepan-1-yl)pyridin-3-yl)-1H-1,2,3-triazol-5-yl)methyl)-5-chlorothiophene-2-carboxamide |

TABLE 1-continued

| Compound | Structure | Name |
|---|---|---|
| 105 | 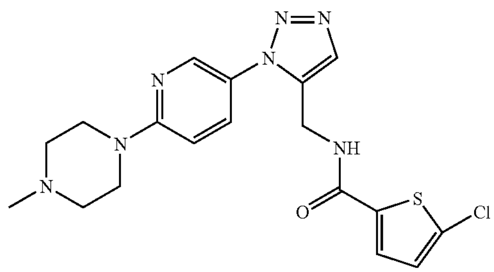 | 5-Chloro-N-((1-(6-(4-methylpiperazin-1-yl)pyridin-3-yl)-1H-1,2,3-triazol-5-yl)methyl)thiophene-2-carboxamide |
| 106 | 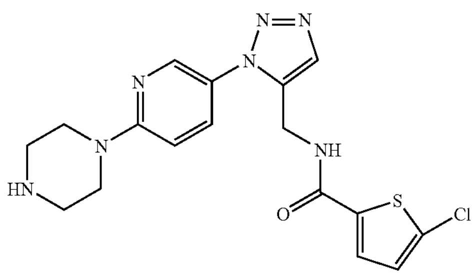 | 5-Chloro-N-((1-(6-(piperazin-1-yl)pyridin-3-yl)-1H-1,2,3-triazol-5-yl)methyl)thiophene-2-carboxamide |
| 107 | 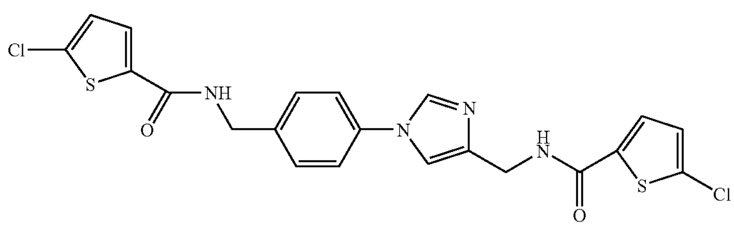 | 5-Chloro-N-(4-(4-((5-chlorothiophene-2-carboxamido)methyl)-1H-imidazol-1-yl)benzyl)thiophene-2-carboxamide |
| 108 | 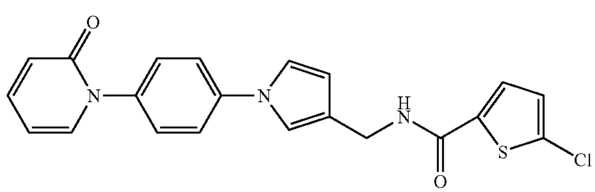 | 5-Chloro-N-((1-(4-(2-oxopyridin-1(2H)-yl)phenyl)-1H-pyrrol-3-yl)methyl)thiophene-2-carboxamide |
| 109 | 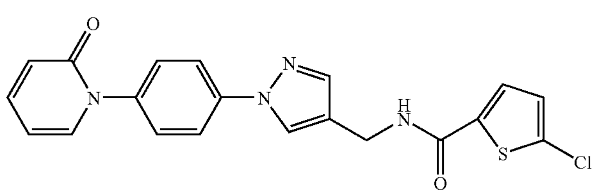 | 5-Chloro-N-((1-(4-(2-oxopyridin-1(2H)-yl)phenyl)-1H-pyrazol-4-yl)methyl)thiophene-2-carboxamide |
| 110 | 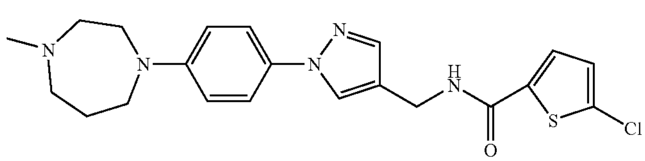 | 5-Chloro-N-((1-(4-(4-methyl-1,4-diazepan-1-yl)phenyl)-1H-pyrazol-4-yl)methyl)thiophene-2-carboxamide |
| 111 | 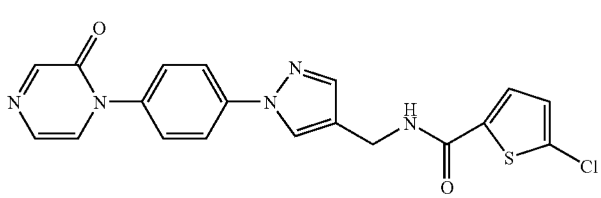 | 5-Chloro-N-((1-(4-(2-oxopyrazin-1(2H)-yl)phenyl)-1H-pyrazol-4-yl)methyl)thiophene-2-carboxamide |

TABLE 1-continued

| Compound | Structure | Name |
|---|---|---|
| 112 | 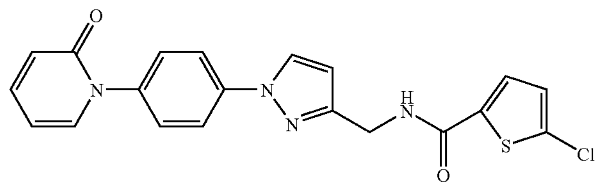 | 5-Chloro-N-((1-(4-(2-oxopyridin-1(2H)-yl)phenyl)-1H-pyrazol-3-yl)methyl)thiophene-2-carboxamide |
| 113 | 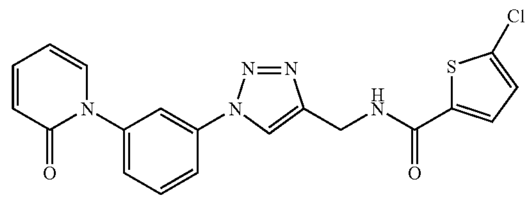 | 5-Chloro-N-((1-(3-(2-oxopyridin-1(2H)-yl)phenyl)-1H-1,2,3-triazol-4-yl)methyl)thiophene-2-carboxamide |
| 114 | 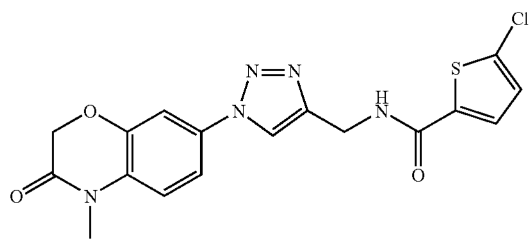 | 5-Chloro-N-((1-(4-methyl-3-oxo-3,4-dihydro-2H-benzo[β][1,4]oxazin-7-yl)-1H-1,2,3-triazol-4-yl)methyl)thiophene-2-carboxamide |
| 115 | 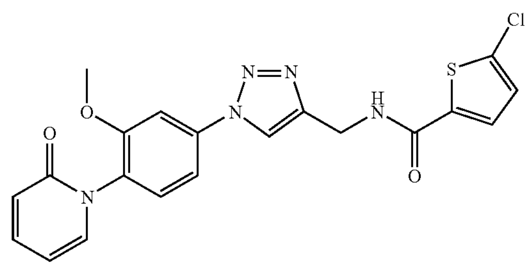 | 5-Chloro-N-((1-(3-methoxy-4-(2-oxopyridin-1(2H)-yl)phenyl)-1H-1,2,3-triazol-4-yl)methyl)thiophene-2-carboxamide |
| 116 | 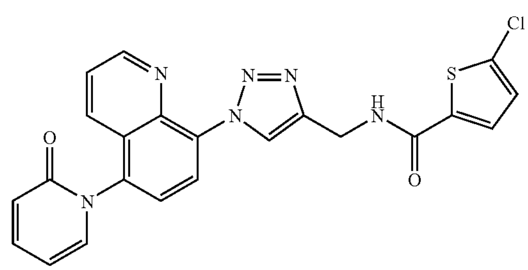 | 5-Chloro-N-((1-(5-(2-oxopyridin-1(2H)-yl)quinolin-8-yl)-1H-1,2,3-triazol-4-yl)methyl)thiophene-2-carboxamide |

All the preferred, more preferred, and most preferred compounds listed above are selective inhibitors of Factor Xa.

Compositions

The present invention further provides compositions comprising one or more compounds of Formula (I) or a pharmaceutically acceptable salt, ester, or prodrug thereof and a pharmaceutically acceptable excipient or carrier. It will be appreciated that the compounds of Formula (I) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of Formula (I), similar to metabolically labile esters or carbamates, which are capable of producing the parent compounds of Formula (I) in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

Pharmaceutically acceptable excipients or carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be in any orally acceptable dosage form, including capsules, tablets, aqueous suspensions or solutions. In the case of tablets for oral use, excipients or carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

The pharmaceutical compositions of this invention may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

Any of the above dosage forms containing effective amounts are within the bounds of routine experimentation and within the scope of the invention. A therapeutically effective dose may vary depending upon the route of administration and dosage form. The preferred compound or compounds of the invention is a formulation that exhibits a high therapeutic index. The therapeutic index is the dose ratio between toxic and therapeutic affects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

Methods of Use

The invention provides methods of inhibiting or decreasing Factor Xa activity as well as treating or ameliorating a Factor Xa associated state, symptom, disorder or disease in a patient in need thereof (e.g., human or non-human). "Treating" within the context of the invention means an alleviation of symptoms associated with a disorder or disease, or halt of further progression or worsening of those symptoms, or prevention or prophylaxis of the disease or disorder.

The term "mammal" includes organisms which express Factor Xa. Examples of mammals include mice, rats, cows, sheep, pigs, goats, horses, bears, monkeys, dogs, cats and, preferably, humans. Transgenic organisms which express Factor Xa are also included in this definition.

The inventive methods comprise administering an effective amount of a compound or composition described herein to a mammal or non-human animal. As used herein, "effective amount" of a compound or composition of the invention includes those amounts that antagonize or inhibit Factor Xa. An amount which antagonizes or inhibits Factor Xa is detectable, for example, by any assay capable of determining Factor Xa activity, including the one described below as an illustrative testing method. Effective amounts may also include those amounts which alleviate symptoms of a Factor Xa associated disorder treatable by inhibiting Factor Xa. Accordingly, "antagonists of Factor Xa" include compounds which interact with the Factor Xa and modulate, e.g., inhibit or decrease, the ability of a second compound, e.g., another Factor Xa ligand, to interact with the Factor Xa. The Factor Xa binding compounds are preferably antagonists of Factor Xa. The language "Factor Xa binding compound" (e.g., exhibits binding affinity to the receptor) includes those compounds which interact with Factor Xa resulting in modulation of the activity of Factor Xa. Factor Xa binding compounds may be identified using an in vitro (e.g., cell and non-cell based) or in vivo method. A description of an in vitro method is provided below.

The amount of compound present in the methods and compositions described herein should be sufficient to cause a detectable decrease in the severity of the disorder, as measured by any of the assays described in the examples. The amount of Factor Xa modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt or solvate according to the formula I, another therapeutic agent (e.g., methotrexate) or a pharmaceutically acceptable salt or solvate thereof, and a pharmaceutically acceptable excipient or carrier.

The invention comprises a compound having the formula I, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where Factor Xa plays a role.

General Methods

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates may be characterized by high performance liquid chromatography (HPLC) using a Waters Alliance chromatography system with a 2695 Separation Module (Milford, Mass.). The analytical columns may be C-18 SpeedROD RP-18E Columns from Merck KGaA (Darmstadt, Germany). Alternately, characterization may be performed using a Waters Unity (UPLC) system with Waters Acquity UPLC BEH C-18 2.1 mm×15 mm columns. A gradient elution may be used, typically starting with 5% acetonitrile/95% water and progressing to 95% acetonitrile over a period of 5 minutes for the Alliance system and 1 minute for the Acquity system. All solvents may contain 0.1% trifluoroacetic acid (TFA). Compounds may be detected by ultraviolet light (UV) absorption at either 220 or 254 nm. HPLC solvents may be from EMD Chemicals, Inc. (Gibbstown, N.J.). In some instances, purity may be assessed by thin layer chromatography (TLC) using glass backed silica gel plates, such as, for example, EMD Silica Gel 60 2.5 cm×7.5 cm plates. TLC results may be readily detected visually under ultraviolet light, or by employing well known iodine vapor and other various staining techniques.

Mass spectrometric analysis may be performed on one of two Agilent 1100 series LCMS instruments with acetonitrile/water as the mobile phase. One system using TFA as the modifier and measures in positive ion mode (reported as MH+, (M+1) or (M+H)+) and the other may use either formic acid or ammonium acetate and measures in both positive (reported as $MH^+$, (M+1) or $(M+H)^+$) and negative (reported as M−, (M−1) or $(M-H)^-$) ion modes.

Nuclear magnetic resonance (NMR) analysis may be performed on some of the compounds with a Varian 400 MHz NMR (Palo Alto, Calif.). The spectral reference may be either TMS or the known chemical shift of the solvent.

The purity of some of compounds of the invention may be assessed by elemental analysis (Robertson Microlit, Madison N.J.).

Melting points may be determined on a Laboratory Devices Mel-Temp apparatus (Holliston, Mass.).

Preparative separations may be carried out using either an Sq16x or an Sg100c chromatography system and prepackaged silica gel columns all purchased from Teledyne Isco, (Lincoln, Nebr.). Alternately, compounds and intermediates may be purified by flash column chromatography using silica gel (230-400 mesh) packing material, or by HPLC using a C-18 reversed phase column. Typical solvents employed for the Isco systems and flash column chromatography may be dichloromethane, methanol, ethyl acetate, hexane, acetone, aqueous hydroxyamine and triethyl amine. Typical solvents employed for the reverse phase HPLC may be varying concentrations of acetonitrile and water with 0.1% trifluoroacetic acid.

EXAMPLES

The following abbreviations are used throughout the Examples:

μL=microliter
μM=micromolar
AIBN=azobisisobutyronitrile
aq.=aqueous
Boc=tert-butoxycarbonyl
BOP=benzotriazol-1-yloxytris(dimethylamino)-phosphonium hexafluorophosphate
conc.=concentrated
DBU=1,8-diazabicyclo[5.4.0]undec-7-ene
DCM=dichloromethane
DIEA=diisopropylethyl amine
DMF=dimethyl formamide
DMSO=dimethyl sulfoxide
eq.=equivalent
EtOAc=ethyl acetate
g=gram
h or hr(s)=hour(s)

HATU=2-(1H-7-azabenzotriazol-1-yl)-1,1,3,3-tetramethyl uronium hexafluorophosphate
HOBt=N-hydroxybenzotriazole
HPLC=high pressure liquid chromatography
IC$_{50}$=the concentration of an inhibitor that is required for 50% inhibition of an enzyme in vitro
kg=kilogram
M=molar
m/z=mass to charge ratio
MeOH=methanol
mg=milligram
MHz=mega Hertz
min=minute
mL=milliliter
mM=millimolar
mm=millimeter
mmol=millimole
mOD/min=millioptical density units per minute
MS=Mass Spec
N=Normal
NaSMe=sodium methylthiolate
NBS=N-bromosuccinamide
nBuOH=n-butanol
ng=nanogram
nM=nanomolar
nm=nanometer
Pd(PPh$_3$)$_4$=tetrakis-(triphenylphosphine)-palladium
PEG=polyethylene glycol
pM=picomolar
PPh$_3$ or Ph$_3$P=triphenyl phosphine
PyBOP=(benzotriazol-1-yloxy)tripyrrolidinophosphonium hexafluorophosphate
prep=preparative
Ra—Ni=Rainey Nickel
RT=room temperature
TEA=triethylamine
TFA=trifluoroacetic acid
TMSCI=trimethylsilyl chloride
TLC=thin layer chromatography Example 1

5-Chloro-N-((1-(4-(2-oxopyridin-1(2H)-yl)-2-(piperazin-1-yl)phenyl)-1H-1,2,3-triazol-4-yl)methyl)thiophene-2-carboxamide (1)

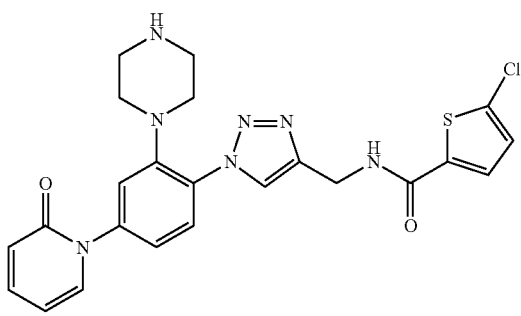

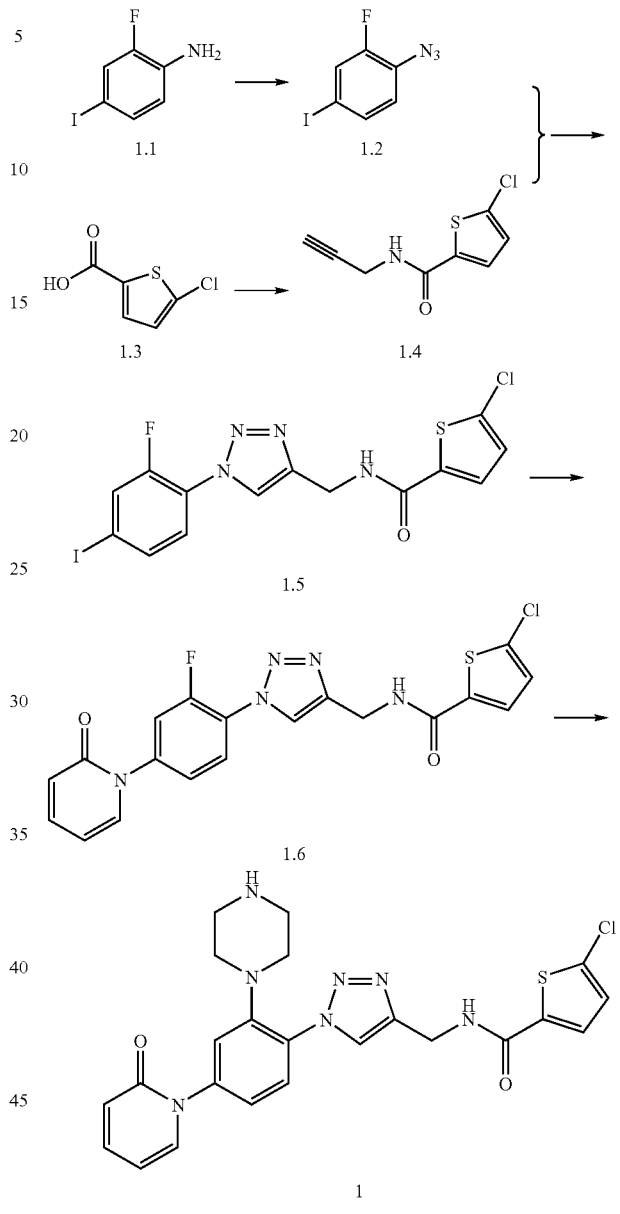

Step 1:

2-Fluoro-4-iodoaniline (1.1, 6.50 g, 27.4 mmol) was dissolved in 25 mL TFA and stirred in ice bath. Solid NaNO$_2$ (2.07 g, 30.1 mmol) was added in small portions. The resulting mixture was stirred for 30 min in ice bath. Sodium azide (1.87 g, 28.8 mmol) was dissolved in 10 mL water and chilled in ice bath. This cold solution was then added to the TFA solution in three portions. The mixture was stirred in ice bath for 1 hr and concentrated in vacuo to remove TFA. The residue was taken into 600 mL DCM and washed with water three times. The organic phase was dried using MgSO$_4$ and concentrated in vacuo to afford 1-azido-2-fluoro-4-iodobenzene 1.2 as a brownish waxy solid in >99% yield. In the mean time, 5-chlorothiophene-2-carboxylic acid (1.3, 9.13 g, 56 mmol) was dissolved in 200 mL dry DCM along with 0.5 mL dry DMF. To the vigorously stirred solution was carefully added oxalyl chlororide (14.7 mL, 169 mmol) dropwise. The resulting solution was stirred for 3 hrs at RT and concentrated in vacuo. The residue was pumped to dryness and then dissolved in 300 mL dry DCM. To this solution was added propargylamine (5.8 mL, 84 mmol) dropwise. The mixture was stirred at RT overnight during which time solid precipitated out. 600 mL hexane was added and the mixture was vigorously stirred for a few hours. The solid was collected by filtration and washed with hexane to give 5-chloro-N-(prop-2-ynyl)thiophene-2-carboxamide 1.4 (9.47 g, 85%) which was used directly without further purification. MS found for $C_8H_6ClNOS$ as (M+H)+ 200.0, 202.0 (chlorine pattern).

Step 2:

To a solution of the aryl azide 1.2 (27 mmol) and alkyne 1.4 (5.37 g, 27 mmol) in 500 mL dry methanol, were added DBU (4.00 mL, 54 mmol) and CuI (5.13 g, 27 mmol). The mixture was stirred at RT overnight. The mixture was diluted with 1.0 liter acetonitrile and stirred vigorously for 1 hr. It was filtered through celite and the filtrate was concentrated and purified using flash column to give compound 1.5 (8.30 g, 67%). MS found for 1.5 $C_{14}H_9ClFIN_4OS$ as (M+H)+ 463.0, 465.0 (Cl pattern).

Step 3:

To a solution of aryl iodide 1.5 (100 mg, 0.22 mmol) and 2-hydroxypyridine (42 mg, 0.44 mmol) in 5 mL dry DMSO in a sealed tube, were added 8-hydroxyquinoline (10 mg, 0.007 mmol), CuI (13 mg, 0.07 mmol) and $Cs_2CO_3$ (145 mg, 0.44 mmol). The mixture was stirred in 120° C. bath for overnight. It was then filtered and the filtrate was directly subjected to reverse phase preparative HPLC to isolate the compound 1.6 (66 mg) as a white powder in 68% yield after lyophilization. MS found for $C_{19}H_{13}ClFN_5O_2S$ as (M+H)+ 430.0, 432.0 (Cl pattern).

Step 4:

To a solution of compound 1.6 (100 mg, 0.23 mmol) in 1 mL anhydrous DMSO in a sealed tube was added 500 mg piperazine. The mixture was stirred in 140° C. bath overnight. It was cooled to RT, and directly subjected to reverse phase HPLC to isolate the title compound as a white powder after lyophilization. MS found for $C_{23}H_{22}ClN_7O_2S$ (M+H)+ 496.1, 498.1 (Cl pattern).

Example 2

5-Chloro-N-((1-(2-(4-ethylpiperazin-1-yl)-4-(2-oxopyridin-1(2H)-yl)phenyl)-1H-1,2,3-triazol-4-yl)methyl)thiophene-2-carboxamide (2)

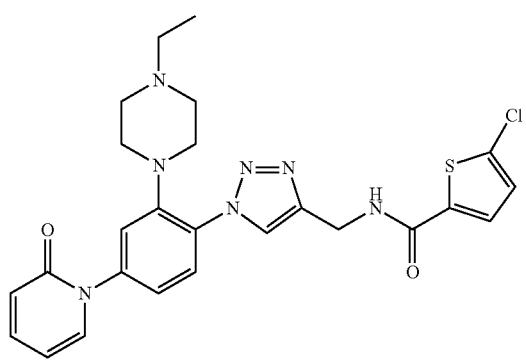

The title compound was prepared using conditions similar to those described in Example 1. MS found for $C_{25}H_{26}ClN_7O_2S$ (M+H)+ 524.1, 526.1 (Cl pattern).

Example 3

5-Chloro-N-((1-(2-(4-isopropylpiperazin-1-yl)-4-(2-oxopyridin-1(2H)-yl)phenyl)-1H-1,2,3-triazol-4-yl)methyl)thiophene-2-carboxamide (3)

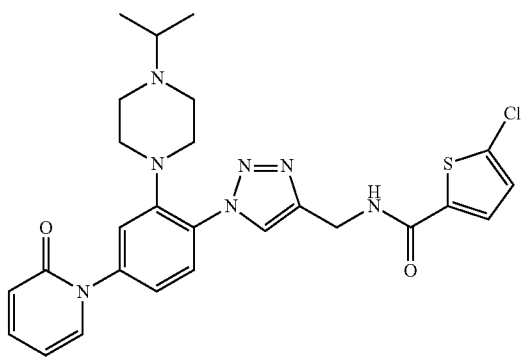

The title compound was prepared using conditions similar to those described in Example 1. MS found for $C_{26}H_{28}ClN_7O_2S$ (M+H)+ 538.1, 540.1 (Cl pattern).

Example 4

5-Chloro-N-((1-(4-(2-oxopyrimidin-1(2H)-yl)phenyl)-1H-1,2,3-triazol-4-yl)methyl)thiophene-2-carboxamide (4)

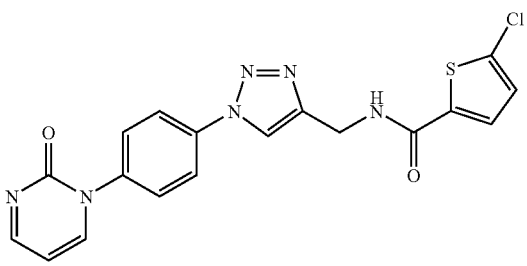

SCHEME 2

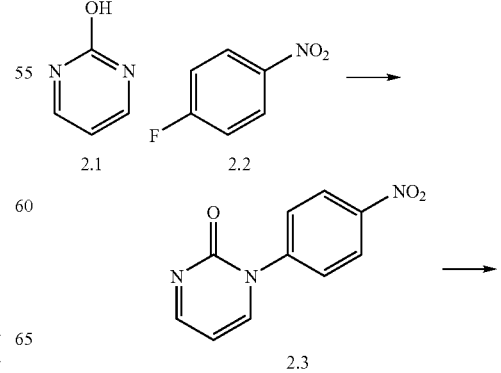

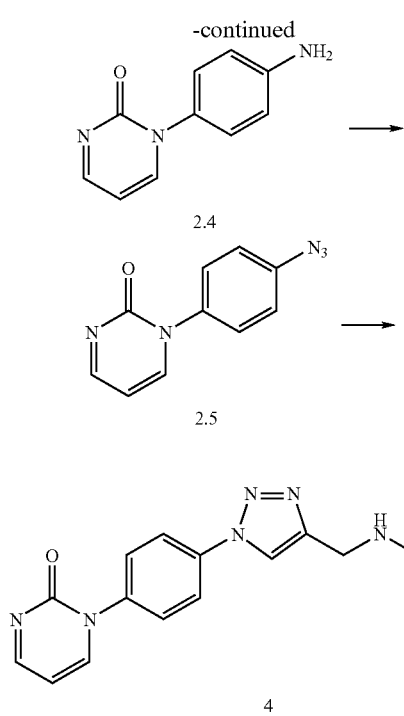

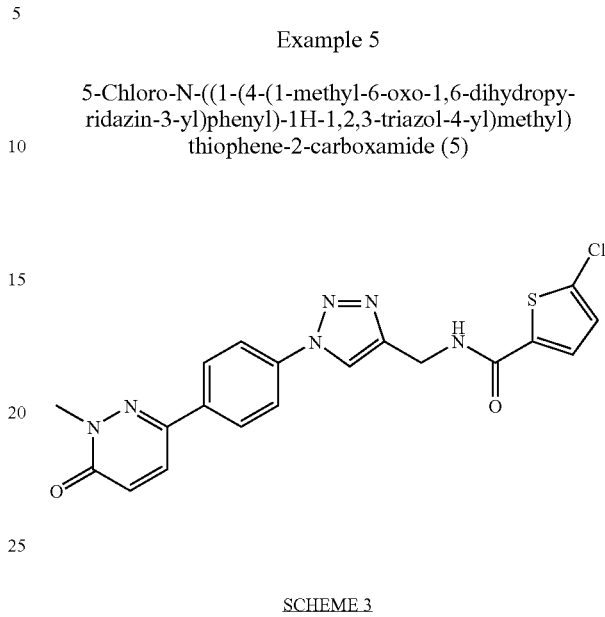

Step 1:

2-Hydroxypyrimidine hydrogenchloride (2.1, 1.50 g, 11.3 mmol) was stirred in 20 mL dry NMP at RT. To it was added sodium hydride (60% in mineral oil, 0.95 g, 23.5 mmol) in small portions carefully. The mixture was stirred for 30 min before 4-fluoro-1-nitrobenzene (1.0 mL, 9.4 mmol) was added. The mixture was sent to 80° C. bath and stirred overnight. It was concentrated in vacuo and taken into acetonitrile. After vigorously stirring, the insoluble solid was collected, which was a mixture of leftover 2-hydroxypyrimidine and 1-(4-nitrophenyl)pyrimidin-2(1H)-one 2.2. MS found for $C_{10}H_7N_3O_3$ (M+H)+ 218.0. This solid (1.27 g, 5.8 mmol) was dissolved in 100 mL ethanol and 30 mL water. To it was added ammonium chloride (3.1 g, 58 mmol) and indium powder (2.6 g, 23 mmol). The mixture was refluxed for 6 hrs. It was concentrated in vacuo, filtered through celite. The solid cake was rinsed with water. The filtrate was concentrated and subjected to reverse phase prep HPLC to isolate 1-(4-aminophenyl)pyrimidin-2(1H)-one 2.3. MS found for $C_{10}H_9N_3O$ (M+H)+ 188.1.

Step 2:

1-(4-Aminophenyl)pyrimidin-2(1H)-one (2.3, 250 mg, 1.3 mmol) was dissolved in 10 mL TFA and stirred in ice bath. To it was added sodium nitrite (95 mg, 1.3 mmol) in small portions. The mixture was stirred in ice bath for 30 min. Sodium azide (260 mg, 4.0 mmol) was dissolved in 2 mL water and chilled in ice bath and added to the reaction mixture. The mixture was stirred for 2 hrs and directly subjected to reverse phase prep HPLC to isolate 1-(4-azidophenyl)pyrimidin-2(1H)-one 2.4. MS found for $C_{10}H_7N_5O$ (M+H)+ 214.1.

Step 3:

1-(4-Azidophenyl)pyrimidin-2(1H)-one (2.4, 20 mg, 0.09 mmol) was dissolved in 5 mL methanol. To it were added 5-chloro-N-(prop-2-ynyl)thiophene-2-carboxamide (compound 1.4, 18 mg, 0.09 mmol), DBU (26 µL, 0.18 mmol) and CuI (17 mg, 0.09 mmol). The mixture was stirred for 2 hrs at RT, diluted with 30 mL acetonitrile, filtered through celite, concentrated in vacuo and subjected to prep HPLC to isolate the title compound. MS found for $C_{18}H_{13}ClN_6O_2S$ (M+H)+ 413.0, 415.0 (Cl pattern).

Example 5

5-Chloro-N-((1-(4-(1-methyl-6-oxo-1,6-dihydropyridazin-3-yl)phenyl)-1H-1,2,3-triazol-4-yl)methyl)thiophene-2-carboxamide (5)

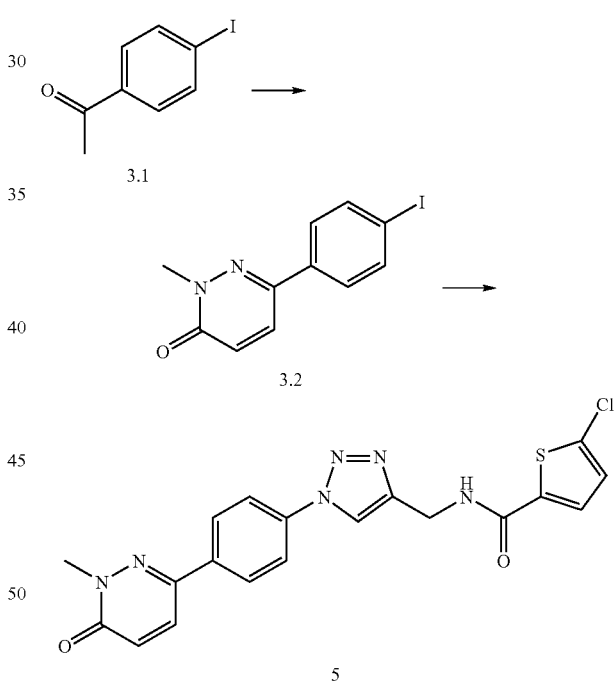

SCHEME 3

Step 1:

The mixture of 4-iodoacetophenone (3.1, 1.00 g, 4.06 mmol) and glyoxalic acid monohydrate (0.45 g, 4.9 mmol) in 20 mL acetic acid was refluxed for 18 hrs and concentrated in vacuo. The dry residue was then stirred in 15 mL water to get a slurry material. To it was added carefully ammonium hydroxide (30%) until pH=9 as indicated by pH paper. The pH was critical for this reaction. Methylhydrazine (0.43 mL) was added, and the mixture was sent to 100° C. bath for 3 hrs. Reaction mixture was diluted with ethyl acetate. The organic phase was washed with brine, dried, concentrated in vacuo, and purified by flash column using 5% methanol in DCM isocratically to yield compound 3.2 (680 mg, 54%). MS found for $C_{11}H_9IN_2O$ (M+H)+ 313.0.

Step 2:

Compound 3.2 (51 mg, 0.16 mmol), 5-chloro-N-(prop-2-ynyl)thiophene-2-carboxamide (compound 1.4, 36 mg, 0.18 mmol), L-proline (8 mg, 0.06 mmol), sodium carbonate (7 mg, 0.06 mmol), sodium azide (17 mg, 0.24 mmol) and sodium ascorbate (6 mg, 0.03 mmol) were mixed in 2 mL DMSO and 0.2 mL water in a sealed tube at RT. To it was added $CuSO_4.5H_2O$ (8 mg, 0.03 mmol). The mixture was stirred in 70° C. bath overnight. Reaction was about 70% complete. The title compound was isolated through direct reverse phase prep HPLC. MS found for $C_{19}H_{15}ClN_6O_2S$ (M+H)+ 427.1, 429.1 (Cl pattern).

Example 6

5-Chloro-N-((1-(4-(2,4-dimethoxypyrimidin-5-yl) phenyl)-1H-1,2,3-triazol-4-yl)methyl)thiophene-2-carboxamide (6)

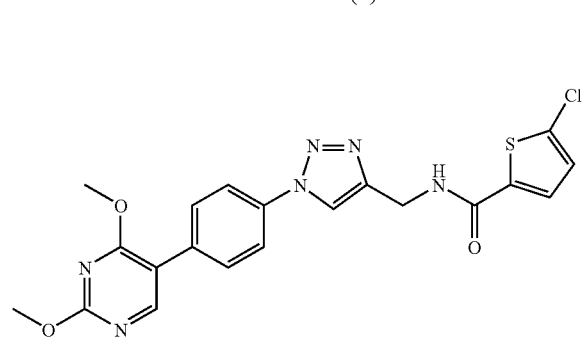

The mixture of 5-chloro-N-((1-(4-iodophenyl)-1H-1,2,3-triazol-4-yl)methyl)thiophene-2-carboxamide (4.1, 48 mg, 0.11 mmol, synthesized by procedures similar to those that were used to make compound 1.5 described in SCHEME 1), 2,4-dimethoxypyrimidin-5-ylboronic acid (4.2, 24 mg, 0.13 mmol), $PdCl_2(PPh_3)_2$ (38 mg, 0.05 mmol), $K_2CO_3$ (23 mg, 0.16 mmol) in 1 mL acetonitrile and 1 mL water was degassed using argon stream and heated in microwave reactor at 125° C. for 15 min. The mixture was filtered and directly subjected to reverse phase prep HPLC to isolate the title compound. MS found for $C_{20}H_{17}ClN_6O_3S$ (M+H)+ 457.1, 459.1 (Cl pattern).

Example 7

5-Chloro-N-((1-(4-(4-methyl-1,4-diazepan-1-yl) phenyl)-1H-1,2,3-triazol-4-yl)methyl)thiophene-2-carboxamide (9)

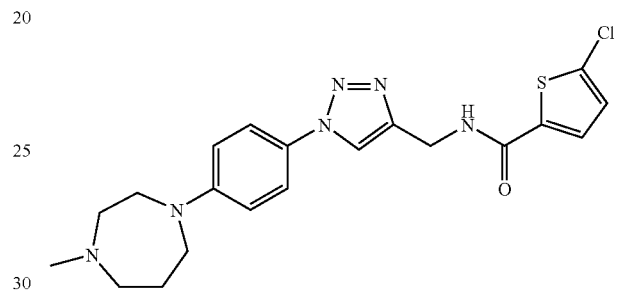

The mixture of 5-chloro-N-((1-(4-iodophenyl)-1H-1,2,3-triazol-4-yl)methyl)thiophene-2-carboxamide (4.1, 100 mg, 0.22 mmol), N-methylhomopiperazine (140 μL, 1.1 mmol),

SCHEME 4

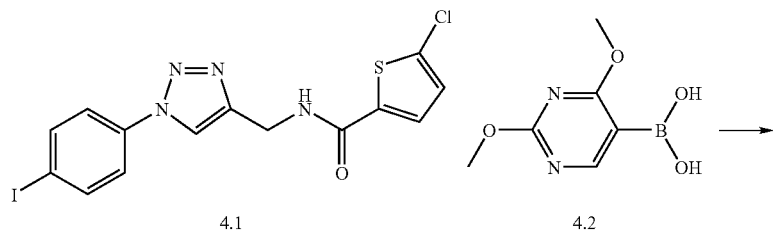

4.1     4.2

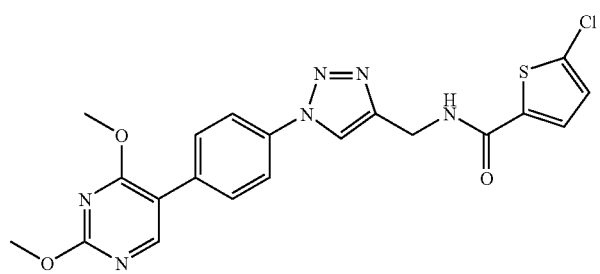

6

CuI (42 mg, 0.22 mmol), ethylene glycol (25 μL, 0.44 mmol), potassium phosphate (93 mg, 0.44 mmol) in 2 mL isopropanol in a sealed tube was stirred for 16 hrs at 120° C. The title compound was isolated directly from the reaction mixture using reverse phase prep HPLC. MS found for $C_{20}H_{23}ClN_6OS$ (M+H)+ 431.1, 433.1 (Cl pattern).

Example 8

5-Chloro-N-((1-(2'-methoxybiphenyl-4-yl)-1H-1,2,3-triazol-4-yl)methyl)thiophene-2-carboxamide (11)

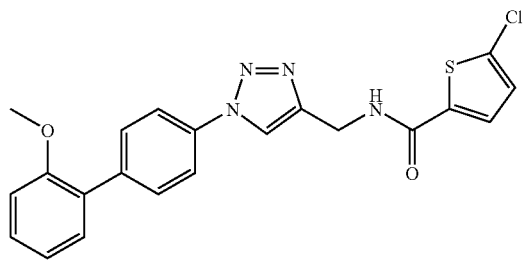

The title compound was prepared according to a procedure similar to that described in Example 6. MS found for $C_{21}H_{17}ClN_4O_2S$ (M+H)+ 425.1, 427.1 (Cl pattern).

Example 9

5-Chloro-N-((1-(2'-hydroxybiphenyl-4-yl)-1H-1,2,3-triazol-4-yl)methyl)thiophene-2-carboxamide (12)

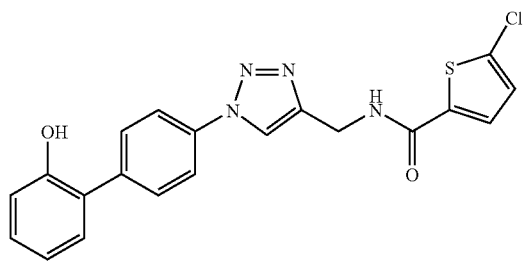

The title compound was prepared according to a procedure similar to that described in Example 6. MS found for $C_{20}H_{15}ClN_4O_2S$ (M+H)+ 411.1, 413.1 (Cl pattern).

Example 10

5-Chloro-N-((1-(2'-(trifluoromethoxy)biphenyl-4-yl)-1H-1,2,3-triazol-4-yl)methyl)thiophene-2-carboxamide (13)

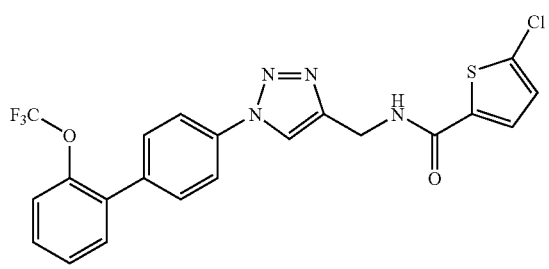

The title compound was prepared according to a procedure similar to that described in Example 6. MS found for $C_{21}H_{14}ClF_3N_4O_2S$ (M+H)+ 479.0, 481.0 (Cl pattern).

Example 11

5-Chloro-N-((1-(4-(6-chloropyridin-3-yl)phenyl)-1H-1,2,3-triazol-4-yl)methyl)thiophene-2-carboxamide (14)

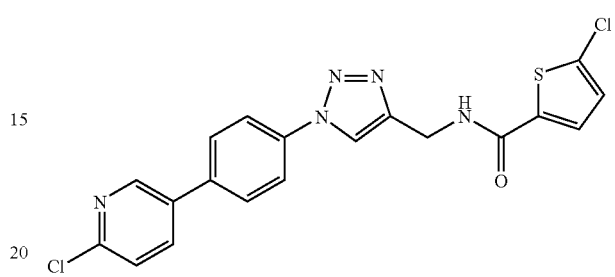

The title compound was prepared according to a procedure similar to that described in Example 6. MS found for $C_{19}H_{13}Cl_2N_5OS$ (M+H)+ 430.0, 432.0 (Cl pattern).

Example 12

5-Chloro-N-((1-(4-(pyrrolidine-1-carbonyl)phenyl)-1H-1,2,3-triazol-4-yl)methyl)thiophene-2-carboxamide (18)

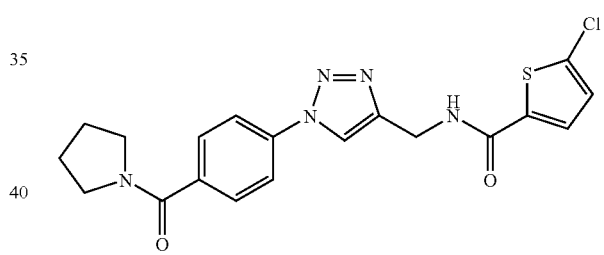

The title compound was prepared according to a procedure similar to that described in Example 1 using the corresponding substituted aniline. MS found for $C_{19}H_{18}ClN_5O_2S$ (M+H)+ 416.0, 418.0 (Cl pattern).

Example 13

5-Chloro-N-((1-(4-(2,5-dihydro-1H-pyrrole-1-carbonyl)phenyl)-1H-1,2,3-triazol-4-yl)methyl)thiophene-2-carboxamide (19)

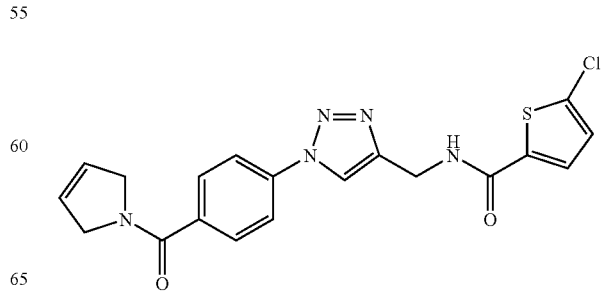

The title compound was prepared according to a procedure similar to that described in Example 1 using the corresponding substituted aniline. MS found for $C_{19}H_{16}ClN_5O_2S$ (M+H)+ 414.0, 416.0 (Cl pattern).

Example 14

N-((1-(4-(2-Amino-N-methylacetamido)phenyl)-1H-1,2,3-triazol-4-yl)methyl)-5-chlorothiophene-2-carboxamide (21)

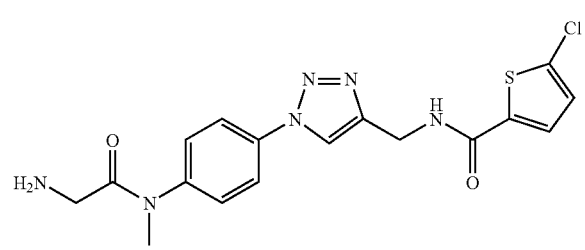

The mixture of 5-chloro-N-((1-(4-iodophenyl)-1H-1,2,3-triazol-4-yl)methyl)thiophene-2-carboxamide (100 mg, 0.22 mmol), H-Gly-NHMe.HCl (110 mg, 0.88 mmol), CuI (42 mg, 0.22 mmol), N,N'-dimethylethylenediamine (24 μL, 0.22 mmol), cesium carbonate (440 mg, 1.4 mmol) in 5 mL dioxane in a sealed tube was stirred for 15 hrs at 120° C. The title compound was isolated directly from the reaction mixture using reverse phase prep HPLC. MS found for $C_{17}H_{17}ClN_6O_2S$ (M+H)+ 405.1, 407.1 (Cl pattern).

Example 15

5-Chloro-N-((1-(4-(N-methylpropionamido)phenyl)-1H-1,2,3-triazol-4-yl)methyl)thiophene-2-carboxamide (24)

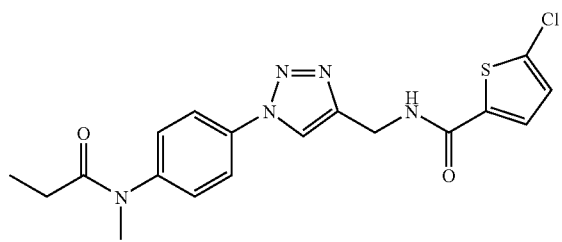

The mixture of 5-chloro-N-((1-(4-iodophenyl)-1H-1,2,3-triazol-4-yl)methyl)thiophene-2-carboxamide (100 mg, 0.22 mmol), $C_2H_5CONHCH_3$ (77 μL, 0.88 mmol), CuI (42 mg, 0.22 mmol), N,N'-dimethylethylenediamine (24 μL, 0.22 mmol), cesium carbonate (290 mg, 0.88 mmol) in 5 mL dioxane in a sealed tube was stirred for 15 hrs at 120° C. The title compound was isolated directly from the reaction mixture using reverse phase prep HPLC. MS found for $C_{18}H_{18}ClN_5O_2S$ (M+H)+ 404.1, 406.1 (Cl pattern).

Example 16

Ethyl 4-(4-((5-chlorothiophene-2-carboxamido)methyl)-1H-1,2,3-triazol-1-yl)phenyl(methyl)carbamate (25)

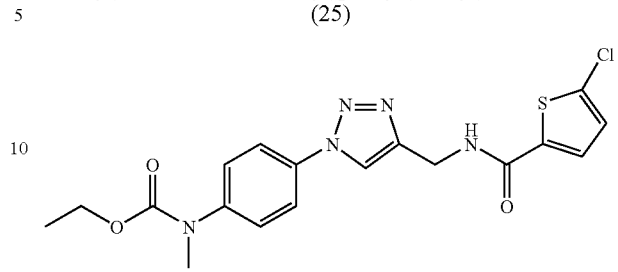

The title compound was prepared using a similar procedure as described in Example 16. MS found for $C_{18}H_{18}ClN_5O_3S$ (M+H)+ 420.1, 422.1 (Cl pattern).

Example 17

5-Chloro-N-((1-(4-(2-methoxy-N-methylacetamido)phenyl)-1H-1,2,3-triazol-4-yl)methyl)thiophene-2-carboxamide (26)

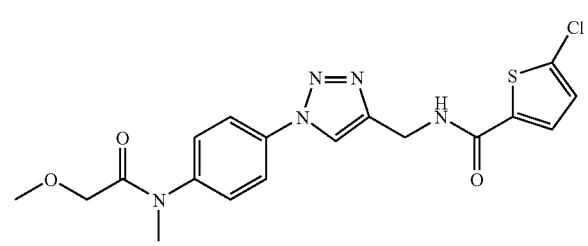

Compound 25 (60 mg, 0.14 mmol) was treated with 2 mL 2N NaOH and 2 mL methanol at 80° C. for 2 hrs and acidified with 2N HCl. The major product in this reaction, 5-chloro-N-((1-(4-(methylamino)phenyl)-1H-1,2,3-triazol-4-yl)methyl)thiophene-2-carboxamide, was isolated with prep HPLC. MS found for $C_{15}H_{14}ClN_5OS$ (M+H)+ 348.1, 350.1. This compound (10 mg, 0.023 mmol) was dissolved in 1 mL DMSO. To it were added 20 μL DIEA and $CH_3OCH_2COCl$ (25 μL, 0.23 mmol). The mixture was stirred for 30 min and directly subjected to prep HPLC to isolate the title compound. MS found for $C_{18}H_{18}ClN_5O_3S$ (M+H)+ 420.1, 422.1 (Cl pattern).

Example 18

5-Chloro-N-((1-(4-(2-(dimethylamino)-N-methylacetamido)phenyl)-1H-1,2,3-triazol-4-yl)methyl)thiophene-2-carboxamide (27)

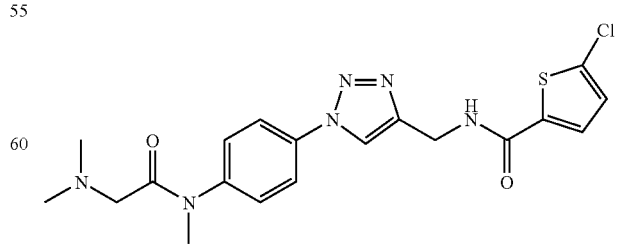

5-Chloro-N-((1-(4-(methylamino)phenyl)-1H-1,2,3-triazol-4-yl)methyl)thiophene-2-carboxamide (34 mg, 0.1 mmol), prepared as shown in Example 17, was dissolved in 10 mL methanol and treated with MP-carbonate for 1 hr. The mixture was filtered and the filtrate was concentrated in vacuo. The residue was dissolved in 3 mL pyridine and N,N-dimethylglycine (16 mg, 0.1 mmol) was added. The mixture was then stirred in ice bath. POCl$_3$ (28 µL, 0.3 mmol) was added. The reaction was stirred for 20 min and quenched with methanol. The mixture was concentrated and directly subjected to prep HPLC to isolate the title compound. MS found for $C_{19}H_{21}ClN_6O_2S$ (M+H)+ 433.1, 435.1 (Cl pattern).

Example 19

5-Chloro-N-((1-(4-(N-methylacetamido)phenyl)-1H-1,2,3-triazol-4-yl)methyl)thiophene-2-carboxamide (28)

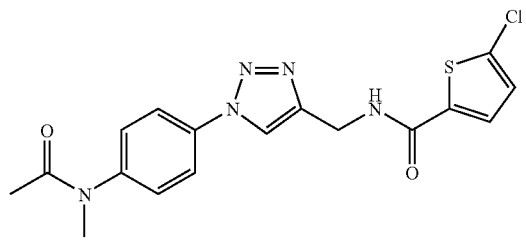

The title compound was prepared using a similar procedure as described in Example 15. MS found for $C_{17}H_{16}ClN_5O_2S$ (M+H)+ 390.1, 392.1 (Cl pattern).

Example 20

5-Chloro-N-((1-(4-(6-oxo-1,6-dihydropyridazin-3-yl)phenyl)-1H-1,2,3-triazol-4-yl)methyl)thiophene-2-carboxamide (30)

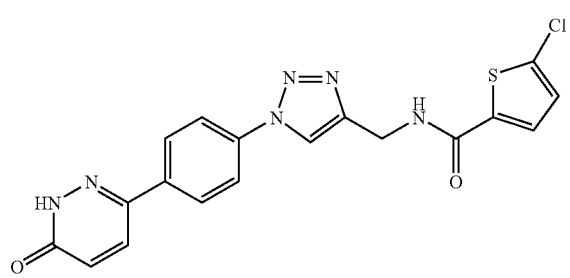

The title compound was prepared according to a procedure similar to that describe in Example 5. MS found for $C_{18}H_{13}ClN_6O_2S$ (M+H)+ 413.1, 415.1 (Cl pattern).

Example 21

5-Chloro-N-((3-(2-fluoro-4-(2-oxopyridin-1(2H)-yl)phenyl)-5-methyl-4,5-dihydroisoxazol-5-yl)methyl)thiophene-2-carboxamide (31)

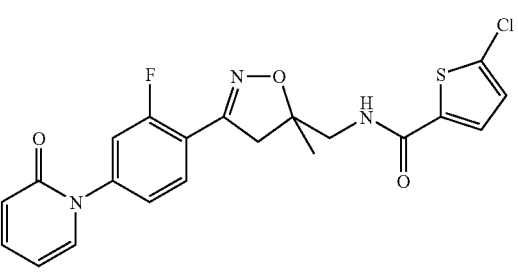

SCHEME 5

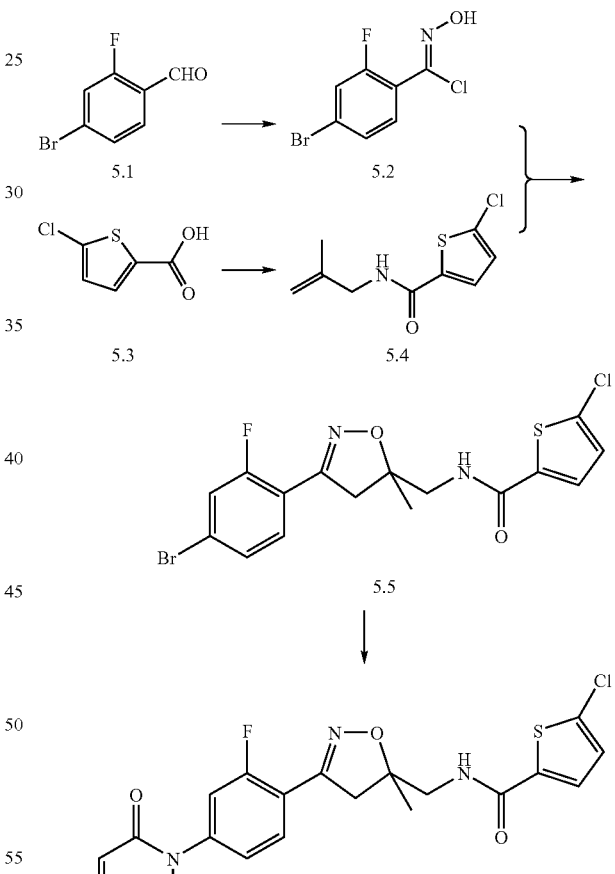

Step 1:

4-Bromo-2-fluorobenzaldehyde (5.1, 6564 g, 32.7 mmol) was stirred in 100 mL ethanol and 100 mL pyridine. To it was added hydroxylamine hydrochloride (2.27 g, 32.7 mmol). The mixture was stirred at RT for 2 hrs. It was concentrated in vacuo to dryness. The residue was then dissolved in 100 mL DMF. To it was added NCS (5.24 g, 39.2 mmol), and the mixture was stirred for 1 day. It was concentrated in vacuo, taken into ethyl acetate, washed with brine twice, dried and concentrated in vacuo to afford compound 5.2 in quantitative yield. MS found for C₇H₄BrClFNO (M+H)+ 252.0, 254.0.

Step 2:

5-Chloro-2-thiophenecarboxylic acid (5.3, 200 mg, 1.23 mmol) was dissolved in 10 mL anhydrous DCM. To it were added 1 drop of DMF and 0.32 mL oxalyl chloride (3.7 mmol). The mixture was stirred at RT for 3 hrs and concentrated in vacuo to dryness. The residue was dissolved in 20 mL anhydrous DCM and 2-methylallylamine (0.3 mL, 3.2 mmol) was added. The mixture was stirred for 30 min at RT, concentrated in vacuo, taken into ethyl acetate, washed with brine three times, dried and concentrated in vacuo to give compound 5.4 (218 mg, 82%). MS found for C₉H₁₀ClNOS (M+H)+ 2160, 218.0 (Cl pattern).

Step 3:

The mixture of compound 5.2 (250 mg, 1.0 mmol), compound 5.4 (218 mg, 1.0 mmol) in 10 mL toluene was heated at 125° C. in a sealed tube for 1 week. The reaction was still incomplete. It was concentrated in vacuo and subjected to flash column to isolate compound 5.5 (58 mg, 13%) using 3% methanol in DCM. MS found for C₁₆H₁₃BrClFN₂O₂S (M+H)+ 431.0, 433.0.

Step 4:

Compound 5.5 (58 mg, 0.13 mmol) was dissolved in 6 mL dioxane and 2 mL DMSO in a sealed tube. To it were added 2-hydroxypyridine (29 mg, 0.30 mmol), N,N'-dimethylethylenediamine (9 μL, 0.08 mmol), K₃PO₄ (58 mg, 0.27 mmol) and CuI (13 mg, 0.07 mmol). The mixture was stirred for 3 days at 130° C. It was concentrated and directly subjected to reverse phase preparative HPLC to isolate the title compound. MS found for C₂₁H₁₇ClFN₃O₃S (M+H)+ 446.1, 448.1 (Cl pattern).

Example 22

5-Chloro-N-((5-oxo-1-(4-(2-oxopyridin-1 (2H)-yl) phenyl)-4,5-dihydro-1H-pyrazol-3-yl)methyl) thiophene-2-carboxamide (32)

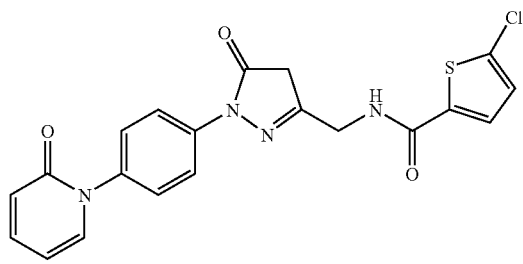

SCHEME 6

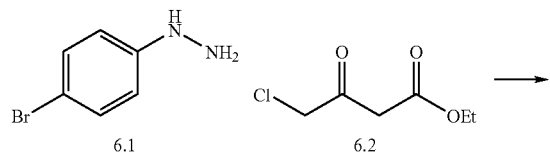

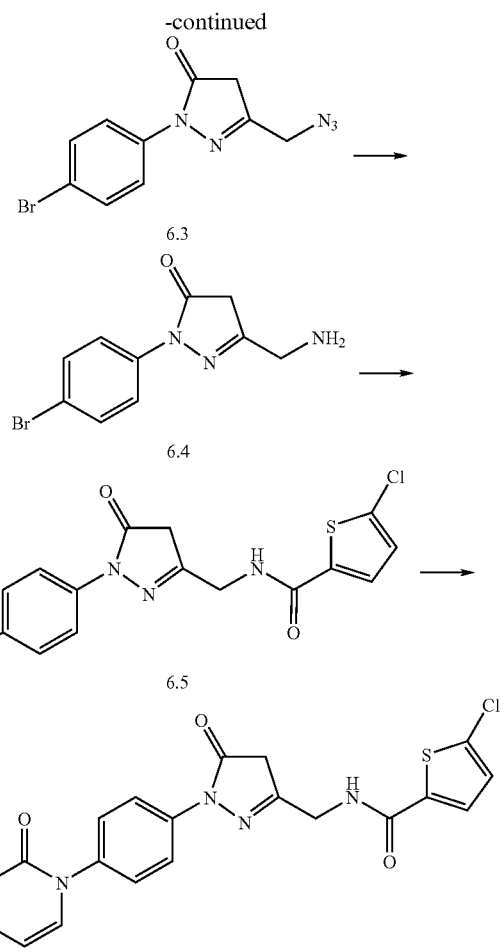

Step 1:

Compound 6.1 hydrochloride (1.77 g, 7.9 mmol) and compound 6.2 (1.30 g, 7.9 mmol) in 50 mL dioxane were stirred in 60° C. bath overnight. The mixture was concentrated, taken into 300 mL ethyl acetate, washed with brine three times, dried, and concentrated in vacuo. The residue was dissolved in 20 mL DMSO and treated with sodium azide (1.04 g, 16 mmol) for 4 hrs. The mixture was diluted with ethyl acetate, washed with brine three times, dried, concentrated and purified using flash column to isolate compound 6.3 (0.79 g, 34%). MS found for C₁₀H₈BrN₅O (M+H)+ 294.0, 296.0 (Br pattern).

Step 2:

Compound 6.3 (0.79 g, 2.7 mmol) was dissolved in 20 mL ethanol and 20 mL acetic acid, and was treated with iron powder (0.70 g, 13.5 mmol) at 100° C. for 30 min. The mixture was diluted with acetonitrile, filtered through a celite bed, concentrated and subjected to reverse phase preparative HPLC to isolate compound 6.4 (40%). MS found for C₁₀H₁₀BrN₃O (M+H)+ 268.0, 270.0 (Br pattern).

Step 3:

Compound 6.4 (120 mg, 0.44 mol) and 5-chloro-2-thiophenecarboxylic acid (110 mg, 0.66 mmol) were dissolved in 15 mL anhydrous DMF. To it were added DIEA (310 μL, 1.76 mmol) and PyBOP (460 mg, 0.88 mmol). The mixture was stirred at RT overnight. It was diluted with ethyl acetate, washed with brine three times, dried, concentrated in vacuo and purified using reverse phase preparative HPLC to isolate compound 6.5 (50%). MS found for $C_{15}H_{11}BrClN_3O_2S$ (M+H)+ 412.0, 414.0.

Step 4:

The title compound was prepared from compound 6.5 using a similar procedure shown in Step 4 in Example 21. MS found for $C_{20}H_{15}ClN_4O_3S$ (M+H)+ 427.1, 429.1 (Cl pattern).

Example 23

5-Chloro-N-((2-oxo-1-(4-(2-oxopyridin-1(2H)-yl)phenyl)-1,2-dihydropyridin-3-yl)methyl)thiophene-2-carboxamide (33)

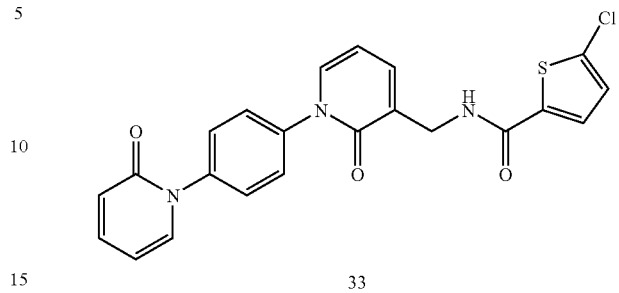

33

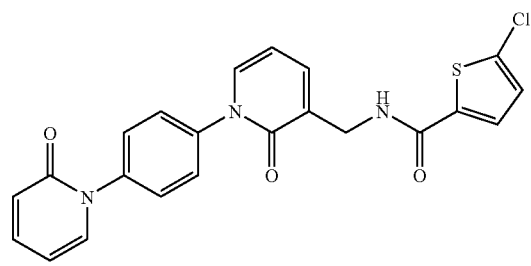

SCHEME 7

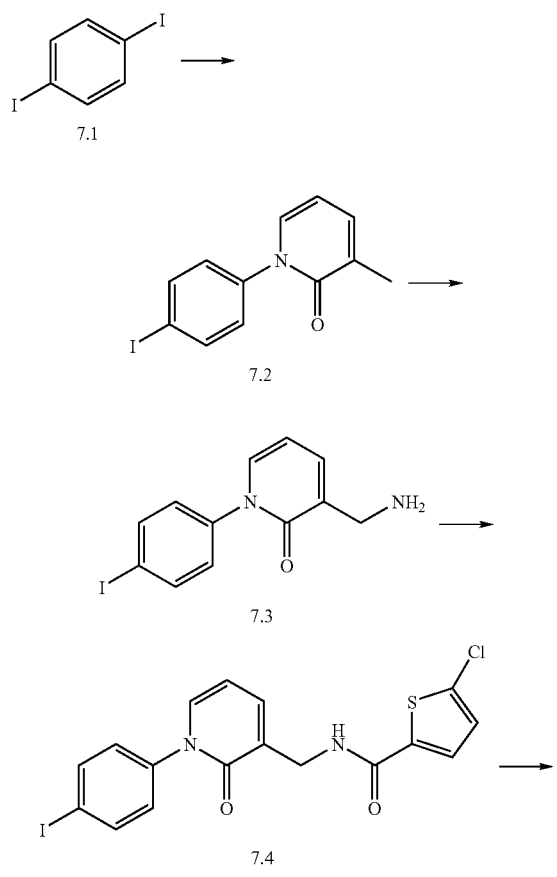

Step 1:

The mixture of 1,4-diiodobenzene (7.1, 1.00 g, 3.0 mmol), 2-hydroxy-3-methylpyridine (0.50 g, 4.5 mmol), 8-hydroxyquinoline (132 mg, 0.9 mmol), $K_2CO_3$ (0.84 g, 6.0 mmol) and CuI (173 mg, 0.9 mmol) in 12 mL DMSO was stirred at 120° C. for 16 hrs in a sealed tube. It was diluted with 300 mL ethyl acetate, washed with brine three times, dried, concentrated and purified using flash column to give compound 7.2 (393 mg, 42%). MS found for $C_{12}H_{10}INO$ (M+H)+ 312.0.

Step 2:

The mixture of compound 7.2 (393 mg, 1.26 mmol), NBS (247 mg, 1.39 mmol) and AIBN (82 mg, 0.50 mmol) in 20 mL carbon tetrachloride was refluxed overnight. It was concentrated, taken into ethyl acetate, washed with brine three times, dried, and concentrated in vacuo to dryness. The residue was dissolved in 5 mL DMSO and treated with sodium azide (200 mg) overnight. It was diluted with ethyl acetate, washed with brine three times, dried and concentrated in vacuo. The residue was then dissolved in 10 mL ethanol and 10 mL acetic acid and treated with iron powder (300 mg) at 100° C. for 30 min. The mixture was diluted with acetonitrile, filtered through a celite bed, concentrated and subjected to reverse phase preparative HPLC to isolate compound 7.3 (20%). MS found for $C_{12}H_{11}IN_2O$ (M+H)+ 327.0.

Step 3:

Compound 7.3 (80 mg, 0.24 mmol) was dissolved in 10 mL DMF. To it were added 5-chloro-2-thiophenecarboxylic acid (60 mg, 0.36 mmol), DIEA (210 µL, 1.2 mmol) and PyBOP (250 mg, 0.48 mmol). The mixture was stirred overnight. It was then diluted with ethyl acetate, washed with brine three times, dried, concentrated and purified by flash column to give compound 7.4 (90%). MS found for $C_{17}H_{12}ClIN_2O_2S$ (M+H)+ 471.0, 473.0.

Step 4:

Compound 7.4 (0.24 mmol) was dissolved in 3 mL DMSO. To it were added 2-hydroxypyridine (68 mg, 0.72 mmol), 8-hydroxyquinoline (10 mg, 0.07 mmol), cesium carbonate (156 mg, 0.48 mmol) and CuI (14 mg, 0.07 mmol). The mixture was stirred at 120° C. for 16 hrs. It was directly subjected to reverse phase preparative HPLC to isolate the title compound. MS found for $C_{22}H_{16}ClN_3O_3S$ (M+H)+ 438.1, 440.1 (Cl pattern).

Example 24

5-Chloro-N-((6-oxo-1-(4-(2-oxopyridin-1(2H)-yl)phenyl)-1,6-dihydropyridin-3-yl)methyl)thiophene-2-carboxamide (34)

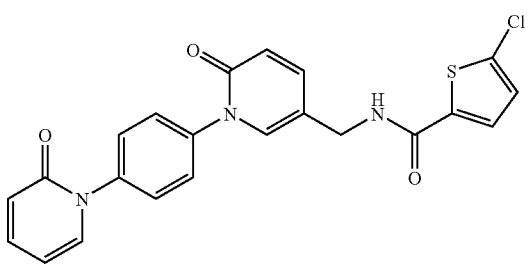

The title compound was prepared according to a procedure similar to that described in Example 23. MS found for $C_{22}H_{16}ClN_3O_3S$ (M+H)+ 438.1, 440.1 (Cl pattern).

Example 25

5-Chloro-N-((1-methyl-2-(4-(2-oxopyridin-1(2H)-yl)phenyl)-1H-imidazol-4-yl)methyl)thiophene-2-carboxamide (35)

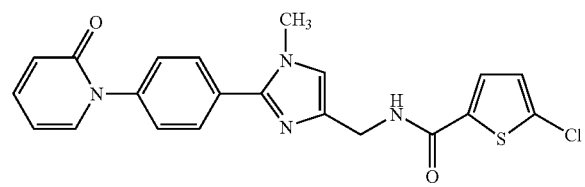

SCHEME 8

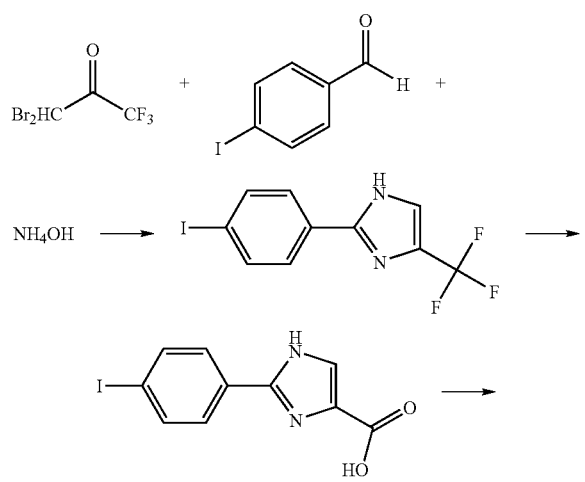

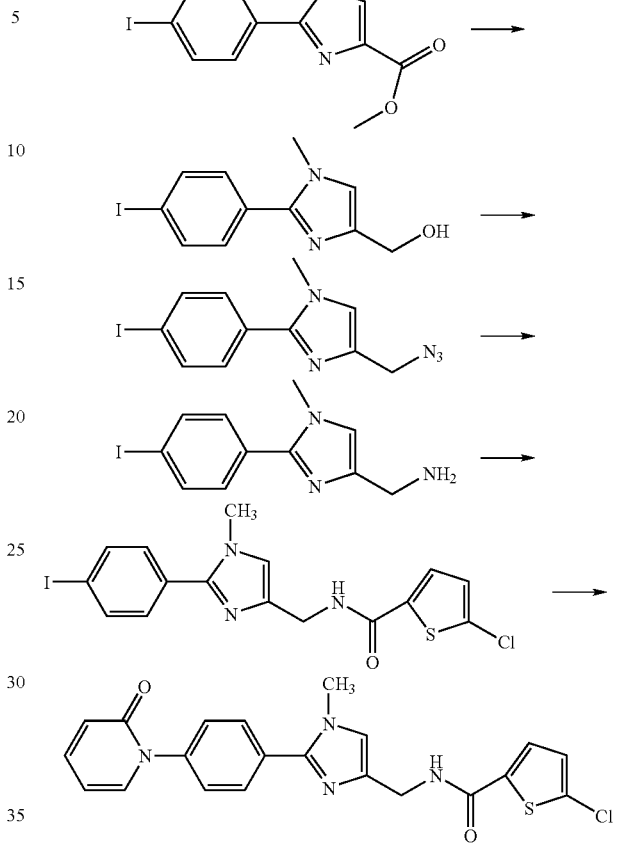

To a solution of potassium acetate (0.860 g, 8.78 mmol) in $H_2O$ (3 mL), 3,3-dibromo-1,1,1-trifluoroacetone (1.10 g, 4.07 mmol) was added. The solution was heated at 100° C. for 30 min. After being cooled to room temperature, a solution of 4-iodobenzaldehyde (0.860 g, 3.71 mmol) in MeOH (4 mL) and THF (4 mL) was added, followed by conc. $NH_4OH$ (8 mL). The mixture was stirred at room temperature overnight. Water and EtOAc were added. The organic layer was separated, dried over $Na_2SO_4$, concentrated in vacuo to give 2-(4-iodophenyl)-4-(trifluoromethyl)-1H-imidazole as a solid (1.34 g).

The mixture of 2-(4-iodophenyl)-4-(trifluoromethyl)-1H-imidazole prepared above (1.34 g) in 5N aq. NaOH (12 mL) was heated at 90° C. for 2 h. It was filtered. The filtrate was neutralized with 6 N HCl carefully to pH 6-7. The product was extracted with nBuOH. The nBuOH solution was then concentrated in vacuo to give 2-(4-iodophenyl)-1H-imidazole-4-carboxylic acid as a solid (0.512 g).

To a mixture of 2-(4-iodophenyl)-1H-imidazole-4-carboxylic acid prepared above (257 mg, 0.818 mmol) and NaH (60% suspension, washed with hexane, 82 mg, 2.1 mmol) in DMF (8 mL) was added iodomethane (0.130 mL, 2.1 mmol). The mixture was heated at 50° C. for 2 h. More iodomethane (0.100 mL) was added to the reaction mixture. After being stirred at 50° C. for an additional 2 h, water and EtOAc were added. The organic layer was separated, dried over $Na_2SO_4$, concentrated in vacuo to give methyl 2-(4-iodophenyl)-1-methyl-1H-imidazole-4-carboxylate (152 mg). MS 342.8 (M+H).

To a suspension of methyl 2-(4-iodophenyl)-1-methyl-1H-imidazole-4-carboxylate prepared above (72 mg, 0.21 mmol) in toluene (4 mL), LiAlH$_4$ (61 mg, 1.6 mmol) was added. The mixture was heated at 110° C. overnight. After being cooled to room temperature, EtOAc (15 mL) and 1N aq. NaOH (15 mL) were added. The mixture was filtered through celite. The organic layer was separated, dried over Na$_2$SO$_4$, concentrated in vacuo to give (2-(4-iodophenyl)-1-methyl-1H-imidazol-4-yl)methanol (46 mg). MS 315.0 (M+H).

A solution of (2-(4-iodophenyl)-1-methyl-1H-imidazol-4-yl)methanol prepared above (46 mg, 0.15 mmol) in SOCl$_2$ (2 mL) was stirred at room temperature for 15 min. It was concentrated in vacuo to give a residue, which was then partitioned between EtOAc and 5% aq. NaHCO$_3$. The organic phase was separated, dried over Na$_2$SO$_4$, concentrated in vacuo. The residue was dissolved in DMF (2 mL). To the solution, NaN$_3$ (70 mg, 1.1 mmol) was added. After the mixture was stirred at room temperature for 2 days, water and EtOAc were added. The organic layer was separated, dried over Na$_2$SO$_4$, concentrated in vacuo to give (2-(4-iodophenyl)-1-methyl-1H-imidazol-4-yl)methyl azide (46 mg). MS 340.0 (M+H).

A mixture of (2-(4-iodophenyl)-1-methyl-1H-imidazol-4-yl)methyl azide prepared above (46 mg, 0.14 mmol) and Ra—Ni (50% slurry in H$_2$O, 100 mg) in MeOH (5 mL) was hydrogenated under balloon H$_2$ for 1 h. It was filtered. The filtrate was concentrated in vacuo to give (2-(4-iodophenyl)-1-methyl-1H-imidazol-4-yl)methyl amine (42 mg). MS 314.0 (M+H).

To a solution of 5-chloro-thiophene-2-carboxylic acid (23 mg, 0.14 mmol), (2-(4-iodophenyl)-1-methyl-1H-imidazol-4-yl)methyl amine prepared above (21 mg, 0.067 mmol) and TEA (0.050 mL, 0.36 mmol) in DMF (2 mL) was added BOP (70 mg, 0.16 mmol). The mixture was stirred at room temperature overnight. It was then purified by HPLC to give 5-chloro-N-((2-(4-iodophenyl)-1-methyl-1H-imidazol-4-yl)methyl)thiophene-2-carboxamide (14 mg). MS 457.9 and 459.9 (M+H).

A mixture of 5-chloro-N-((2-(4-iodophenyl)-1-methyl-1H-imidazol-4-yl)methyl)thiophene-2-carboxamide prepared above (14 mg, 0.031 mmol), 2-hydroxypyridine (14 mg, 0.15 mmol), 8-hydroxyquinoline (14 mg, 0.097 mmol) and K$_2$CO$_3$ (30 mg, 0.22 mmol) in DMSO (0.5 mL) was degassed with Argon before being charged with CuI (9 mg, 0.047 mmol). The mixture in a sealed tube was heated at 130° C. overnight. It was then purified by HPLC to give the titled compound (2 mg). MS 425.1 and 427.1 (M+H, Cl pattern).

Example 26

5-Chloro-N-((1-(4-iodophenyl)-1H-imidazol-4-yl)methyl)thiophene-2-carboxamide (36)

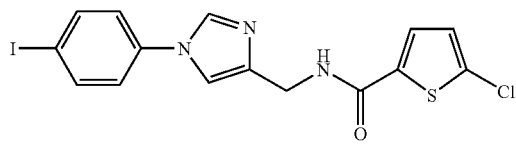

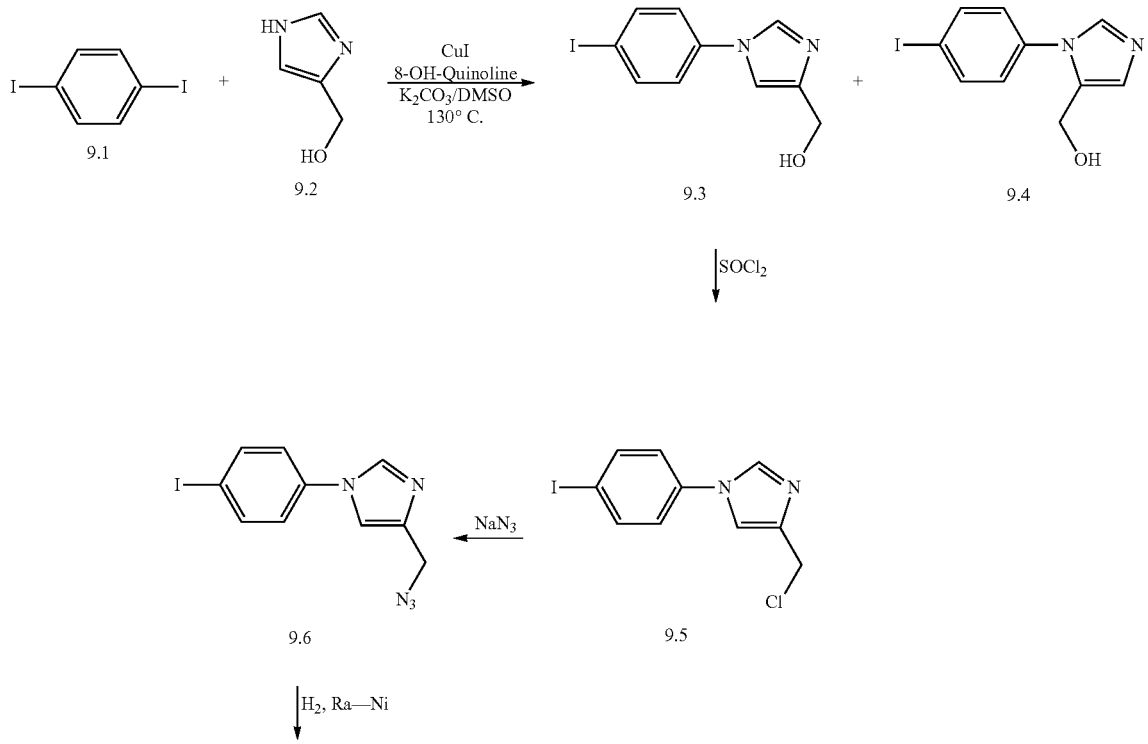

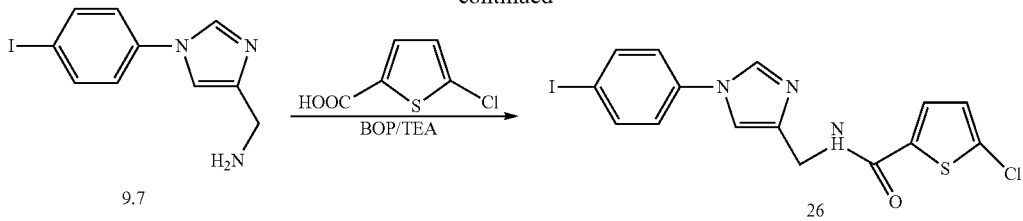

A mixture of 1,4-diiodobenzene 9.1 (4.00 g, 12.1 mmol), 4-(hydroxymethyl)imidazole 9.2 (1.20 g, 12.2 mmol), 8-hydroxyquinoline (0.176 g, 1.21 mmol) and $K_2CO_3$ (1.69 g, 12.2 mmol) in DMSO (12 mL) was degassed before being charged with CuI (0.230 g, 1.21 mmol). The mixture in a sealed tube was heated at 130° C. overnight. Water and EtOAc were added. The mixture was filtered. The organic layer was separated, then applied to a silica gel column, which was eluted with 0-5% MeOH in $CH_2Cl_2$ to give (1-(4-iodophenyl)-1H-imidazol-4-yl)methanol 9.3 (0.810 g) and its isomer (1-(4-iodophenyl)-1H-imidazol-5-yl)methanol 9.4. MS 301.2 (M+H).

Step 2:

The compound 4-hydroxymethyl 1-(4-iodophenyl)imidazole 9.3 (0.810 g, 2.70 mmol) was dissolved in $SOCl_2$ (6 mL). The solution was stirred at room temperature for 15 min. It was then concentrated in vacuo. The residue was partitioned between EtOAc and 5% aq. $NaHCO_3$. The organic layer was separated, dried over $Na_2SO_4$, concentrated in vacuo to give 4-(chloromethyl)-1-(4-iodophenyl)-1H-imidazole 9.5 as a solid (0.780 g). MS 318.9 and 320.9 (M+H, Cl pattern)

Step 3:

The compound 4-(chloromethyl)-1-(4-iodophenyl)-1H-imidazole 9.5 (0.780 g, 2.45 mmol) was dissolved in DMF (10 mL). To the solution, $NaN_3$ (0.520 g, 8.00 mmol) was added. After being stirred at room temperature overnight, water and EtOAc were added. The organic layer was separated, dried over $Na_2SO_4$, concentrated in vacuo to give 4-(azidomethyl)-1-(4-iodophenyl)-1H-imidazole 9.6 as a solid (0.725 g). MS 326.0 (M+H).

Step 4:

A solution of 4-(azidomethyl)-1-(4-iodophenyl)-1H-imidazole 9.6 (0.725 g, 2.23 mmol) over Ra—Ni (50% aq. slurry, 300 mg) in MeOH (12 mL) was hydrogenated under balloon $H_2$ for 3 h. The mixture was filtrated through CELITE. The filtrate was concentrated in vacuo to give (1-(4-iodophenyl)-1H-imidazol-4-yl)methanamine 9.7 as a solid (0.603 g). MS 300.0 (M+H).

Step 5:

To a mixture of 5-chlorothiophene-2-carboxylic acid (0.346 g, 2.13 mmol), (1-(4-iodophenyl)-1H-imidazol-4-yl)methanamine 9.7 (0.578 g, 1.93 mmol) and TEA (0.670 mL, 4.82 mmol) in DMF (10 mL), BOP (1.03 g, 2.33 mmol) was added. The mixture was then stirred at room temperature overnight. Water and EtOAc were added. The organic layer was separated, washed with 5% $NaHCO_3$, dried over $Na_2SO_4$, concentrated in vacuo to give the title compound as a solid (0.832 g). MS found for $C_{15}H_{11}ClIN_3OS$: 443.9 and 445.9 ((M+H)$^+$, Cl pattern).

Example 27

5-Chloro-N-((1-(4-(1-methyl-6-oxo-1,6-dihydropyridazin-3-yl)phenyl)-1H-imidazol-4-yl)methyl)thiophene-2-carboxamide (37)

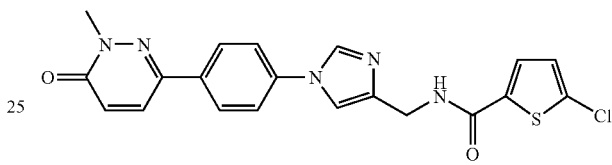

Step 1:

The mixture of 4-iodoacetophenone (1.00 g, 4.06 mmol) and glyoxalic acid monohydrate (0.45 g, 4.9 mmol) in 20 mL acetic acid was refluxed for 18 hrs before concentrated in vacuo. The dry residue was then stirred in 15 mL water to form a slurry material. To it was added carefully with ammonium hydroxide (30%) until pH 9 as indicated by pH paper. The pH was critical for this reaction. Methylhydrazine (0.43 mL) was added, and the reaction was sent to 100° C. bath for 3 hrs before the mixture was diluted with ethyl acetate. The organic phase was washed with brine, dried, concentrated in vacuo, and purified by flash column using 5% methanol in DCM isocratically to yield 6-(4-iodophenyl)-2-methylpyridazin-3(2H)-one (680 mg, 54%). MS found for $C_{11}H_{9}IN_2O$ (M+H)+ 313.0.

Step 2:

The above-prepared compound (145 mg, 0.49 mmol) was dissolved in 10 mL DMSO in a sealed tube. To it were added (1H-imidazol-4-yl)methanol hydrochloride (134 mg, 1.0 mmol), cesium carbonate (815 mg, 2.5 mmol), CuI (48 mg, 0.25 mmol) and 8-hydroxyquinoline (37 mg, 0.25 mmol). The mixture was stirred at 130° C. for 17 hrs. It was filtered and subjected to prep HPLC to isolate 6-(4-(4-(hydroxymethyl)-1H-imidazol-1-yl)phenyl)-2-methylpyridazin-3(2H)-one (95 mg, 69%). MS found for $C_{15}H_{14}N_4O_2$ (M+H)+ 283.1.

Step 3:

The above-prepared compound (95 mg, 0.34 mmol) was stirred in 4 mL acetonitrile at RT. To it was added 4 mL thionyl chloride and the mixture was stirred for 30 min. It was concentrated in vacuo. The residue was then dissolved in 5 mL DMSO and 5 mL ammonia hydroxide was added. The mixture was stirred at 75° C. in a sealed tube for 30 min. It was concentrated in vacuo and subjected to prep HPLC to isolate 6-(4-(4-(aminomethyl)-1H-imidazol-1-yl)phenyl)-2-methylpyridazin-3(2H)-one. MS found for $C_{15}H_{15}N_5O$ (M+H)+ 282.1.

Step 4:

The above-prepared compound was dissolved in 40 mL methanol and treated with MP-carbonate (10 eq.). The mixture was gently stirred for 1 hr and filtered. The filtrate was concentrated in vacuo to give the corresponding free amine (47 mg, 0.17 mmol). It was dissolved in 2 mL DMF. To it was added DIEA (36 μL, 0.20 mmol) and the mixture was stirred at RT. In the meantime, 5-chlorothiophene-2-carboxylic acid (32 mg, 0.20 mmol) was dissolved in 2 mL dry DMF. To it were added DIEA (36 μL, 0.20 mmol) and HATU (76 mg, 0.20 mmol). The mixture was stirred for 10 min. It was added to the stirred solution of the free amine in DMF. The mixture was stirred for 2 hrs and subjected to preparative HPLC to isolate the title compound. MS found for $C_{20}H_{16}ClN_5O_2S$ (M+H)+ 426.1, 428.1 (Cl pattern).

Example 28

5-Chloro-N-((1-(4-(2-methoxypyridin-3-yl)phenyl)-1H-imidazol-4-yl)methyl)thiophene-2-carboxamide (38)

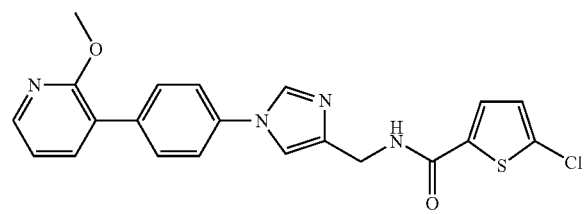

To a solution of diisopropylamine (1.42 mL, 10 mmol) in THF (10 mL) at 0° C. was added nBuLi (2.5 M, 4.25 mL, 10.6 mmol) dropwise. After stirring at 0° C. for 45 min, a solution of 2-methoxypyridine (0.96 mL, 9.2 mmol) in THF (5 mL) was added, and the mixture was stirred for an additional 1 h before B(OiPr)$_3$ (2.54 mL, 11 mmol) was added. 30 min later, H$_2$O was added to quench the reaction, the THF was removed in vacuo and the aqueous layer was extracted with ether. The aqueous layer was separated, acidified with 48% HBr to pH=4, the resulting precipitates were collected by filtration to yield 2-methoxypyridine-3-ylboronic acid (0.46 g, 40%).

A mixture of 5-chloro-N-((1-(4-iodophenyl-1H-imidazol-4-yl)methyl)thiophene-2-carboxamide (0.044 g, 0.1 mmol), 2-methoxypyridine-3-ylboronic acid (0.016 g, 0.11 mmol) and Pd(PPh$_3$)$_2$Cl$_2$ (0.007 g, 0.01 mmol) in p-dioxane (0.7 mL) was purged with Argon for 5 min. A degassed aqueous solution of Na$_2$CO$_3$ (IM, 0.3 mL) was added. After being heated at 100° C. for 2 h, the mixture was cooled to room temperature, and purified by preparative HPLC to yield 5-chloro-N-((1-(4-(2-methoxypyridin-3-yl)phenyl-1H-imidazol-4-yl)methyl)thiophene-2-carboxamide (MS 425.0, 427.0 (M+H), Cl pattern).

Example 29

5-chloro-N-((1-(4-(2-oxo-1,2-dihydropyridin-3-yl)phenyl)-1H-imidazol-4-yl)methyl)thiophene-2-carboxamide (39)

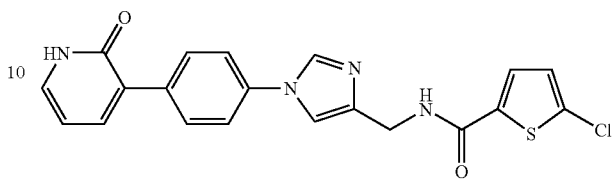

To a solution of 5-chloro-N-((1-(4-(2-methoxypyridin-3-yl)phenyl-1H-imidazol-4-yl)methyl)thiophene-2-carboxamide (0.01 g, 0.024 mmol) in AcCN (1 mL) was added NaI (0.011 g, 0.072 mmol) and TMSCl (0.045 mL, 0.36 mmol). After heating at 80° C. for 90 min, the reaction mixture was cooled to room temperature, and purified by preparative HPLC to yield 5-chloro-N-((1-(4-(2-oxo-1,2-dihydropyridin-3-yl)phenyl-1H-imidazol-4-yl)methyl)thiophene-2-carboxamide (MS 411.0, 413.0 (M+H) Cl pattern).

Example 30

5-Chloro-N-((1-(4-(1-methyl-2-oxo-1,2-dihydropyridin-3-yl)phenyl)-1H-imidazol-4-yl)methyl)thiophene-2-carboxamide (40)

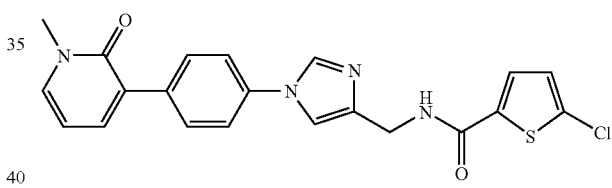

To a solution of 5-chloro-N-((1-(4-(2-oxo-1,2-dihydropyridin-3-yl)phenyl-1H-imidazol-4-yl)methyl)thiophene-2-carboxamide (0.02 g, 0.05 mmol) in DMF (0.5 mL) was added Cs$_2$CO$_3$ (0.049 g, 0.15 mmol) and MeI (0.01 mL, 0.15 mmol). After stirring for 30 min at ambient temperature, the mixture was purified by preparative HPLC to give 5-chloro-N-((1-(4-(1-methyl-2-oxo-1,2-dihydropyridin-3-yl)phenyl-1H-imidazol-4-yl)methyl)thiophene-2-carboxamide (MS 425.1, 427.1 (M+H) Cl pattern).

Example 31

4-Chloro-N-((1-(4-(2-oxopyridin-1(2H)-yl)phenyl)-1H-imidazol-4-yl)methyl)benzamide (43)

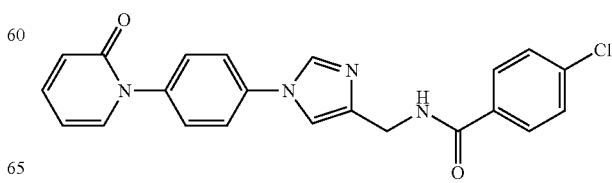

To a solution of 4-chlorobenzoic acid (40 mg, 0.26 mmol) and triethylamine (0.150 mL, 1.08 mmol) in DMF (2 mL), BOP (135 mg, 0.30 mmol) was added. After 5 min of stirring, 1-(4-(4-(aminomethyl)-1H-imidazol-1-yl)phenyl)pyridin-2(1H)-one hydrochloride (53 mg, 0.18 mmol) was added. The mixture was stirred at room temperature for 2 h. It was then purified by HPLC to give the titled compound (25 mg). MS 405.1 and 407.1 (M+H, Cl pattern).

Example 32

5-Chloro-N-((1-(5-(2-oxopyridin-1(2H)-yl)pyridin-2-yl)-1H-imidazol-4-yl)methyl)thiophene-2-carboxamide (45)

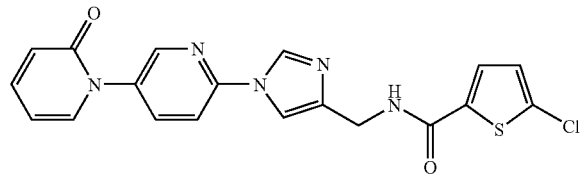

Step 1:

A mixture of 5-bromo-2-fluoropyridine (630 mg, 3.58 mmol), 4-imidazolecarboxaldehyde (355 mg, 3.70 mmol) and K$_2$CO$_3$ (1.00 g, 7.25 mmol) in DMF (10 mL) was stirred at 70° C. overnight. After being cooled down, H$_2$O was added to induce precipitation. The precipitate was collected and dried on vacuum to give 1-(5-bromopyridin-2-yl)-1H-imidazole-4-carbaldehyde (738 mg).

Step 2:

To a suspension of 1-(5-bromopyridin-2-yl)-1H-imidazole-4-carbaldehyde (730 mg, 2.90 mmol) in MeOH (10 mL) at room temperature was added NaBH$_4$ (134 mg, 3.53 mmol). The mixture was stirred for 30 min, during which time the suspension became clear. The solvent was removed in vacuo. The residue was partitioned between H$_2$O and EtOAc. The organic phase was separated, washed with 5% NaHCO$_3$, dried over Na$_2$SO$_4$, concentrated in vacuo to give (1-(5-bromopyridin-2-yl)-1H-imidazol-4-yl)methanol as a solid (520 mg).

Step 3:

To a suspension of (1-(5-bromopyridin-2-yl)-1H-imidazol-4-yl)methanol (520 mg, 2.05 mmol) in CH$_3$CN (5 mL) at room temperature was added SOCl$_2$ (2.5 mL). With the addition, the suspension became clear. After 10 min of stirring, the mixture was concentrated in vacuo. The residue was dissolved in DMF (12 mL), and NaN$_3$ (565 mg, 8.69 mmol) was added. The mixture was stirred at room temperature overnight. H$_2$O and EtOAc were added. The organic phase was separated, washed with 5% NaHCO$_3$, dried over Na$_2$SO$_4$, concentrated in vacuo to give 2-(4-(azidomethyl)-1H-imidazol-1-yl)-5-bromopyridine (500 mg).

Step 4:

A mixture of 2-(4-(azidomethyl)-1H-imidazol-1-yl)-5-bromopyridine (500 mg, 1.79 mmol) and iron powder (767 mg, 13.7 mmol) in EtOH (8 mL) and HOAc (6 mL) was heated at reflux for 2 h. It was filtered through celite. The filtrate was concentrated in vacuo. The residue was partitioned between 5% NaHCO$_3$ and EtOAc. The biphasic solution was filtered. The EtOAc phase was separated, dried over Na$_2$SO$_4$, and concentrated in vacuo to give (1-(5-bromopyridin-2-yl)-1H-imidazol-4-yl)methanamine (253 mg).

Step 5:

To a solution of 5-chloro-2-thiophenecarboxylic acid (195 mg, 1.20 mmol) and triethylamine (0.400 mL, 2.87 mmol) in DMF (5 mL), BOP (550 mg, 1.24 mmol) was added. After 5 min of stirring, a solution of (1-(5-bromopyridin-2-yl)-1H-imidazol-4-yl)methanamine (253 mg, 1.00 mmol) in DMF (5 mL) was added. The mixture was stirred at room temperature overnight. H$_2$O and EtOAc were added. The organic phase was separated, washed with 5% NaHCO$_3$, dried over Na$_2$SO$_4$, and concentrated in vacuo. The residue was purified by HPLC to give N-((1-(5-bromopyridin-2-yl)-1H-imidazol-4-yl)methyl)-5-chlorothiophene-2-carboxamide (85 mg).

Step 6:

A mixture of N-((1-(5-bromopyridin-2-yl)-1H-imidazol-4-yl)methyl)-5-chlorothiophene-2-carboxamide (42 mg, 0.11 mmol), 2-hydroxypyridine (40 mg, 0.42 mmol), N,N'-dimethylethylenediamine (0.035 mL, 0.32 mmol) and K$_2$CO$_3$ (52 mg, 0.38 mmol) in DMSO (1 mL) and dioxane (1 mL) was degassed with Argon before being charged with CuI (23 mg, 0.12 mmol). The mixture was heated at 110° C. overnight in a sealed tube. It was then purified by HPLC to give the title compound (3 mg). MS found for C$_{19}$H$_{14}$ClN$_5$O$_2$S: 412.2 and 414.2 (M+H, Cl pattern).

Example 33

5-Chloro-N-((1-(6-(2-oxopyridin-1(2H)-yl)pyridin-3-yl)-1H-imidazol-4-yl)methyl)thiophene-2-carboxamide (46)

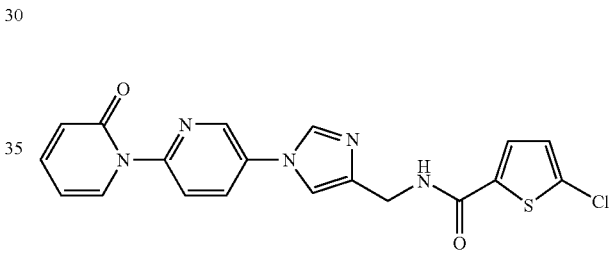

A mixture of 3-amino-6-bromopyridine (865 mg, 5.00 mmol), 2-hydroxypyridine (475 mg, 5.00 mmol), N,N'-dimethylethylenediamine (0.215 mL, 2.00 mmol) and K$_2$CO$_3$ (1.38 g, 10.0 mmol) in dioxane (8 mL) was degassed with Argon before being charged with CuI (190 mg, 1.00 mmol). The mixture in a sealed tube was heated at 110° C. overnight. After being cooled down, H$_2$O and nBuOH were added. The organic phase was separated, and concentrated in vacuo to give 1-(5-aminopyridin-2-yl)pyridin-2(1H)-one (316 mg).

To a solution of 1-(5-aminopyridin-2-yl)pyridin-2(1H)-one (316 mg, 1.69 mmol) in concentrated HCl (8 mL) cooled in an ice bath, a solution of NaNO$_2$ (117 mg, 1.69 mmol) in H$_2$O (3 mL) was added dropwise. After 30 min of stirring, NaI (1.03 g, 6.87 mmol) in H$_2$O (4 mL) was added. The mixture was stirred at 0° C. for 1 h. It was then allowed to warm up to room temperature and stirred at room temperature overnight. The mixture was extracted with EtOAc. The EtOAc solution was washed with 5% NaHCO$_3$, then with Na$_2$S$_2$O$_3$, dried over Na$_2$SO$_4$, and concentrated in vacuo to give 1-(5-iodopyridin-2-yl)pyridin-2(1H)-one (189 mg).

A mixture of 1-(5-iodopyridin-2-yl)pyridin-2(1H)-one (75 mg, 0.25 mmol), N-((1H-imidazol-4-yl)methyl)-5-chlorothiophene-2-carboxamide (60 mg, 0.17 mmol), 8-hydroxyquinoline (10 mg, 0.069 mmol) and K$_2$CO$_3$ (100 mg, 0.72 mmol) in DMSO (1 mL) was degassed with Argon before being charged with CuI (19 mg, 0.10 mmol). The mixture in a sealed tube was heated at 130° C. overnight. It was then purified by HPLC to give the title compound (11 mg). MS found for C$_{19}$H$_{14}$ClN$_5$O$_2$S: 412.0 and 414.0 (M+H, Cl pattern).

Example 34

5-Chloro-N-((1-(4-(1-methyl-6-oxo-1,6-dihydropyridazin-3-yl)phenyl)-1H-imidazol-5-yl)methyl)thiophene-2-carboxamide (51)

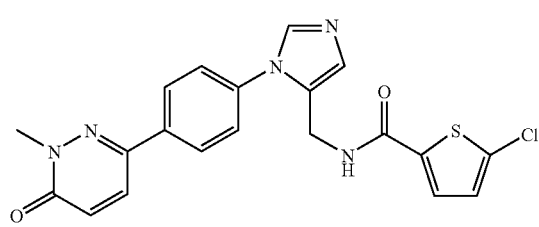

SCHEME 10

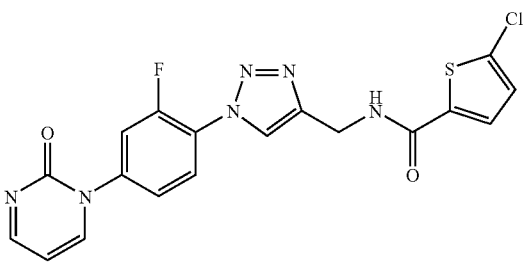

The compound 10.1 was prepared from (1-(4-iodophenyl)-1H-imidazol-5-yl)methanol (Compound 9.4, prepared as shown in Example 26) using a similar procedure as described in Example 26. The title compound was prepared from compound 10.1 under conditions similar to that described in step 4 of Example 1. MS found for C$_{20}$H$_{16}$ClN$_5$O$_2$S (M+H)+ 426.1 (Cl pattern).

Example 35

5-Chloro-N-((1-(2-fluoro-4-(2-oxopyrazin-1(2H)-yl)phenyl)-1H-1,2,3-triazol-4-yl)methyl)thiophene-2-carboxamide (54)

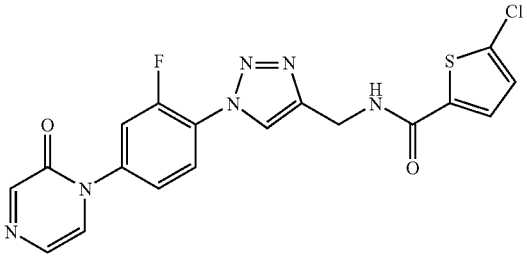

The title compound was prepared using a similar procedure as described in EXAMPLE 4. MS found for C$_{18}$H$_{12}$ClFN$_6$O$_2$S (M+H)+ 431.0, 433.0 (Cl pattern).

Example 36

5-Chloro-N-((1-(2-fluoro-4-(2-oxopyrimidin-1(2H)-yl)phenyl)-1H-1,2,3-triazol-4-yl)methyl)thiophene-2-carboxamide (55)

The title compound was prepared using a similar procedure as described in Example 4. MS found for C$_{18}$H$_{12}$ClFN$_6$O$_2$S (M+H)+ 431.0, 433.0 (Cl pattern).

Example 37

5-Chloro-N-((1-(2-fluoro-4-(2-oxo-tetrahydropyrimidin-1(2H)-yl)phenyl)-1H-1,2,3-triazol-4-yl)methyl)thiophene-2-carboxamide (57)

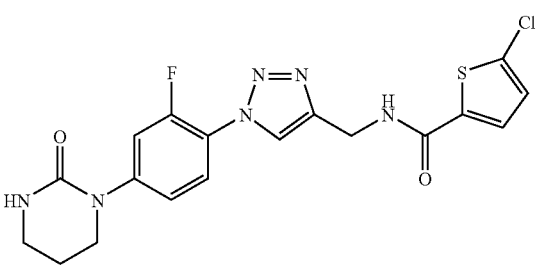

The title compound was prepared using a similar procedure as described in Example 4. MS found for C$_{18}$H$_{16}$ClFN$_6$O$_2$S (M+H)+ 435.0, 437.0 (Cl pattern).

Example 38

5-Chloro-N-((1-(2-fluoro-4-(3-methyl-2-oxo-tetrahydropyrimidin-1(2H)-yl)phenyl)-1H-1,2,3-triazol-4-yl)methyl)thiophene-2-carboxamide (58)

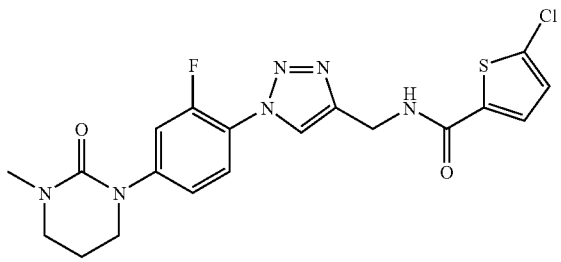

The title compound was prepared using a similar procedure as described in Example 4. MS found for $C_{19}H_{18}ClFN_6O_2S$ (M+H)+ 449.0, 451.0 (Cl pattern).

Example 39

5-Chloro-N-((1-(2-fluoro-4-(2-oxopiperidin-1-yl)phenyl)-1H-1,2,3-triazol-4-yl)methyl)thiophene-2-carboxamide (59)

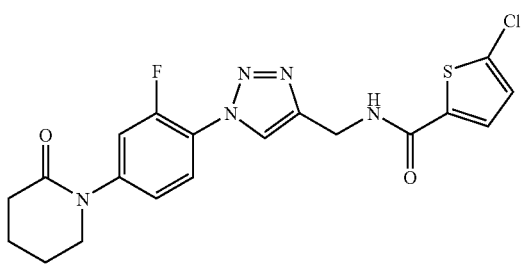

The title compound was prepared using a similar procedure as described in Example 4. MS found for $C_{19}H_{17}ClFN_5O_2S$ (M+H)+ 434.1, 436.1 (Cl pattern).

Example 40

5-Chloro-N-((1-(3-fluoro-4-(2-oxopyridin-1(2H)-yl)phenyl)-1H-1,2,3-triazol-4-yl)methyl)thiophene-2-carboxamide (60)

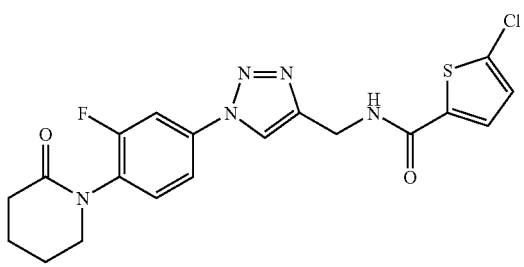

The title compound was prepared using a similar procedure as described in Example 4. MS found for $C_{19}H_{13}ClFN_5O_2S$ (M+H)+ 430.0, 432.0 (Cl pattern).

Example 41

5-Chloro-N-((1-(4-(3-hydroxy-2-oxopyridin-1(2H)-yl)phenyl)-1H-1,2,3-triazol-4-yl)methyl)thiophene-2-carboxamide (61)

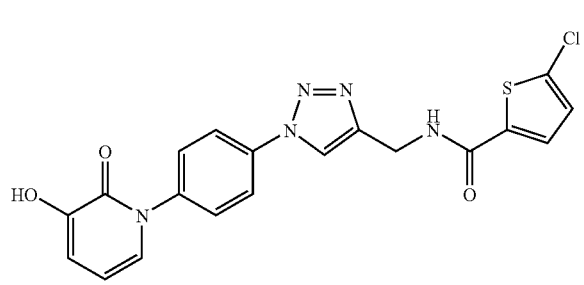

5-Chloro-N-((1-(4-(3-methoxy-2-oxopyridin-1(2H)-yl)phenyl)-1H-1,2,3-triazol-4-yl)methyl)thiophene-2-carboxamide (306 mg, 0.69 mmol, prepared using a similar procedure as described in Example 4) was stirred in 40 mL DCM as a slurry. BBr₃ (200 µL, 2.1 mmol) was added. The mixture was stirred for 2 hrs and concentrated in vacuo. The residue was dissolved in 1 mL and 5 mL DMSO and subjected to prep HPLC to isolate the title compound as a white powder. MS found for $C_{19}H_{14}ClN_5O_3S$ (M+H)+ 428.1, 430.1 (Cl pattern).

Example 42

5-Chloro-N-((1-(4-(3-(2-hydroxyethoxy)-2-oxopyridin-1(2H)-yl)phenyl)-1H-1,2,3-triazol-4-yl)methyl)thiophene-2-carboxamide (62)

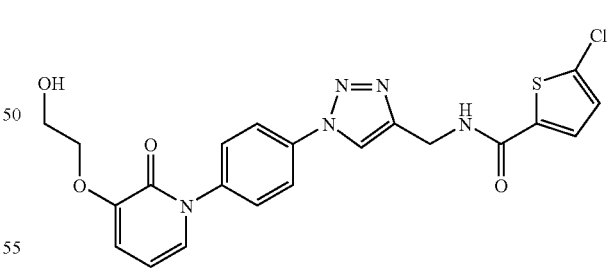

5-Chloro-N-((1-(4-(3-hydroxy-2-oxopyridin-1(2H)-yl)phenyl)-1H-1,2,3-triazol-4-yl)methyl)thiophene-2-carboxamide (30 mg, 0.07 mmol, prepared as shown in EXAMPLE 61) was dissolved in 2 mL DMSO. To it were added cesium carbonate (69 mg, 0.21 mmol) and 2-bromoethanol (10 µL, 0.14 mmol). The mixture was stirred in a sealed tube at 70° C. for 30 min, and was directly subjected to reverse phase prep HPLC to isolate the title compound. MS found for $C_{21}H_{18}ClN_5O_4S$ (M+H)+ 472.1, 474.1 (Cl pattern).

Example 43

5-Chloro-N-((1-(4-(3-(2-methoxyethoxy)-2-oxopyridin-1(2H)-yl)phenyl)-1H-1,2,3-triazol-4-yl)methyl)thiophene-2-carboxamide (63)

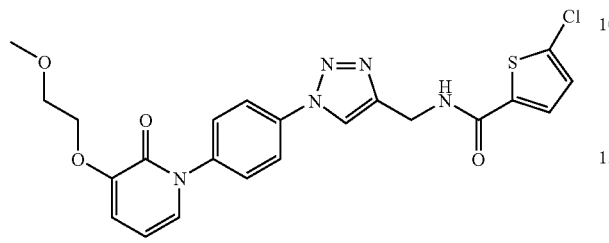

The title compound was prepared using a similar procedure as described in Example 42. MS found for $C_{22}H_{20}ClN_5O_4S$ (M+H)+ 486.1, 488.1 (Cl pattern).

Example 44

5-Chloro-N-((1-(4-(3-(2-(dimethylamino)ethoxy)-2-oxopyridin-1(2H)-yl)phenyl)-1H-1,2,3-triazol-4-yl)methyl)thiophene-2-carboxamide (64)

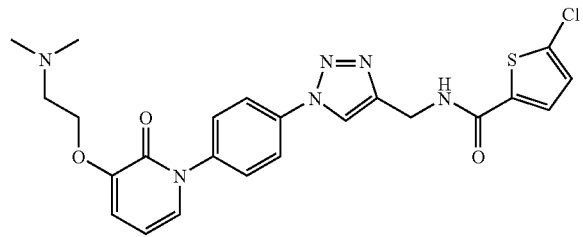

The title compound was prepared using a similar procedure as described in Example 42. MS found for $C_{23}H_{23}ClN_6O_3S$ (M+H)+ 499.1, 501.1 (Cl pattern).

Example 45

5-Chloro-N-((1-(4-(3-(2-(dimethyl(dimethylamino)amino)ethoxy)-2-oxopyridin-1(2H)-yl)phenyl)-1H-1,2,3-triazol-4-yl)methyl)thiophene-2-carboxamide (65)

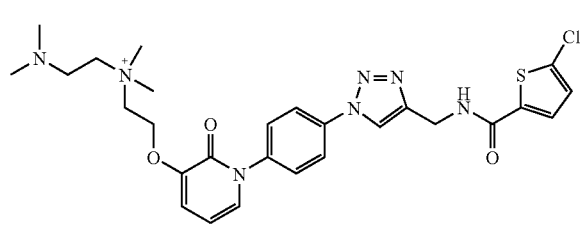

The title compound was prepared using a similar procedure as described in Example 42. MS found for $C_{27}H_{33}ClN_7O_3S$ (M+H)+ 570.1, 572.1 (Cl pattern).

Example 46

5-Chloro-N-((1-(4-(2-oxo-3-(2-(piperidin-1-yl)ethoxy)pyridin-1(2H)-yl)phenyl)-1H-1,2,3-triazol-4-yl)methyl)thiophene-2-carboxamide (66)

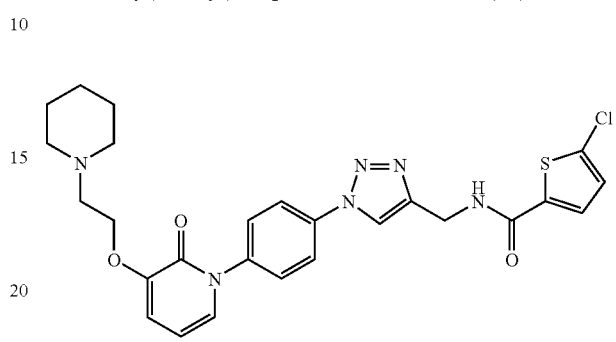

The title compound was prepared using a similar procedure as described in Example 42. MS found for $C_{26}H_{27}ClN_6O_3S$ (M+H)+ 539.1, 541.1(Cl pattern).

Example 47

5-Chloro-N-((1-(4-(2-oxo-3-(3-(piperidin-1-yl)propoxy)pyridin-1(2H)-yl)phenyl)-1H-1,2,3-triazol-4-yl)methyl)thiophene-2-carboxamide (67)

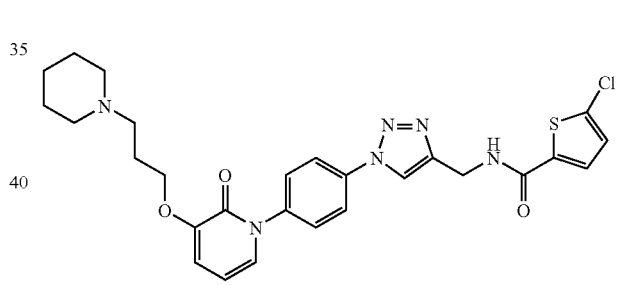

The title compound was prepared using a similar procedure as described in Example 42. MS found for $C_{27}H_{29}ClN_6O_3S$ (M+H)+ 553.1, 555.1 (Cl pattern).

Example 48

5-Chloro-N-((1-(4-(3-(2-(methylthio)ethoxy)-2-oxopyridin-1(2H)-yl)phenyl)-1H-1,2,3-triazol-4-yl)methyl)thiophene-2-carboxamide (68)

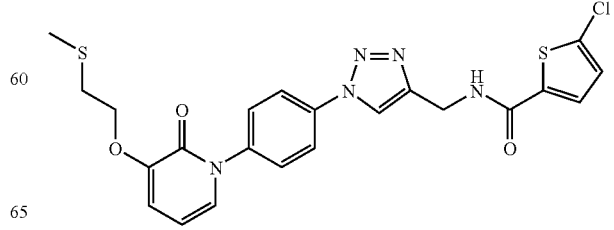

The title compound was prepared using a similar procedure as described in Example 42. MS found for $C_{22}H_{20}ClN_5O_3S_2$ (M+H)+ 502.1, 504.1 (Cl pattern).

Example 49

5-Chloro-N-((1-(4-(3-(2-(methylsulfinyl)ethoxy)-2-oxopyridin-1(2H)-yl)phenyl)-1H-1,2,3-triazol-4-yl)methyl)thiophene-2-carboxamide (69)

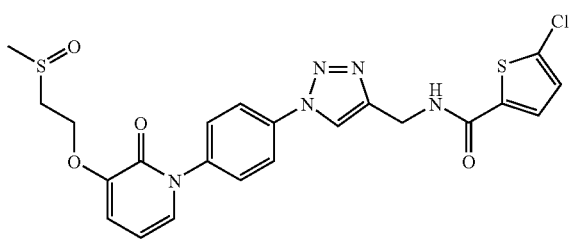

To a solution of Example 48 in a 2:1 mixture of methanol and water was added 1.0 equivalent of oxone. The mixture was stirred at room temperature for 10 min and directly subjected to reverse phase HPLC to isolate the title compound as a white powder after lyophilization. MS found for $C_{22}H_{20}ClN_5O_4S_2$ (M+H)+ 518.1, 520.1 (Cl pattern).

Example 50

5-Chloro-N-((1-(4-(3-(2-(methylsulfonyl)ethoxy)-2-oxopyridin-1(2H)-yl)phenyl)-1H-1,2,3-triazol-4-yl)methyl)thiophene-2-carboxamide (70)

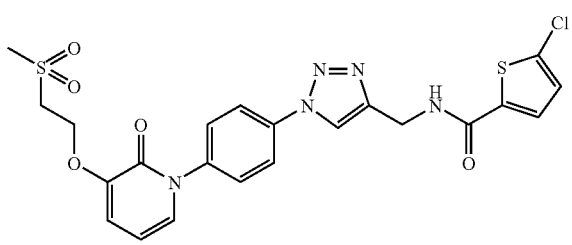

To a solution of Example 48 in a 2:1 mixture of methanol and water was added 3 equivalent of oxone. The mixture was stirred at room temperature for 1 hr and directly subjected to reverse phase HPLC to isolate the title compound as a white powder after lyophilization. MS found for $C_{22}H_{20}ClN_5O_5S_2$ (M+H)+ 534.1, 536.1 (Cl pattern).

Example 51

5-Chloro-N-((1-(4-(3-(2-morpholinoethoxy)-2-oxopyridin-1(2H)-yl)phenyl)-1H-1,2,3-triazol-4-yl)methyl)thiophene-2-carboxamide (71)

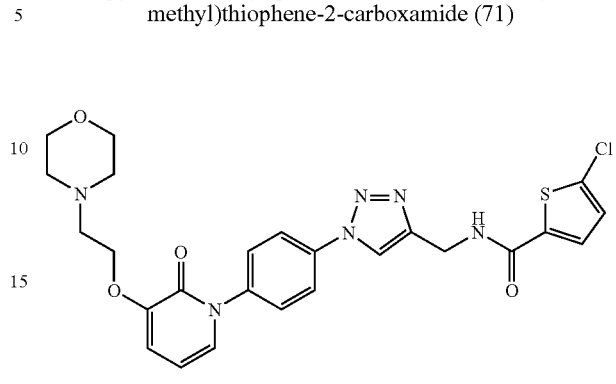

The title compound was prepared using a similar procedure as described in Example 42. MS found for $C_{25}H_{25}ClN_6O_4S$ (M+H)+ 541.1, 543.1 (Cl pattern).

Example 52

N-((1-(4-(3-(2-(1H-Imidazol-1-yl)ethoxy)-2-oxopyridin-1(2H)-yl)phenyl)-1H-1,2,3-triazol-4-yl)methyl)-5-chlorothiophene-2-carboxamide (72)

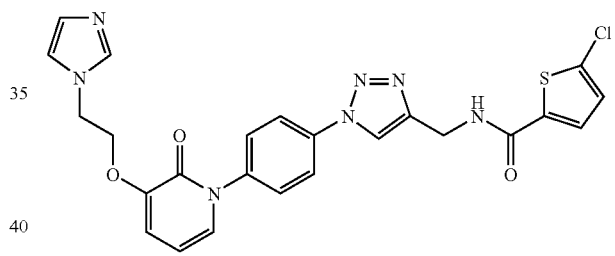

The title compound was prepared using a similar procedure as described in Example 42. MS found for $C_{24}H_{20}ClN_7O_3S$ (M+H)+ 522.1, 524.1 (Cl pattern).

Example 53

5-Chloro-N-((1-(4-(3-((1-methyl-1H-imidazol-2-yl)methoxy)-2-oxopyridin-1(2H)-yl)phenyl)-1H-1,2,3-triazol-4-yl)methyl)thiophene-2-carboxamide (73)

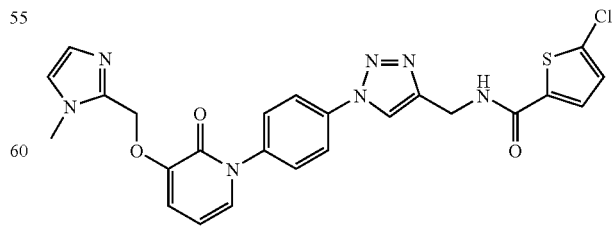

The title compound was prepared using a similar procedure as described in Example 42. MS found for $C_{24}H_{20}ClN_7O_3S$ (M+H)+ 522.1, 524.1 (Cl pattern).

Example 54

5-Chloro-N-((1-(4-(5-hydroxy-2-oxopyridin-1(2H)-yl)phenyl)-1H-1,2,3-triazol-4-yl)methyl)thiophene-2-carboxamide (74)

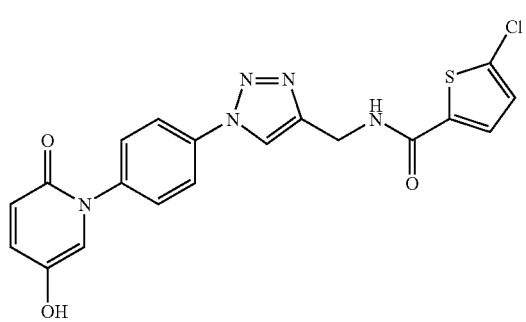

The title compound was prepared using a similar procedure as described in Example 41 from 5-chloro-N-((1-(4-(5-methoxy-2-oxopyridin-1(2H)-yl)phenyl)-1H-1,2,3-triazol-4-yl)methyl)thiophene-2-carboxamide (prepared using a similar procedure as described in Example 4). MS found for $C_{19}H_{14}ClN_5O_3S$ (M+H)+ 428.1, 430.1 (Cl pattern).

Example 55

5-Chloro-N-((1-(4-(5-(2-(dimethylamino)ethoxy)-2-oxopyridin-1(2H)-yl)phenyl)-1H-1,2,3-triazol-4-yl)methyl)thiophene-2-carboxamide (75)

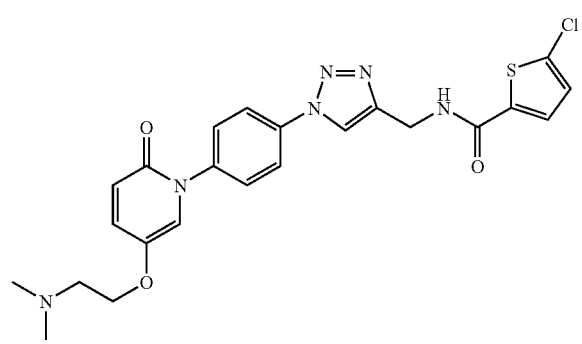

The title compound was prepared using the same procedure described in Example 42 from 5-Chloro-N-((1-(4-(5-hydroxy-2-oxopyridin-1(2H)-yl)phenyl)-1H-1,2,3-triazol-4-yl)methyl)thiophene-2-carboxamide (prepared as shown in EXAMPLE 74). MS found for $C_{23}H_{23}ClN_6O_3S$ (M+H)+ 499.1, 501.1 (Cl pattern).

Example 56

N-((1-(4-(4-Amino-2-oxopyrimidin-1(2H)-yl)phenyl)-1H-1,2,3-triazol-4-yl)methyl)-5-chlorothiophene-2-carboxamie (79)

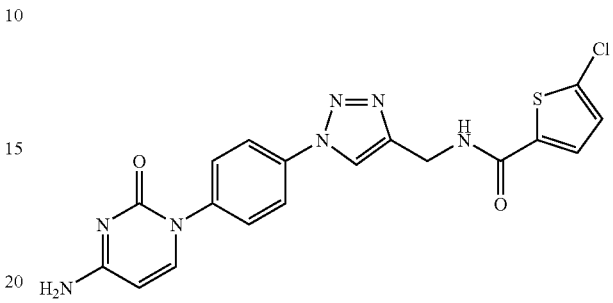

The mixture of 5-chloro-N-((1-(4-iodophenyl)-1H-1,2,3-triazol-4-yl)methyl)thiophene-2-carboxamide (100 mg, 0.23 mmol), cytosine (100 mg, 0.90 mmol), CuI (23 mg, 0.12 mmol), 8-hydroxyquinoline (18 mg, 0.12 mmol), potassium carbonate (96 mg, 0.69 mmol) in 2 mL DMSO in a sealed tube was stirred for 15 hrs at 120° C. The title compound was isolated directly from the reaction mixture using reverse phase prep HPLC. MS found for $C_{18}H_{14}ClN_7O_2S$ (M+H)+ 428.1, 430.1 (Cl pattern).

Example 57

5-Chloro-N-((1-(4-(2,4-dioxo-3,4-dihydropyrimidin-1(2H)-yl)phenyl)-1H-1,2,3-triazol-4-yl)methyl)thiophene-2-carboxamide (80)

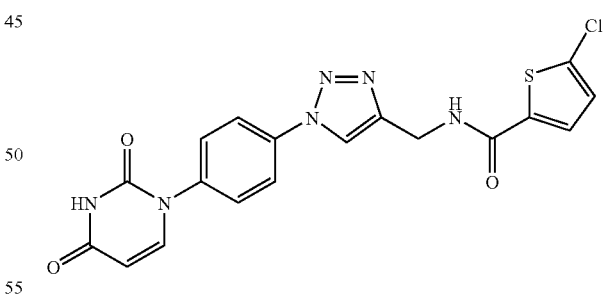

The mixture of 5-chloro-N-((1-(4-iodophenyl)-1H-1,2,3-triazol-4-yl)methyl)thiophene-2-carboxamide (100 mg, 0.23 mmol), uracil (100 mg, 0.90 mmol), CuI (23 mg, 0.12 mmol), 8-hydroxyquinoline (18 mg, 0.12 mmol), potassium carbonate (96 mg, 0.69 mmol) in 2 mL DMSO in a sealed tube was stirred for 15 hrs at 120° C. The title compound was isolated directly from the reaction mixture using reverse phase prep HPLC. MS found for $C_{18}H_{13}ClN_6O_3S$ (M+H)+ 429.1, 431.1 (Cl pattern).

Example 58

N-((1-(4-(4-Amino-5-fluoro-2-oxopyrimidin-1(2H)-yl)phenyl)-1H-1,2,3-triazol-4-yl)methyl)-5-chlorothiophene-2-carboxamide (81)

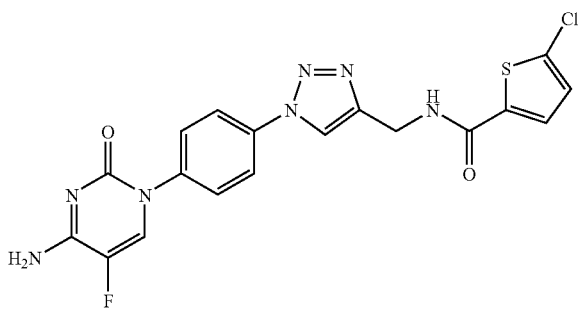

The title compound was prepared using a similar procedure as described in Example 57. MS found for $C_{18}H_{13}ClFN_7O_2S$ (M+H)+ 446.1, 448.1 (Cl pattern).

Example 59

5-Chloro-N-((1-(4-(3-methyl-2,4-dioxo-3,4-dihydropyrimidin-1(2H)-yl)phenyl)-1H-1,2,3-triazol-4-yl)methyl)thiophene-2-carboxamide (82)

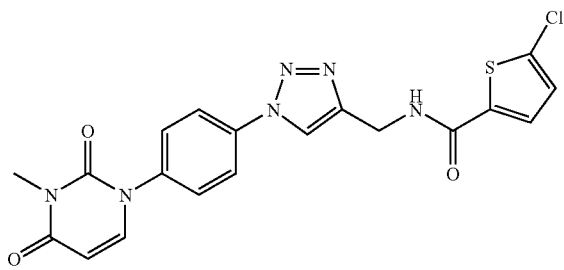

The title compound was prepared using a similar procedure as described in Example 57. MS found for $C_{19}H_{15}ClN_6O_3S$ (M+H)+ 443.1, 445.1 (Cl pattern).

Example 60

5-Chloro-N-((1-(4-(2-oxopiperazin-1-yl)phenyl)-1H-1,2,3-triazol-4-yl)methyl)thiophene-2-carboxamide (83)

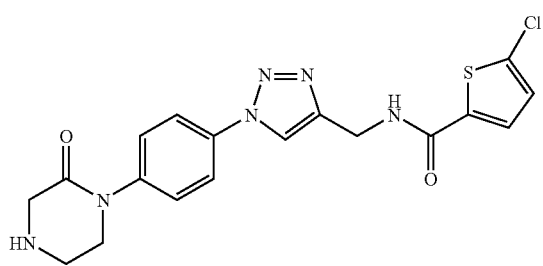

A mixture of 5-chloro-N-((1-(4-iodophenyl)-1H-1,2,3-triazol-4-yl)methyl)thiophene-2-carboxamide (100 mg, 0.22 mmol), 4-N-Boc-2-oxo-piperazine (88 mg, 0.44 mmol), CuI (13 mg, 0.066 mmol), N,N'-dimethylethylenediamine (8 µL, 0.066 mmol), potassium carbonate (61 mg, 0.44 mmol) in 5 mL dioxane in a sealed tube was stirred for 2 days at 120° C. The mixture was diluted with ethyl acetate (200 mL). It was washed with brine, dried, and concentrated in vacuo. The residue was treated with neat TFA for 15 min and directly subjected to prep HPLC to isolate the title compound. MS found for $C_{18}H_{17}ClN_6O_2S$ (M+H)+ 417.1, 419.1 (Cl pattern).

Example 61

5-Chloro-N-((1-(4-(4-methyl-2-oxopiperazin-1-yl)phenyl)-1H-1,2,3-triazol-4-yl)methyl)thiophene-2-carboxamide (84)

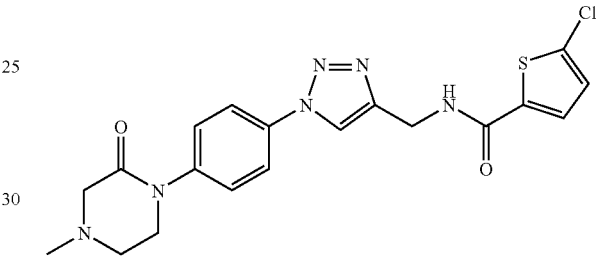

5-Chloro-N-((1-(4-(2-oxopiperazin-1-yl)phenyl)-1H-1,2,3-triazol-4-yl)methyl)thiophene-2-carboxamide (24 mg, 0.06 mmol, prepared as shown in Example 60) was stirred in 2 mL acetic acid at RT. To it was added formaldehyde (37% in water, 22 µL, 0.3 mmol). The mixture was stirred for 10 min. NaBH₃CN (30 mg, 0.48 mmol) was added. The reaction was allowed for 10 min, and directly subjected to reverse phase prep HPLC to isolate the title compound. MS found for $C_{19}H_{19}ClN_6O_2S$ (M+H)+ 431.1, 433.1 (Cl pattern).

Example 62

5-Chloro-N-((1-(4-(4-isopropyl-2-oxopiperazin-1-yl)phenyl)-1H-1,2,3-triazol-4-yl)methyl)thiophene-2-carboxamide (85)

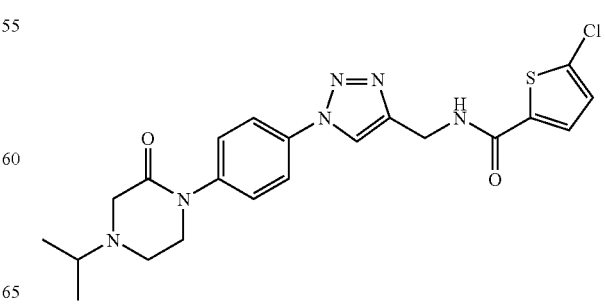

The title compound was prepared using a similar procedure as described in Example 61. MS found for $C_{21}H_{23}ClN_6O_2S$ (M+H)+ 459.1, 461.1 (Cl pattern).

Example 63

4-(4-(4-((5-Chlorothiophene-2-carboxamido)methyl)-1H-1,2,3-triazol-1-yl)phenyl)-3-oxopiperazine-1-carboxamide (86)

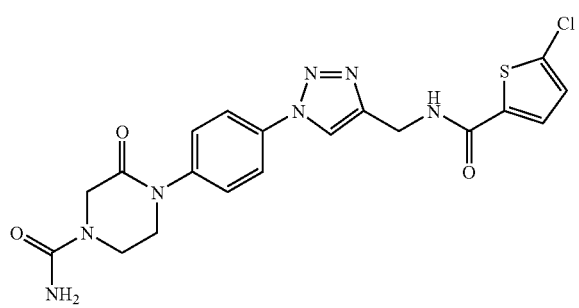

5-Chloro-N-((1-(4-(2-oxopiperazin-1-yl)phenyl)-1H-1,2,3-triazol-4-yl)methyl)thiophene-2-carboxamide (23 mg, 0.055 mmol, prepared as shown in Example 60) was dissolved in 2 mL water and 0.5 mL DMSO. To it was added KOCN (23 mg, 0.28 mmol). The mixture was stirred at RT over the weekend. The title compound was the major product in this reaction and was isolated using direct reverse phase prep HPLC. MS found for $C_{19}H_{18}ClN_7O_3S$ (M+H)+ 460.1, 462.1 (Cl pattern).

Example 64

5-Chloro-N-((1-(4-(3-hydroxy-2-oxopyrazin-1(2H)-yl)phenyl)-1H-1,2,3-triazol-4-yl)methyl)thiophene-2-carboxamide (87)

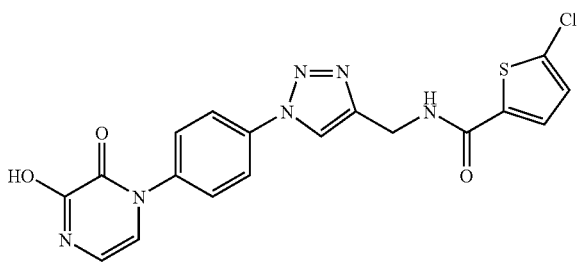

The mixture of 5-chloro-N-((1-(4-iodophenyl)-1H-1,2,3-triazol-4-yl)methyl)thiophene-2-carboxamide (100 mg, 0.22 mmol), 2,3-pyrazinediol (74 mg, 0.66 mmol), CuI (21 mg, 0.11 mmol), 8-hydroxyquinoline (16 mg, 0.11 mmol), potassium carbonate (152 mg, 1.1 mmol) in 2 mL DMSO in a sealed tube was stirred for 15 hrs at 130° C. The title compound was isolated directly from the reaction mixture using reverse phase prep HPLC. MS found for $C_{18}H_{13}ClN_6O_3S$ (M+H)+ 429.1, 431.1 (Cl pattern).

Example 65

5-Chloro-N-((1-(4-(2-oxopyridin-1(2H)-yl)phenyl)-1H-pyrrol-3-yl)methyl)thiophene-2-carboxamide (108)

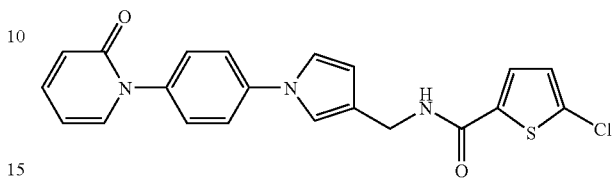

A solution of 4-iodoaniline (0.684 g, 3.12 mmol) and 2,5-dimethoxy-3-tetrahydrofurancarboxaldehyde (90%, 0.492 mL, 3.12 mmol) in HOAc (10 mL) was stirred at 90° C. for 1 h. The solvent was removed in vacuo. The residue was partitioned between EtOAc and $H_2O$. The organic phase was separated, washed with 5% $NaHCO_3$, dried over $Na_2SO_4$, and concentrated in vacuo to give 1-(4-iodophenyl)-1H-pyrrole-3-carbaldehyde (0.927 g).

To a suspension of 1-(4-iodophenyl)-1H-pyrrole-3-carbaldehyde (927 mg, 3.12 mmol) in MeOH (15 mL) at room temperature was added $NaBH_4$ (142 mg, 3.74 mmol). The mixture was stirred at room temperature for 10 min, during which time the suspension became clear. The solvent was removed in vacuo. The residue was partitioned between $H_2O$ and EtOAc. The organic phase was separated, washed with 1N HCl, 1N NaOH and brine, dried over $Na_2SO_4$, and concentrated in vacuo to give the alcohol (877 mg).

To a solution of the alcohol (220 mg, 0.736 mmol) and diphenyl phosphoryl azide (0.174 mL, 0.808 mmol) in THF (5 mL) was added DBU (0.110 mL, 0.737 mmol). The mixture was stirred at room temperature overnight. It was concentrated in vacuo. The residue was purified by HPLC to give the azide (124 mg).

A mixture of the azide (124 mg, 0.38 mmol) and Ra—Ni (50% aq. slurry, 100 mg) in MeOH (8 mL) was hydrogenated under balloon $H_2$ for 3 h. It was then filtered through celite, and filtrate was concentrated in vacuo to give (1-(4-iodophenyl)-1H-pyrrol-3-yl)methanamine (91 mg).

To a solution of 5-chloro-thiophene-2-carboxylic acid (60 mg, 0.37 mmol) and TEA (0.102 mL, 0.73 mmol) in DMF (4 mL) was added BOP (196 mg, 0.44 mmol). After 10 min of stirring, the solution was added to a sample of (1-(4-iodophenyl)-1H-pyrrol-3-yl)methanamine (91 mg, 0.31 mmol) in a flask. The mixture was stirred at room temperature overnight. $H_2O$ was added to induce precipitation. The resulting precipitate was collected and dried on vacuum to give 5-chloro-N-((1-(4-iodophenyl)-1H-pyrrol-3-yl)methyl)thiophene-2-carboxamide (118 mg).

A mixture of 5-chloro-N-((1-(4-iodophenyl)-1H-pyrrol-3-yl)methyl)thiophene-2-carboxamide (118 mg, 0.27 mmol), 2-hydroxypyridine (50 mg, 0.53 mmol), 8-hydroxyquinoline (14 mg, 0.097 mmol) and $K_2CO_3$ (120 mg, 0.87 mmol) in DMSO (2 mL) was degassed with Argon before being charged with CuI (19 mg, 0.10 mmol). The mixture in a sealed tube was heated at 130° C. for 4 h. It was then purified by HPLC to give the titled compound (20 mg). MS 410.0 and 412.0 (M+H, Cl pattern).

Example 66

5-Chloro-N-((1-(4-(2-oxopyridin-1(2H)-yl)phenyl)-1H-pyrazol-4-yl)methyl)thiophene-2-carboxamide (109)

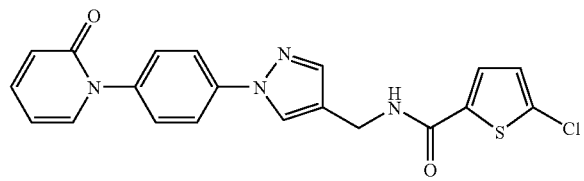

A mixture of 1,4-diiodobenzene (4.00 g, 12.1 mmol), 4-methylpyrazole (0.972 g, 12.1 mmol), 8-hydroxyquinoline (0.176 g, 1.21 mmol) and $K_2CO_3$ (1.69 g, 12.2 mmol) in DMSO (12 mL) was degassed before being charged with CuI (0.310 g, 1.63 mmol). The mixture in a sealed tube was heated at 130° C. overnight. Water and EtOAc were added. The mixture was filtered. The organic layer was separated, then applied to a silica gel column, which was eluted with hexane, then with 5% EtOAc in hexane to give 1-(4-iodophenyl)-4-methyl-1H-pyrazole (1.70 g).

A mixture of 1-(4-iodophenyl)-4-methyl-1H-pyrazole (1.70 g, 5.99 mmol), NBS (1.38 g, 7.75 mmol) and AIBN (0.30 g, 1.83 mmol) in $CCl_4$ (25 mL) was heated at reflux for 1 hr. After being cooled to room temperature, the upper clear solution was decanted out and concentrated in vacuo. The residue was dissolved in DMF (10 mL), $NaN_3$ (0.934 g, 14.3 mmol) was added. The mixture was stirred at room temperature overnight. $H_2O$ and EtOAc were added. The organic phase was separated, dried over $Na_2SO_4$, concentrated in vacuo. The residue was purified by a silica gel column, eluted with hexane, then with 5% EtOAc in hexane to give 4-(azidomethyl)-1-(4-iodophenyl)-1H-pyrazole (0.70 g).

A mixture of 4-(azidomethyl)-1-(4-iodophenyl)-1H-pyrazole (530 mg, 1.63 mmol) and Ra—Ni (50% aq. slurry, 200 mg) in MeOH (3 mL) was hydrogenated under balloon $H_2$ for 1 hr. It was filtered through celite. The filtrate was concentrated in vacuo to give (1-(4-iodophenyl)-1H-pyrazol-4-yl)methanamine (396 mg).

To a solution of 5-chloro-thiophene-2-carboxylic acid (237 mg, 1.46 mmol), (1-(4-iodophenyl)-1H-pyrazol-4-yl)methanamine (396 mg, 1.32 mmol) and TEA (0.500 mL, 3.59 mmol) in DMF (10 mL), BOP (828 mg, 1.87 mmol) were added. The mixture was stirred at room temperature overnight. $H_2O$ and EtOAc were added. The organic phase was separated, washed with 5% $NaHCO_3$, dried over $Na_2SO_4$, concentrated in vacuo to give 5-chloro-N-((1-(4-iodophenyl)-1H-pyrazol-4-yl)methyl)thiophene-2-carboxamide (462 mg).

A mixture of 5-chloro-N-((1-(4-iodophenyl)-1H-pyrazol-4-yl)methyl)thiophene-2-carboxamide (200 mg, 0.451 mmol), 2-hydroxypyridine (85 mg, 0.90 mmol), 8-hydroxyquinoline (30 mg, 0.21 mmol) and $K_2CO_3$ (247 mg, 1.79 mmol) in DMSO (2 mL) was degassed with Argon before being charged with CuI (43 mg, 0.22 mmol). The mixture in a sealed tube was heated at 130° C. overnight. It was then purified by HPLC to give the title compound (60 mg). MS 411.0 and 413.0 (M+H, Cl pattern).

Example 67

5-Chloro-N-((1-(4-(4-methyl-1,4-diazepan-1-yl)phenyl)-1H-pyrazol-4-yl)methyl)thiophene-2-carboxamide (110)

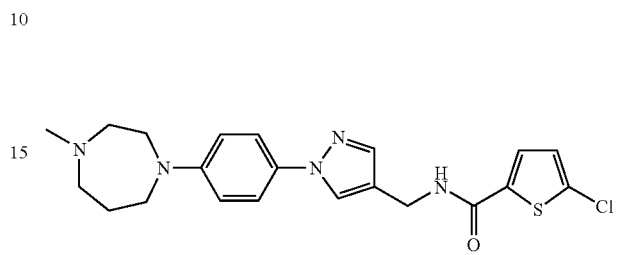

A mixture of 5-chloro-N-((1-(4-iodophenyl)-1H-pyrazol-4-yl)methyl)thiophene-2-carboxamide (100 mg, 0.225 mmol), 1-methylhomopiperazine (0.100 mL, 0.81 mmol), ethylene glycol (0.025 mL, 0.45 mmol) and $K_3PO_4$ (100 mg, 0.47 mmol) in isopropanol (1 mL) was degassed with Argon before being charged with CuI (20 mg, 0.11 mmol). The mixture in a sealed tube was heated at 85° C. overnight. It was then purified by HPLC to give the title compound (5 mg). MS 430.0 and 432.0 (M+H, Cl pattern).

Example 68

5-Chloro-N-((1-(4-(2-oxopyrazin-1(2H)-yl)phenyl)-1H-pyrazol-4-yl)methyl)thiophene-2-carboxamide (111)

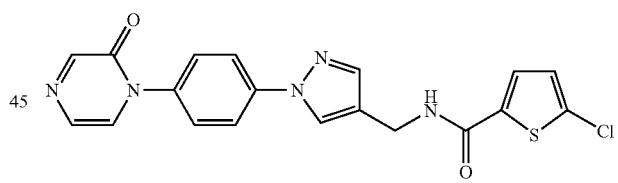

To a solution of glycinamide hydrochloride (1.10 g, 10.0 mmol) in 5 N NaOH (6 mL) at room temperature, glyoxal (40% in $H_2O$, 1.5 mL, 13.1 mmol) was added. The solution was stirred at room temperature overnight. The product was extracted from the aqueous solution with nBuOH, and nBuOH extract was concentrated in vacuo to give 2-hydroxypyrazine as a white solid (0.20 g).

A mixture of 5-chloro-N-((1-(4-iodophenyl)-1H-pyrazol-4-yl)methyl)thiophene-2-carboxamide (75 mg, 0.17 mmol), 2-hydroxypyrazine (43 mg, 0.45 mmol), 8-hydroxyquinoline (15 mg, 0.10 mmol) and $K_2CO_3$ (100 mg, 0.72 mmol) in DMSO (1 mL) was degassed with Argon before being charged with CuI (19 mg, 0.10 mmol). The mixture in a sealed tube was heated at 130° C. overnight. It was then purified by HPLC to give the title compound (10 mg). MS 412.0 and 414.0 (M+H, Cl pattern).

Example 69

5-Chloro-N-((1-(4-(2-oxopyridin-1(2H)-yl)phenyl)-1H-pyrazol-3-yl)methyl)thiophene-2-carboxamide (112)

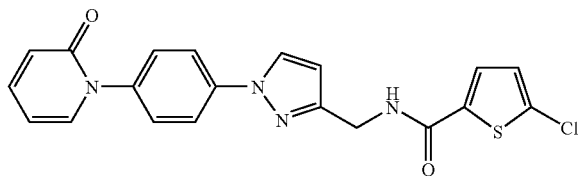

A mixture of 1,4-diiodobenzene (4.00 g, 12.1 mmol), 3-methylpyrazole (0.972 g, 12.1 mmol), 8-hydroxyquinoline (0.176 g, 1.21 mmol) and $K_2CO_3$ (1.69 g, 12.2 mmol) in DMSO (12 mL) was degassed before being charged with CuI (0.230 g, 1.21 mmol). The mixture in a sealed tube was heated at 130° C. overnight. Water and EtOAc were added. The mixture was filtered. The organic layer was separated, then purified by silica gel column chromatography with hexane followed by 4-6% EtOAc in hexane to give 1-(4-iodophenyl)-3-methyl-1H-pyrazole (0.98 g).

A mixture of 1-(4-iodophenyl)-3-methyl-1H-pyrazole (0.98 g, 3.45 mmol), NBS (0.80 g, 4.49 mmol) and AIBN (0.17 g, 1.03 mmol) in $CCl_4$ (15 mL) was heated at reflux for 5 hrs. After being cooled to room temperature, it was filtered. The filtrate was concentrated in vacuo. The residue was dissolved in DMF (8 mL), $NaN_3$ (0.400 g, 6.15 mmol) was added. The mixture was stirred at room temperature overnight. $H_2O$ and EtOAc were added. The organic phase was separated, dried over $Na_2SO_4$, concentrated in vacuo. The residue was purified by a silica gel column, eluted with hexane, then with 4-6% EtOAc in hexane to give 3-(azidomethyl)-1-(4-iodophenyl)-1H-pyrazole (0.10 g).

A mixture of 3-(azidomethyl)-1-(4-iodophenyl)-1H-pyrazole (100 mg, 0.31 mmol) and Ra—Ni (50% aq. slurry, 150 mg) in MeOH (8 mL) was hydrogenated under balloon $H_2$ for 3 hrs. It was filtered through celite. The filtrate was concentrated in vacuo to give (1-(4-iodophenyl)-1H-pyrazol-3-yl)methanamine (78 mg).

To a solution of 5-chloro-thiophene-2-carboxylic acid (51 mg, 0.31 mmol), (1-(4-iodophenyl)-1H-pyrazol-3-yl)methanamine (78 mg, 0.26 mmol) and TEA (0.100 mL, 0.72 mmol) in DMF (3 mL), BOP (170 mg, 0.38 mmol) was added. The mixture was stirred at room temperature overnight. $H_2O$ and EtOAc were added. The organic phase was separated, washed with 5% $NaHCO_3$, dried over $Na_2SO_4$, concentrated in vacuo. The residue was purified by a preparative TLC plate (developed in EtOAc/hexane (35/65)) to give 5-chloro-N-((1-(4-iodophenyl)-1H-pyrazol-3-yl)methyl)thiophene-2-carboxamide (60 mg).

A mixture of 5-chloro-N-((1-(4-iodophenyl)-1H-pyrazol-3-yl)methyl)thiophene-2-carboxamide (60 mg, 0.14 mmol), 2-hydroxypyridine (30 mg, 0.32 mmol), 8-hydroxyquinoline (10 mg, 0.070 mmol) and $K_2CO_3$ (50 mg, 0.36 mmol) in DMSO (1 mL) was degassed with Argon before being charged with CuI (15 mg, 0.080 mmol). The mixture in a sealed tube was heated at 130° C. overnight. It was then purified by HPLC to give the titled compound (15 mg). MS 411.0 and 413.0 (M+H, Cl pattern).

Example 70

5-Chloro-N-((1-(3-methoxy-4-(2-oxopyridin-1(2H)-yl)phenyl)-1H-1,2,3-triazol-4-yl)methyl)thiophene-2-carboxamide (115)

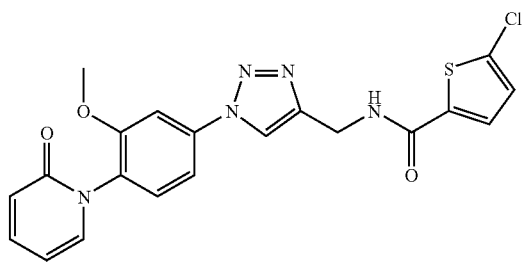

The title compound was prepared using a similar procedure as described in Example 1 for preparing compound 1.6. MS found for $C_{20}H_{16}ClN_5O_3S$ (M+H)+ 442.1, 444.1.

The compounds in the following Table 2 were prepared using methods similar to those above or using methods similar to those disclosed in U.S. patent application Ser. No. 11/158,274, filed Jun. 20, 2005, which claims the benefit of U.S. Provisional Application No. 60/580,899, filed Jun. 18, 2004, which applications are incorporated herein by reference in their entireties.

TABLE 2

| Compound | Structure | Name | MS |
|---|---|---|---|
| 7 | 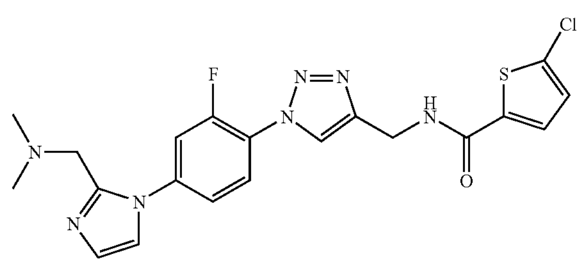 | 5-Chloro-N-((1-(4-(2-((dimethylamino)methyl)-1H-imidazol-1-yl)-2-fluorophenyl)-1H-1,2,3-triazol-4-yl)methyl)thiophene-2-carboxamide | 460.1 |

TABLE 2-continued

| Compound | Structure | Name | MS |
|---|---|---|---|
| 8 | 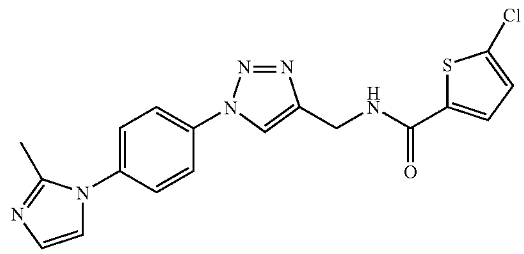 | 5-Chloro-N-((1-(4-(2-methyl-1H-imidazol-1-yl)phenyl)-1H-1,2,3-triazol-4-yl)methyl)thiophene-2-carboxamide | 399.1 |
| 10 | 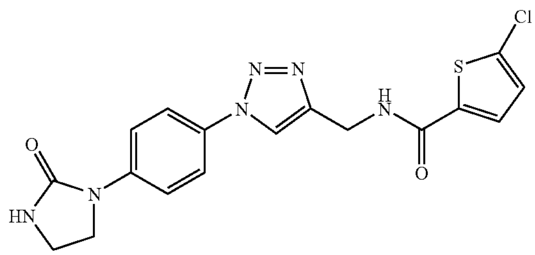 | 5-Chloro-N-((1-(4-(2-oxoimidazolidin-1-yl)phenyl)-1H-1,2,3-triazol-4-yl)methyl)thiophene-2-carboxamide | 403.1 |
| 15 | 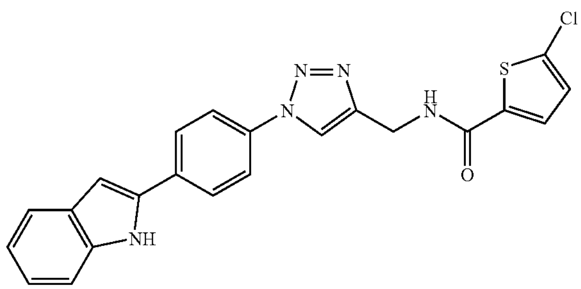 | N-((1-(4-(1H-Indol-2-yl)phenyl)-1H-1,2,3-triazol-4-yl)methyl)-5-chlorothiophene-2-carboxamide | 434 |
| 16 | 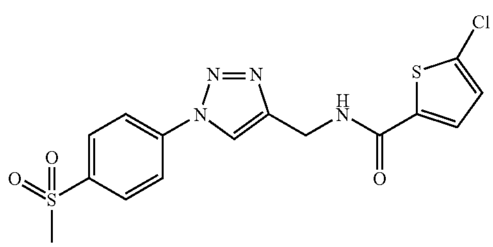 | 5-Chloro-N-((1-(4-(methylsulfonyl)phenyl)-1H-1,2,3-triazol-4-yl)methyl)thiophene-2-carboxamide | 397.0 |
| 17 | 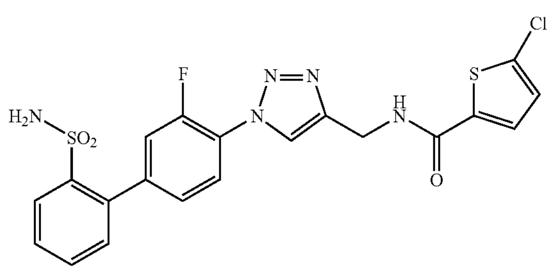 | 5-Chloro-N-((1-(3-fluoro-2'-sulfamoylbiphenyl-4-yl)-1H-1,2,3-triazol-4-yl)methyl)thiophene-2-carboxamide | 492.0 |
| 20 | 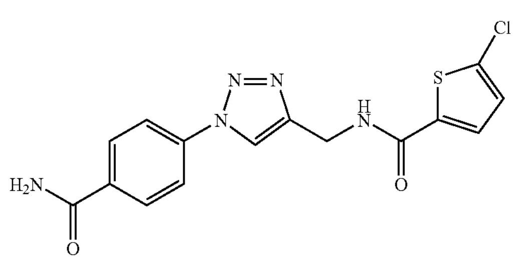 | N-((1-(4-Carbamoylphenyl)-1H-1,2,3-triazol-4-yl)methyl)-5-chlorothiophene-2-carboxamide | 362.0 |

TABLE 2-continued

| Compound | Structure | Name | MS |
|---|---|---|---|
| 22 | 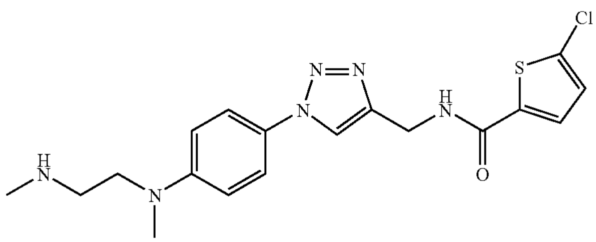 | 5-Chloro-N-((1-(4-(methyl(2-(methylamino)ethyl)amino)phenyl)-1H-1,2,3-triazol-4-yl)methyl)thiophene-2-carboxamide | 405.1 |
| 23 | 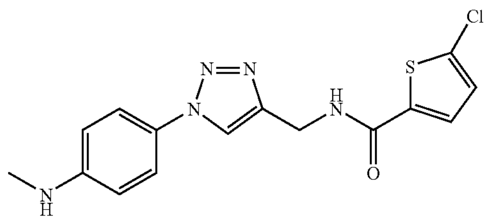 | 5-Chloro-N-((1-(4-(methylamino)phenyl)-1H-1,2,3-triazol-4-yl)methyl)thiophene-2-carboxamide | 348.1 |
| 29 | 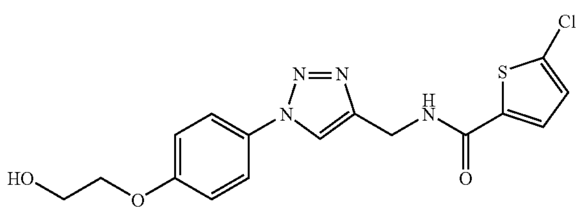 | 5-Chloro-N-((1-(4-(2-hydroxyethoxy)phenyl)-1H-1,2,3-triazol-4-yl)methyl)thiophene-2-carboxamide | 379.1 |
| 41 | 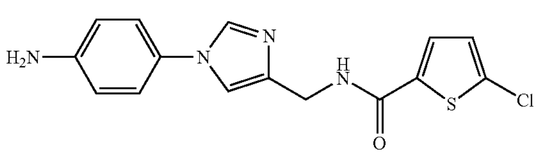 | N-((1-(4-Aminophenyl)-1H-imidazol-4-yl)methyl)-5-chlorothiophene-2-carboxamide | 333.0 |
| 42 | 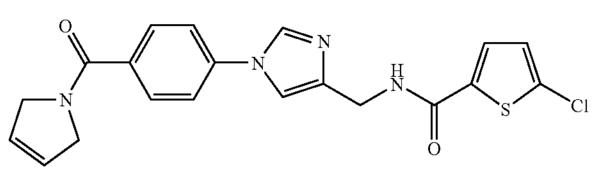 | 5-Chloro-N-((1-(4-(2,5-dihydro-1H-pyrrole-1-carbonyl)phenyl)-1H-imidazol-4-yl)methyl)thiophene-2-carboxamide | 413.1 |
| 44 | 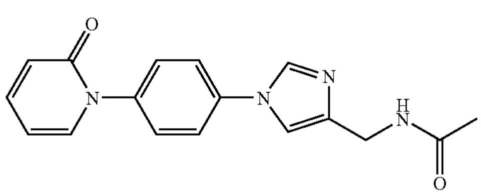 | N-((1-(4-(2-Oxopyridin-1(2H)-yl)phenyl)-1H-imidazol-4-yl)methyl)acetamide | 309.1 |
| 47 | 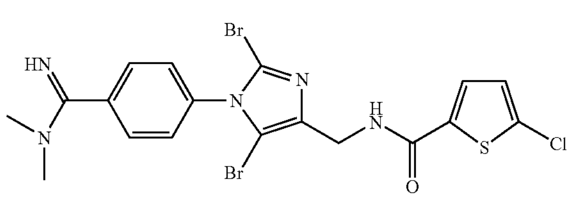 | 5-Chloro-N-((2,5-dibromo-1-(4-(N,N-dimethylcarbamimidoyl)phenyl)-1H-imidazol-4-yl)methyl)thiophene-2-carboxamide | 544.0, 546.0, 548.0 |

TABLE 2-continued

| Compound | Structure | Name | MS |
|---|---|---|---|
| 48 | 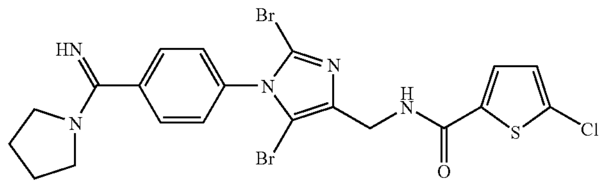 | 5-Chloro-N-((2,5-dibromo-1-(4-(imino(pyrrolidin-1-yl)methyl)phenyl)-1H-imidazol-4-yl)methyl)thiophene-2-carboxamide | 570.0, 572.0, 574.0 |
| 49 | 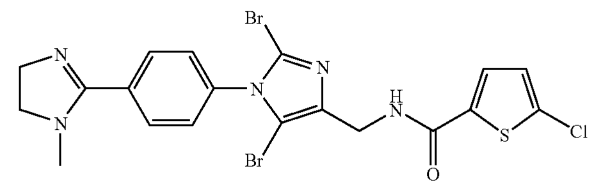 | 5-Chloro-N-((2,5-dibromo-1-(4-(1-methyl-4,5-dihydro-1H-imidazol-2-yl)phenyl)-1H-imidazol-4-yl)methyl)thiophene-2-carboxamide | 556.0, 558.0, 560.0 |
| 50 | 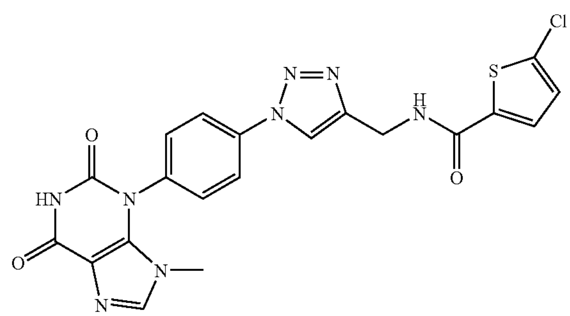 | 5-Chloro-N-((1-(4-(9-methyl-2,6-dioxo-1H-purin-3(2H,6H,9H)-yl)phenyl)-1H-1,2,3-triazol-4-yl)methyl)thiophene-2-carboxamide | 483.1 |
| 52 | 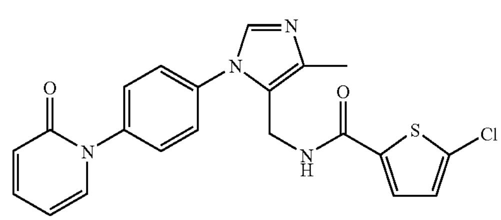 | 5-Chloro-N-((4-methyl-1-(4-(2-oxopyridin-1(2H)-yl)phenyl)-1H-imidazol-5-yl)methyl)thiophene-2-carboxamide | 425.1 |
| 53 | 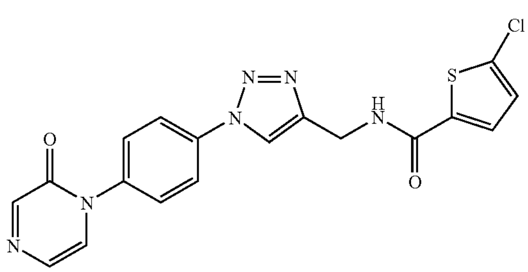 | 5-Chloro-N-((1-(4-(2-oxopyrazin-1(2H)-yl)phenyl)-1H-1,2,3-triazol-4-yl)methyl)thiophene-2-carboxamide | 413.1 |
| 56 | 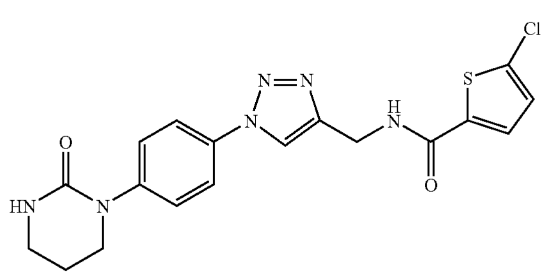 | 5-Chloro-N-((1-(4-(2-oxotetrahydropyrimidin-1(2H)-yl)phenyl)-1H-1,2,3-triazol-4-yl)methyl)thiophene-2-carboxamide | 417.1 |

TABLE 2-continued

| Compound | Structure | Name | MS |
|---|---|---|---|
| 76 | 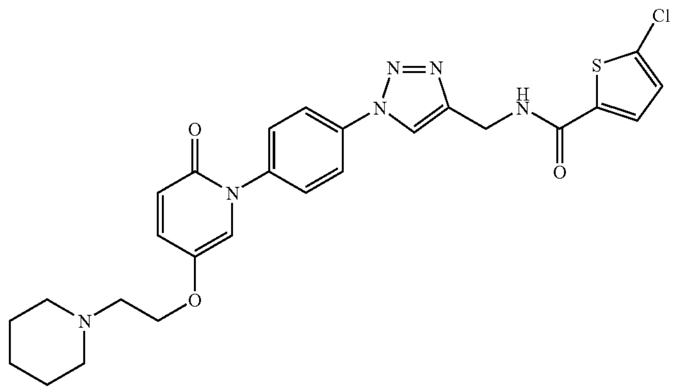 | 5-Chloro-N-((1-(4-(2-oxo-5-(2-(piperidin-1-yl)ethoxy)pyridin-1(2H)-yl)phenyl)-1H-1,2,3-triazol-4-yl)methyl)thiophene-2-carboxamide | 539.1 |
| 77 | 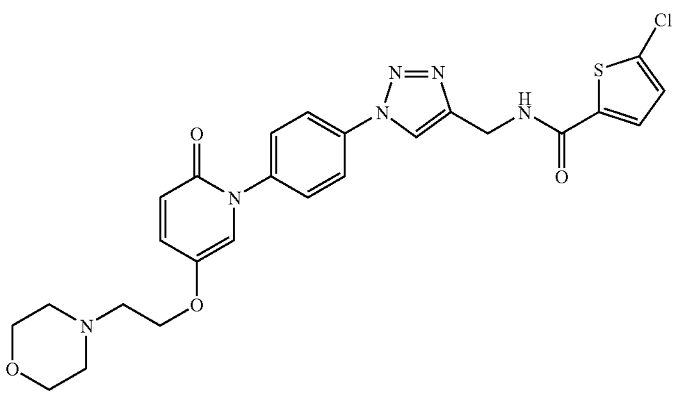 | 5-Chloro-N-((1-(4-(5-(2-morpholinoethoxy)-2-oxopyridin-1(2H)-yl)phenyl)-1H-1,2,3-triazol-4-yl)methyl)thiophene-2-carboxamide | 541.1 |
| 78 | 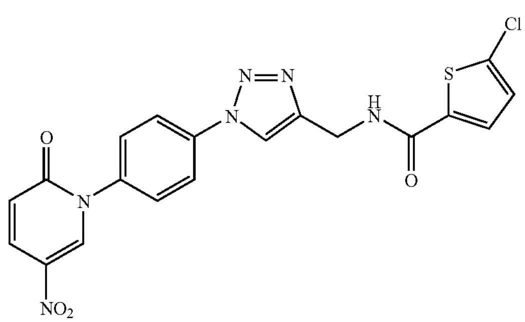 | 5-Chloro-N-((1-(4-(5-nitro-2-oxopyridin-1(2H)-yl)phenyl)-1H-1,2,3-triazol-4-yl)methyl)thiophene-2-carboxamide | 457 |
| 88 | 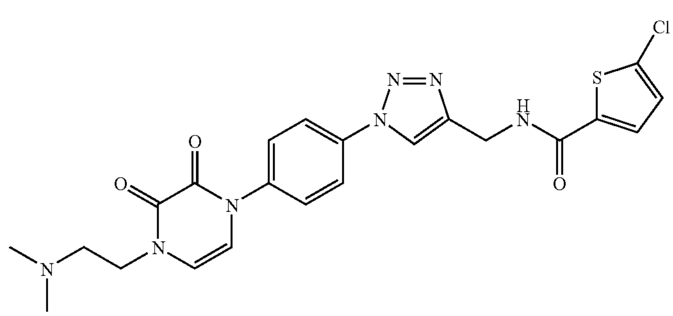 | 5-Chloro-N-((1-(4-(4-(2-(dimethylamino)ethyl)-2,3-dioxo-3,4-dihydropyrazin-1(2H)-yl)phenyl)-1H-1,2,3-triazol-4-yl)methyl)thiophene-2-carboxamide | 500.1 |

TABLE 2-continued

| Compound | Structure | Name | MS |
|---|---|---|---|
| 89 | 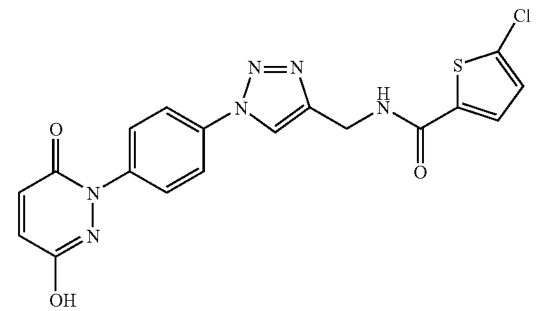 | 5-Chloro-N-((1-(4-(3-hydroxy-6-oxopyridazin-1(6H)-yl)phenyl)-1H-1,2,3-triazol-4-yl)methyl)thiophene-2-carboxamide | 429.1 |
| 90 | 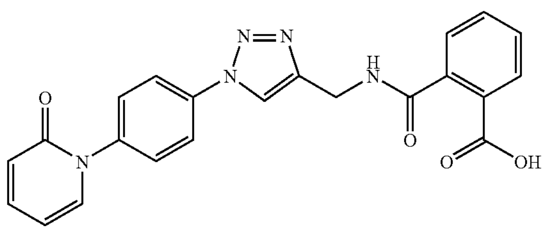 | 2-((1-(4-(2-Oxopyridin-1(2H)-yl)phenyl)-1H-1,2,3-triazol-4-yl)methylcarbamoyl)benzoic acid | 414.1 |
| 91 | 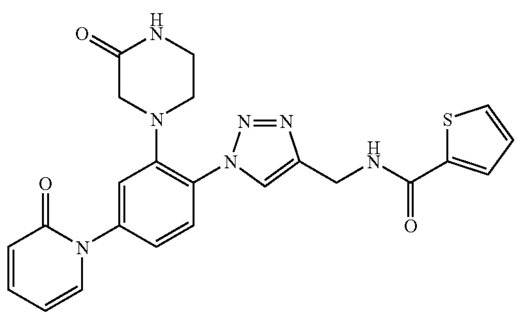 | N-((1-(2-(3-Oxopiperazin-1-yl)-4-(2-oxopyridin-1(2H)-yl)phenyl)-1H-1,2,3-triazol-4-yl)methyl)thiophene-2-carboxamide | 476.1 |
| 92 | 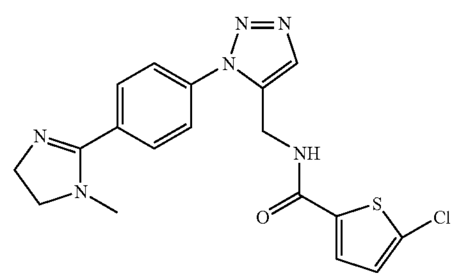 | 5-Chloro-N-((1-(4-(1-methyl-4,5-dihydro-1H-imidazol-2-yl)phenyl)-1H-1,2,3-triazol-5-yl)methyl)thiophene-2-carboxamide | 401.1 |
| 93 | 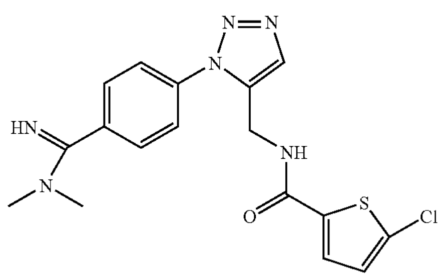 | 5-Chloro-N-((1-(4-(N,N-dimethylcarbamimidoyl)phenyl)-1H-1,2,3-triazol-5-yl)methyl)thiophene-2-carboxamide | 389.1 |

TABLE 2-continued

| Compound | Structure | Name | MS |
|---|---|---|---|
| 94 | 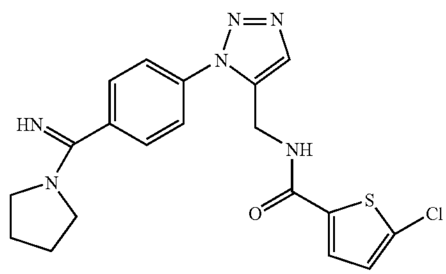 | 5-Chloro-N-((1-(4-(imino(pyrrolidin-1-yl)methyl)phenyl)-1H-1,2,3-triazol-5-yl)methyl)thiophene-2-carboxamide | 415.1 |
| 95 | 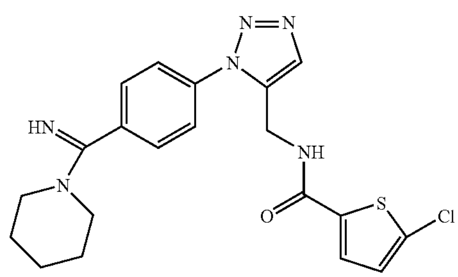 | 5-Chloro-N-((1-(4-(imino(piperidin-1-yl)methyl)phenyl)-1H-1,2,3-triazol-5-yl)methyl)thiophene-2-carboxamide | 429.1 |
| 96 | 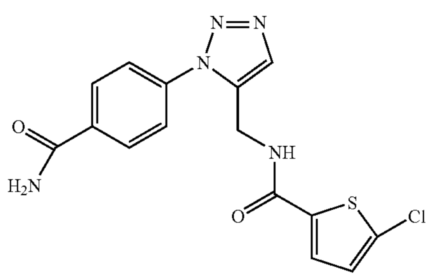 | N-((1-(4-Carbamoylphenyl)-1H-1,2,3-triazol-5-yl)methyl)-5-chlorothiophene-2-carboxamide | 362.0 |
| 97 | 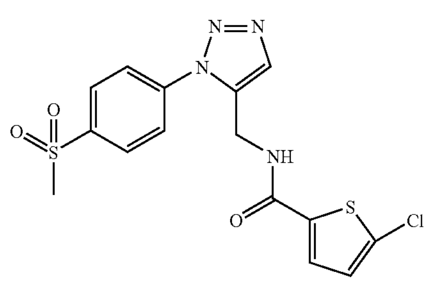 | 5-Chloro-N-((1-(4-(methylsulfonyl)phenyl)-1H-1,2,3-triazol-5-yl)methyl)thiophene-2-carboxamide | 397.0 |
| 98 | 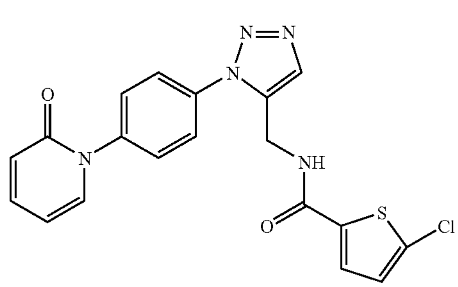 | 5-Chloro-N-((1-(4-(2-oxopyridin-1(2H)-yl)phenyl)-1H-1,2,3-triazol-5-yl)methyl)thiophene-2-carboxamide | 412.1 |

TABLE 2-continued

| Compound | Structure | Name | MS |
|---|---|---|---|
| 99 | 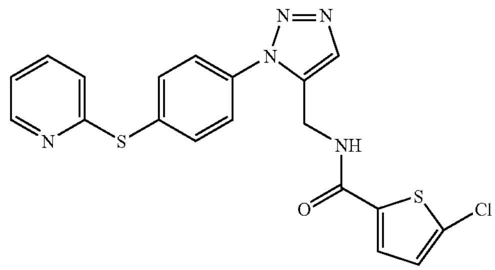 | 5-Chloro-N-((1-(4-(pyridin-2-ylthio)phenyl)-1H-1,2,3-triazol-5-yl)methyl)thiophene-2-carboxamide | 428.0 |
| 100 | 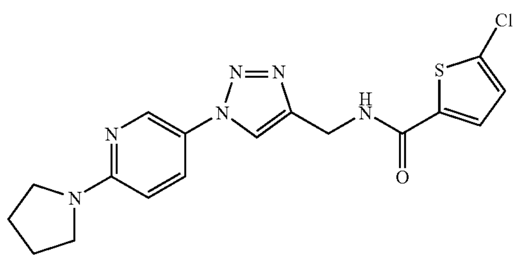 | 5-Chloro-N-((1-(6-(pyrrolidin-1-yl)pyridin-3-yl)-1H-1,2,3-triazol-4-yl)methyl)thiophene-2-carboxamide | 389.1 |
| 101 | 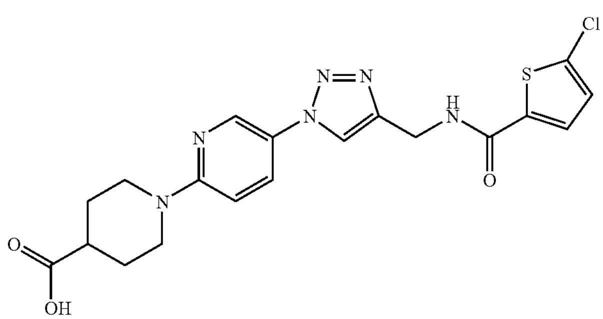 | 1-(5-(4-((5-Chlorothiophene-2-carboxamido)methyl)-1H-1,2,3-triazol-1-yl)pyridin-2-yl)piperidine-4-carboxylic acid | 447.1 |
| 102 | 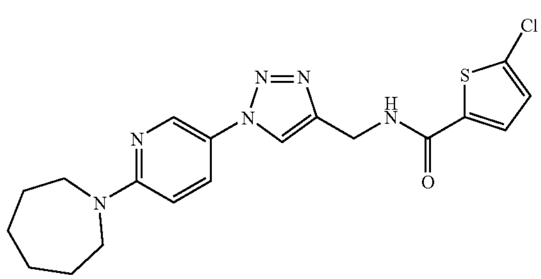 | N-((1-(6-(Azepan-1-yl)pyridin-3-yl)-1H-1,2,3-triazol-4-yl)methyl)-5-chlorothiophene-2-carboxamide | 417.1 |
| 103 | 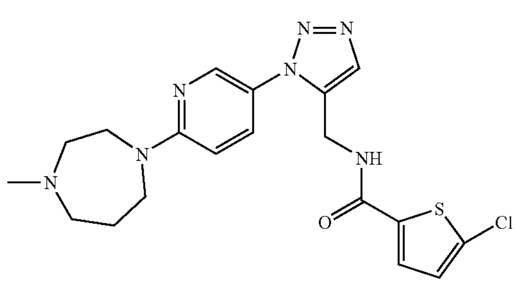 | 5-Chloro-N-((1-(6-(4-methyl-1,4-diazepan-1-yl)pyridin-3-yl)-1H-1,2,3-triazol-5-yl)methyl)thiophene-2-carboxamide | 432.1 |

TABLE 2-continued

| Compound | Structure | Name | MS |
|---|---|---|---|
| 104 | 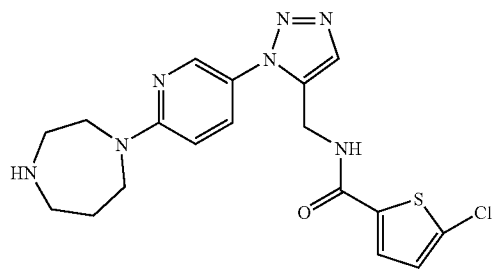 | N-((1-(6-(1,4-Diazepan-1-yl)pyridin-3-yl)-1H-1,2,3-triazol-5-yl)methyl)-5-chlorothiophene-2-carboxamide | 418.1 |
| 105 | 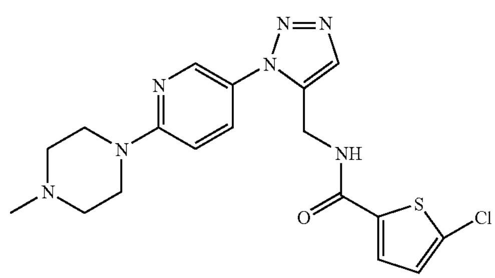 | 5-Chloro-N-((1-(6-(4-methylpiperazin-1-yl)pyridin-3-yl)-1H-1,2,3-triazol-5-yl)methyl)thiophene-2-carboxamide | 418.1 |
| 106 | 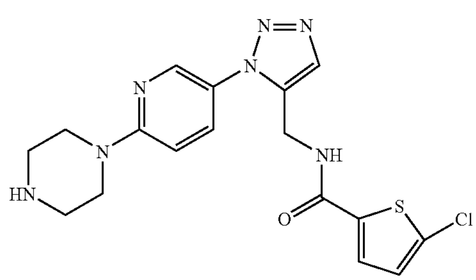 | 5-Chloro-N-((1-(6-(piperazin-1-yl)pyridin-3-yl)-1H-1,2,3-triazol-5-yl)methyl)thiophene-2-carboxamide | 404.1 |
| 107 | 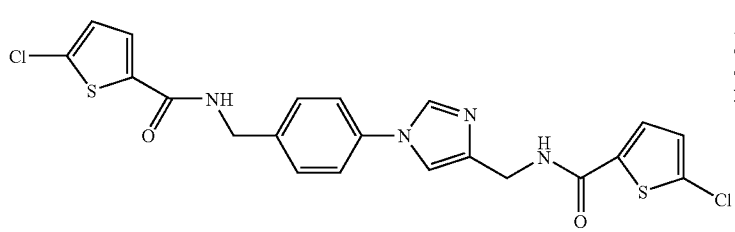 | 5-Chloro-N-(4-(4-((5-chlorothiophene-2-carboxamido)methyl)-1H-imidazol-1-yl)benzyl)thiophene-2-carboxamide | 491.0, 493.0 |
| 113 | 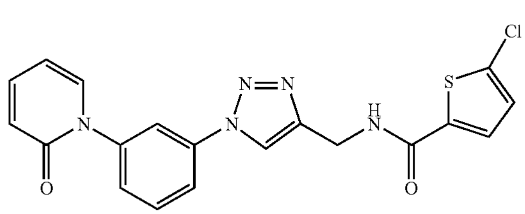 | 5-Chloro-N-((1-(3-(2-oxopyridin-1(2H)-yl)phenyl)-1H-1,2,3-triazol-4-yl)methyl)thiophene-2-carboxamide | 412.1 |

TABLE 2-continued

| Compound | Structure | Name | MS |
|---|---|---|---|
| 114 | 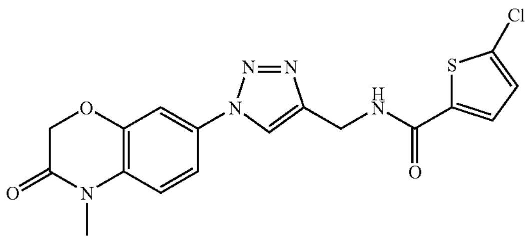 | 5-Chloro-N-((1-(4-methyl-3-oxo-3,4-dihydro-2H-benzo[β][1,4]oxazin-7-yl)-1H-1,2,3-triazol-4-yl)methyl)thiophene-2-carboxamide | 404 |
| 116 | 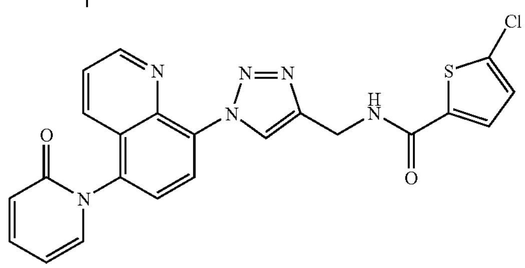 | 5-Chloro-N-((1-(5-(2-oxopyridin-1(2H)-yl)quinolin-8-yl)-1H-1,2,3-triazol-4-yl)methyl)thiophene-2-carboxamide | 463 |

Example 71

This example illustrates methods for evaluating the compounds of the invention, along with results obtained for such assays. The in vitro and in vivo human Factor Xa activities of the inventive compounds can be determined by various procedures known in the art, such as a test for their ability to inhibit the activity of human plasma Factor Xa. The potent affinities for human Factor Xa inhibition exhibited by the inventive compounds can be measured by an $IC_{50}$ value (in nM). The $IC_{50}$ value is the concentration (in nM) of the compound required to provide 50% inhibition of human Factor Xa proteolytic activity. The smaller the $IC_{50}$ value, the more active (potent) is a compound for inhibiting Factor Xa activity.

An in vitro assay for detecting and measuring inhibition activity against Factor Xa is as follows:

$IC_{50}$ and Ki Determinations:

Substrate:

The substrate S-2765 (Z-D-Arg-Gly-Arg-pNA-HCl) was obtained from Diapharma (West Chester, Ohio).

Enzyme:

The human plasma protein factor Xa was purchased from Haematologic Technologies (Essex Junction, Vt.).

Methods $IC_{50}$ determinations

All assays, which are performed in 96-well microtiter plates, measure proteolytic activity of the enzyme (factor Xa) by following cleavage of a paranitroanilide peptide substrate. The assay buffer used for proteolytic assays was Tris buffered saline (20 mM Tris, 150 mM NaCl, 5 mM $CaCl_2$, 0.1% Bovine serum albumin (BSA), 5% Dimethyl Sulfoxide (DMSO) pH 7.4). In a 96-well microtiter plate, inhibitor was serially diluted to give a range of final concentrations from 0.01 nM to 10 μM. Duplicate sets of wells were assayed and control wells without inhibitor were included. Enzyme was added to each well, (factor Xa concentration=1 nM), the plate was shaken for 5 seconds and then incubated for 5 minutes at room temperature. S-2765 was added (100 μM final) and the plate was shaken for 5 seconds (final volume in each well was 200 μl). The degree of substrate hydrolysis was measured at 405 nm on a Thermomax plate reader (Molecular Devices, Sunnyvale, Calif.) for 2 minutes. The initial velocities of substrate cleavage (mOD/min), for each range of inhibitor concentrations, were fitted to a four parameter equation using Softmax data analysis software. The parameter C, derived from the resulting curve-fit, corresponded to the concentration for half maximal inhibition ($IC_{50}$).

$K_i$ determination

The assay buffer for this series of assays was Hepes buffered saline (20 mM Hepes, 150 mM NaCl, 5 mM $CaCl_2$, 0.1% PEG-8000, pH 7.4). In a 96-well microtiter plate, inhibitor was serially diluted in a duplicate set of wells to give a range of final concentrations from 5 pM to 3 μM. Controls without inhibitor (8 wells) were included. The enzyme, factor Xa (final concentration=1 nM) was added to the wells. The substrate S-2765 (final concentration=200 μM) was added and the degree of substrate hydrolysis was measured at 405 nm on a Thermomax plate reader for 5 minutes, using Softmax software. Initial velocities (mOD/min) were analyzed by non-linear least squares regression in the Plate Ki software (BioKin Ltd, Pullman, Wash.) (Kusmic, et al., *Analytical Biochemistry* 281: 62-67, 2000). The model used for fitting the inhibitor dose-response curves was the Morrison equation. An apparent $K_i$ (Ki*) was determined. The overall $K_i$ was calculated using the following equation:

$$Ki = \frac{Ki^*}{1 + \frac{[S]}{Km}}$$

where [S] is substrate concentration (200 μM) and $K_m$ is the Michaelis constant for S-2765.

The following compounds exhibited Factor Xa IC$_{50}$ values less than or equal to 100 nM: 1, 3, 4, 7-9, 18, 19, 21, 22, 27, 28, 39, 40, 42, 45, 47-49, 53, 56, 59, 60, 62-74, 79-83, 86, 87, 98, 115.

The following compounds exhibited Factor Xa IC$_{50}$ values greater than 100 nM and less than 500 nM: 5, 6, 10, 20, 24-26, 37, 46, 61, 78, 100, 102.

The following compounds exhibited Factor Xa IC$_{50}$ values greater than or equal to 500 nM: 11-17, 23, 29, 38, 41, 43, 44, 50-52, 75-77, 84, 85, 88-97, 99, 101, 103-106, 113, 114, 116.

What is claimed is:

1. A compound of Formula (I) or a pharmaceutically acceptable salt, ester thereof:

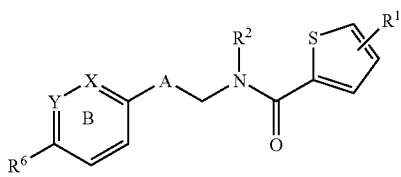

(I)

wherein:
R$^1$ is halogen;
R$^2$ is hydrogen or C$_{1-4}$ alkyl;
A is selected from the group consisting of:

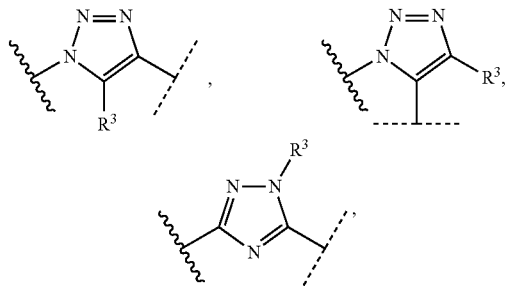

wherein the wavy line indicates the point of attachment to ring B and the dashed line indicates the point of attachment to the rest of the molecule;
R$^3$ is hydrogen or R$^{3a}$;
R$^{3a}$ is selected from the group consisting of halogen, C$_{1-8}$ alkyl, C$_{2-8}$ alkenyl, and C$_{2-8}$ alkynyl;
X is C-R$^4$ or N;
Y is C-R$^5$ or N provided that X and Y are not both N;
R$^4$ is selected from the group consisting of hydrogen, halogen, and

R$^{4a}$ is hydrogen or C$_{1-8}$ alkyl;
R$^5$ is selected from the group consisting of hydrogen, halogen, and C$_{1-8}$ alkoxy;
R$^6$ is selected from the group consisting of —R$^{6a}$, —NR$^{7a}$R$^{7b}$, —NR$^{7a}$C(O)R$^{7c}$, —NR$^{7a}$C(O)OR$^{7c}$, —CONR$^{8a}$R$^{8b}$, —OR$^{7c}$, —SR$^{7c}$, —C(=NR$^{7a}$)NR$^{8a}$R$^{8b}$, —S(O)$_2$NR$^{8a}$R$^{8b}$, and —S(O)$_2$R$^{7c}$;

R$^{6a}$ is selected from the group consisting of

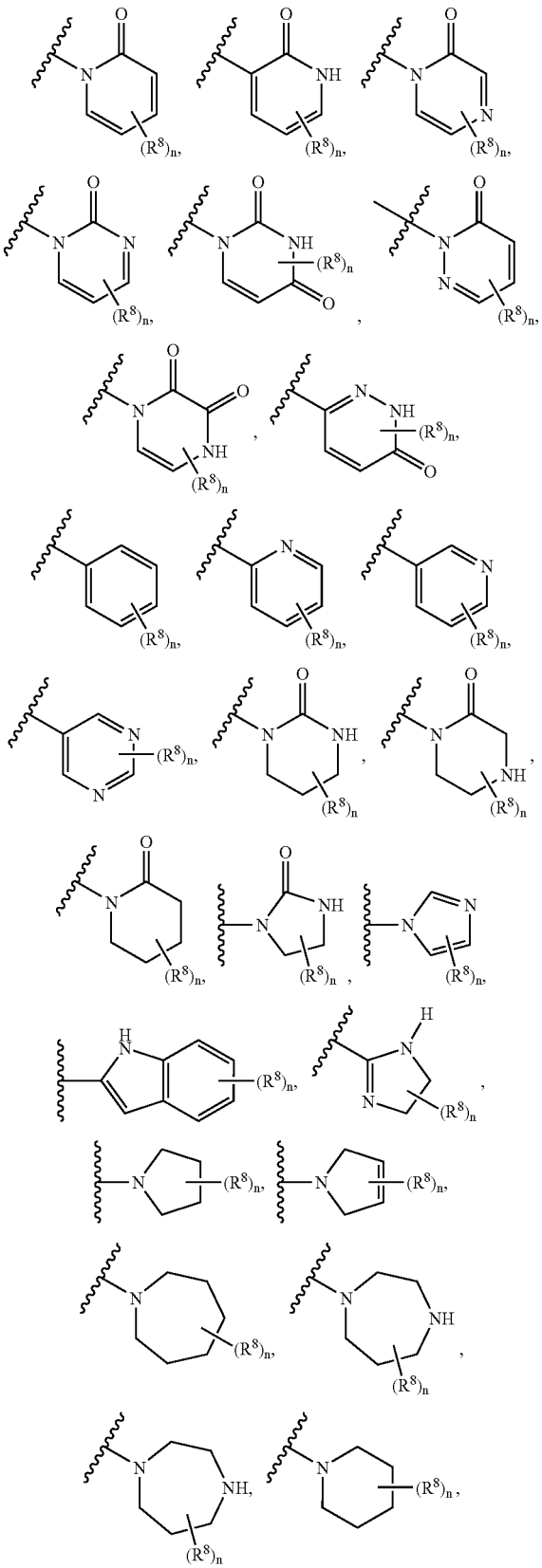

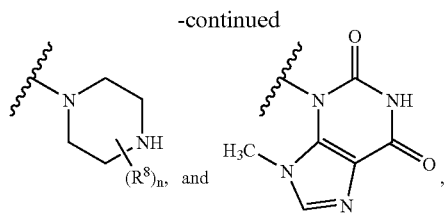

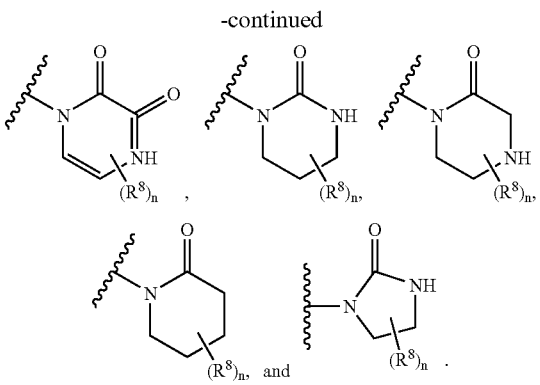

wherein $R^8$ can be at any position suitable for a substituent, and if $R^8$ is attached to a nitrogen atom, then it replaces the hydrogen atom attached thereto;

$R^{7a}$ and $R^{7b}$ are independently selected from the group consisting of hydrogen, $C_{1-8}$ alkyl, and $C_{1-8}$ alkyl substituted with one to three $R^9$;

$R^{7c}$ is selected from the group consisting of aryl, heteroaryl, $C_{1-8}$ alkyl, and $C_{1-8}$ alkyl substituted with one to three $R^9$;

$R^8$ is independently selected from the group consisting of nitro, hydroxyl, —$CO_2H$, —$C(O)R^{8c}$, —$C(O)NR^{8a}R^{8b}$, —$NR^{8a}R^{8b}$, —$SO_2NR^{8a}R^{8b}$, halogen, $C_{1-8}$ alkyl, and $C_{1-8}$ alkoxy wherein said $C_{1-8}$ alkyl and $C_{1-8}$ alkoxy are optionally substituted with one to three $R^9$;

$R^{8a}$ and $R^{8b}$ are independently selected from the group consisting of hydrogen, $C_{1-8}$ alkyl, and $C_{1-8}$ alkyl substituted with one to three $R^9$, or $R^{8a}$ and $R^{8b}$ together form a 5 to 7 membered heterocyclic ring optionally substituted with one to three $R^9$;

$R^{8c}$ is selected from the group consisting of $C_{1-8}$ alkyl and $C_{1-8}$ alkyl substituted with one to three $R^9$;

$R^9$ is independently selected from the group consisting of halogen, 6-membered nitrogen-containing heterocyclic optionally containing an O atom, 5-membered nitrogen-containing heteroaryl, —OH, —$R^{10}$, —$OR^{10}$, —$SR^{10}$, —$S(O)R^{10}$, —$S(O)_2R^{10}$, —$SO_2NH_2$, —$C(O)NH_2$, —$C(O)R^{10}$, —$C(NH)R^{10}$, —$NHC(O)R^{10}$, —$NHC(NH)R^{10}$, —$NHC(O)NH_2$, —$CO_2H$, —$NH_2$, —$NHR^{10}$, —$N(R^{10})_2$ and —$N(R^{10})_3^+$;

each $R^{10}$ is independently $C_{1-6}$ alkyl; and n is 0, 1, 2, or 3.

2. A compound of claim 1, wherein $R^1$ is 2-chloro.

3. A compound of claim 1 wherein $R^2$ is hydrogen.

4. A compound of claim 1 wherein X and Y are CH.

5. A compound of claim 1 wherein $R^3$ is hydrogen.

6. A compound of claim 1 wherein $R^6$ $R^{6a}$.

7. A compound of claim 6 wherein $R^{6a}$ is selected from the group consisting of:

8. A compound of claim 1 wherein $R^6$ is selected from the group consisting of:

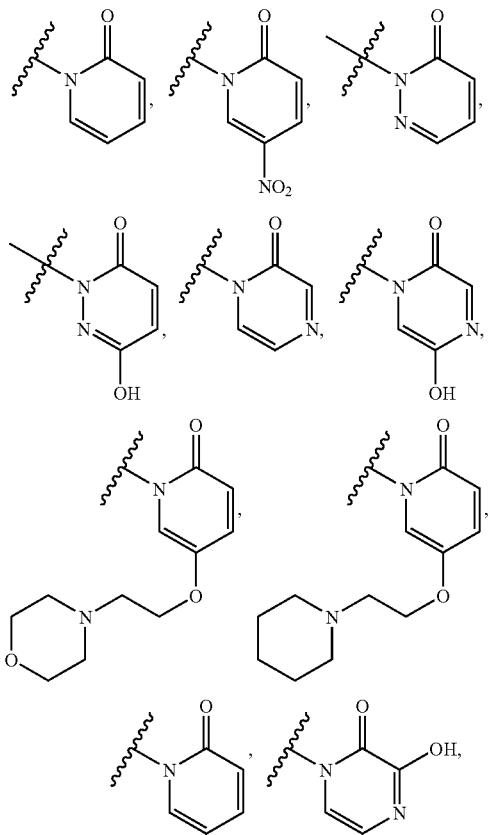

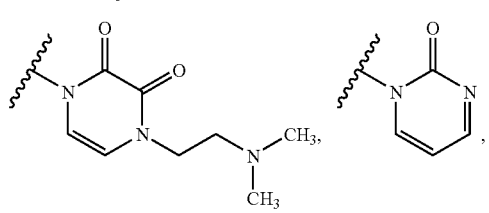

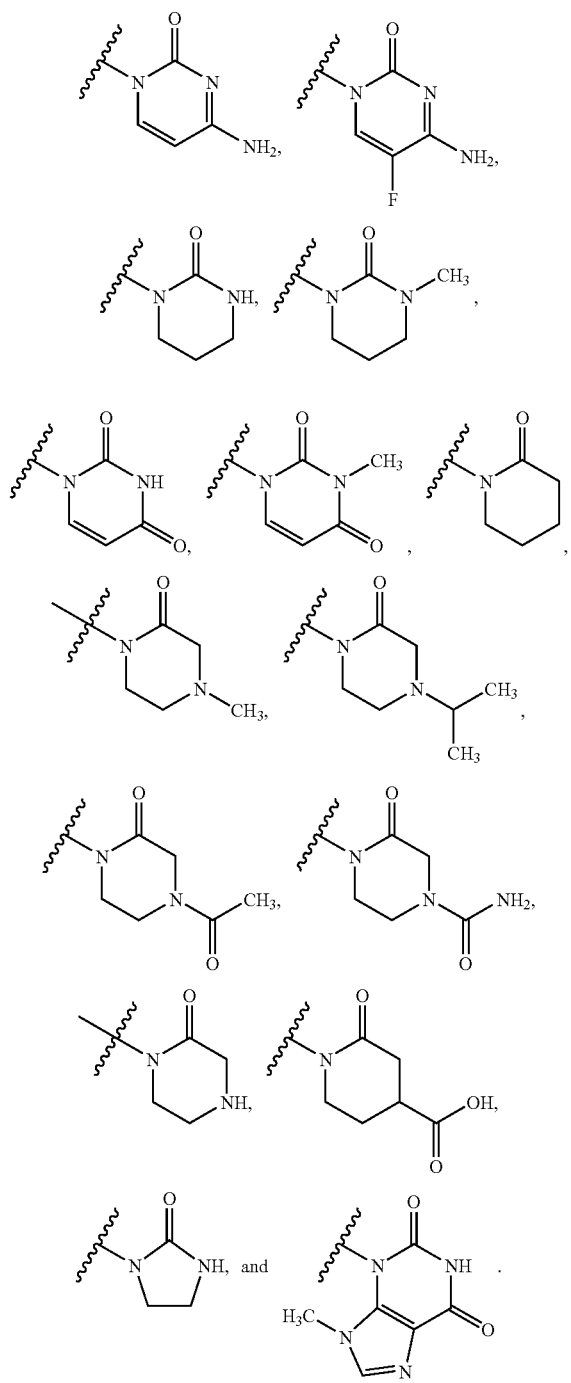
9. A compound of claim 1 wherein $R^6$ is selected from the group consisting of:
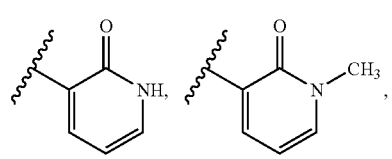
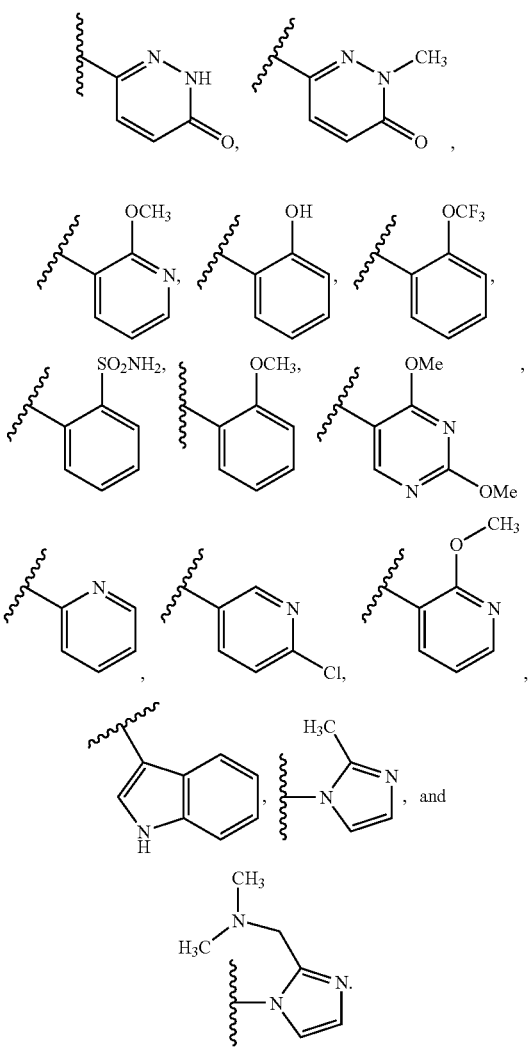
10. A compound of claim 1 wherein $R^6$ is selected from the group consisting of:

-continued

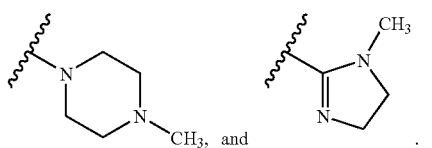

11. A compound of claim 1 wherein $R^6$ is selected from the group consisting of:

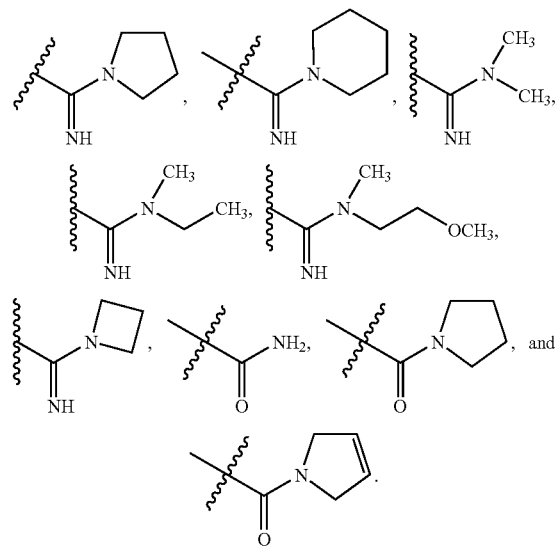

12. A compound of claim 1 wherein $R^6$ is selected from the group consisting of:

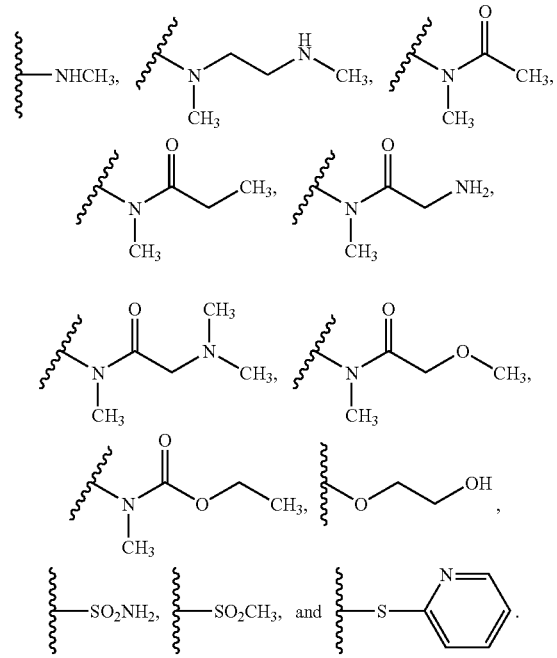

13. A compound of claim 1, wherein $R^6$ is

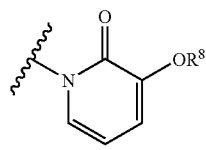

and $R^8$ is as previously defined.

14. A compound of claim 13, wherein $R^8$ is selected from the group consisting of:

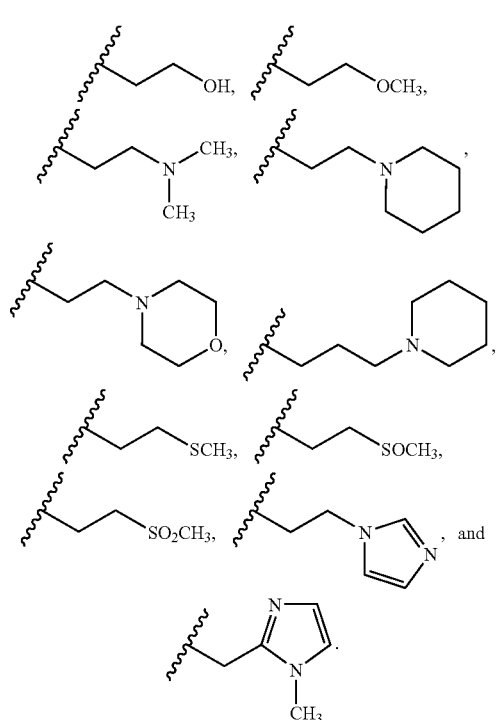

hydrogen.

15. A compound selected from the group consisting of:
- 5-Chloro-N-((1-(4-(2-oxopyridin-1(2H)-yl)-2-(piperazin-1-yl)phenyl)-1H-1,2,3-triazol-4-yl)methyl)thiophene-2-carboxamide,
- 5-Chloro-N-((1-(2-(4-ethylpiperazin-1-yl)-4-(2-oxopyridin-1(2H)-yl)phenyl)-1H-1,2,3-triazol-4-yl)methyl)thiophene-2-carboxamide,
- 5-Chloro-N-((1-(2-(4-isopropylpiperazin-1-yl)-4-(2-oxopyridin-1(2H)-yl)phenyl)-1H-1,2,3-triazol-4-yl)methyl)thiophene-2-carboxamide,
- 5-Chloro-N-((1-(4-(2-oxopyrimidin-1(2H)-yl)phenyl)-1H-1,2,3-triazol-4-yl)methyl)thiophene-2-carboxamide,
- 5-Chloro-N-((1-(4-(1-methyl-6-oxo-1,6-dihydropyridazin-3-yl)phenyl)-1H-1,2,3-triazol-4-yl)methyl)thiophene-2-carboxamide,
- 5-Chloro-N-((1-(4-(2,4-dimethoxypyrimidin-5-yl)phenyl)-1H-1,2,3-triazol-4-yl)methyl)thiophene-2-carboxamide,
- 5-Chloro-N-((1-(4-(2-((dimethylamino)methyl)-1H-imidazol-1-yl)-2-fluorophenyl)-1H-1,2,3-triazol-4-yl)methyl)thiophene-2-carboxamide, 5-Chloro-N-((1-(4-(2-methyl-1H-imidazol-1-yl)phenyl)-1H-1,2,3-triazol-4-yl)methyl)thiophene-2-carboxamide,
5-Chloro-N-((1-(4-(4-methyl-1,4-diazepan-1-yl)phenyl)-1H-1,2,3-triazol-4-yl)methyl)thiophene-2-carboxamide,
5-Chloro-N-((1-(4-(2-oxoimidazolidin-1-yl)phenyl)-1H-1,2,3-triazol-4-yl)methyl)thiophene-2-carboxamide,
5-Chloro-N-((1-(2-methoxybiphenyl-4-yl)-1H-1,2,3-triazol-4-yl)methyl)thiophene-2-carboxamide,
5-Chloro-N-((1-(2'-hydroxybiphenyl-4-yl)-1H-1,2,3-triazol-4-yl)methyl)thiophene-2-carboxamide,
5-Chloro-N-((1-(2'-hydroxybiphenyl-4-yl)-1H-1,2,3-triazol-4-yl)methyl)thiophene-2-carboxamide,
5-Chloro-N-((1-(2'-(trifluoromethoxy)biphenyl-4-yl)-1H-1,2,3-triazol-4-yl)methyl)thiophene-2-carboxamide,
5-Chloro-N-((1-(4-(6-chloropyridin-3-yl)phenyl)-1H-1,2,3-triazol-4-yl)methyl)thiophene-2-carboxamide,
N-((1-(4-(1H-Indol-2-yl)phenyl)-1H-1,2,3-triazol-4-yl)methyl)-5-chlorothiophene-2-carboxamide,
5-Chloro-N-((1-(4-(methylsulfonyl)phenyl)-1H-1,2,3-triazol-4-yl)methyl)thiophene-2-carboxamide,
5-Chloro-N-((1-(3-fluoro-2'-sulfamoylbiphenyl-4-yl)-1H-1,2,3-triazol-4-yl)methyl)thiophene-2-carboxamide,
5-Chloro-N-((1-(4-(pyrrolidine-1-carbonyl)phenyl)-1H-1,2,3-triazol-4-yl)methyl)thiophene-2-carboxamide,
5-Chloro-N-((1-(4-(2,5-dihydro-1H-pyrrole-1-carbonyl)phenyl)-1H-1,2,3-triazol-4-yl)methyl)thiophene-2-carboxamide, N-((1-(4-Carbamoylphenyl)-1H-1-1,2,3-triazol-4-yl)methyl)-5-chlorothiophene-2-carboxamide,
N-((1-(4-(2-Amino-N-methylacetamido)phenyl)-1H-1,2,3-triazol-4-yl)methyl)-5-chlorothiophene-2-carboxamide,
5-Chloro-N-((1-(4-(methyl(2-(methylamino)ethyl)amino)phenyl)-1H-1,2,3-triazol-4-yl)methyl)thiophene-2-carboxamide,
5-Chloro-N-((1-(4-(methylamino)phenyl)-1H-1,2,3-triazol-4-yl)methyl)thiophene-2-carboxamide,
5-Chloro-N-((1-(4-N-methylpropionamido)phenyl)-1H-1,2,3-triazol-4-yl)methyl)thiophene-2-carboxamide,
Ethyl 4-(4-((5-chlorothiophene-2-carboxamido)methyl)-1H-1,2,3-triazol-1-yl)phenyl(methyl)carbamate,
5-Chloro-N-((1-(4-(2-methoxy-N-methylacetamido)phenyl)-1H-1,2,3-triazol-4-yl)methyl)thiophene-2-carboxamide,
5-Chloro-N-((1-(4-(2-(dimethylamino)-N-methylacetamido)phenyl)-1H-1,2,3-triazol-4-yl)methyl)thiophene-2-carboxamide,
5-Chloro-N-((1-(4-(N-methylacetamido)phenyl)-1H-1,2,3-triazol-4-yl)methyl)thiophene-2-carboxamide,
5-Chloro-N-((1-(4-(2-hydroxyethoxy)phenyl)-1H-1,2,3-triazol-4-yl)methyl)thiophene-2-carboxamide,
5-Chloro-N-((1-(4-(6-oxo-1,6-dihydropyridazin-3-yl)phenyl)-1H-1,2,3-triazol-4-yl)methyl)thiophene-2-carboxamide,
5-Chloro-N-((1-(4-(9-methyl-2,6-dioxo-1H-purin-3(2H,6H,9H)-yl)phenyl)-1H-1,2,3-triazol-4-yl)methyl)thiophene-2-carboxamide,
5-Chloro-N-((1-(4-(2-oxopyrazin-1(2H)-yl)phenyl)-1H-1,2,3-triazol-4-yl)methyl)thiophene-2-carboxamide,
5-Chloro-N-((1-(2-fluoro-4-(2-oxopyrazin-1(2H)-yl)phenyl)-1H-1,2,3-triazol-4-yl)methyl)thiophene-2-carboxamide,
5-Chloro-N-((1-(2-fluoro-4-(2-oxopyrimidin-1(2H)-yl)phenyl)-1H-1,2,3-triazol-4-yl)methyl)thiophene-2-carboxamide,
5-Chloro-N-((1-(4-(2-oxotetrahydropyrimidin-1(2H)-yl)phenyl)-1H-1,2,3-triazol-4-yl)methyl)thiophene-2-carboxamide,
5-Chloro-N-((1-(2-fluoro-4-(2-oxo-tetrahydropyrimidin-1(2-H)-yl)phenyl)-1H-1,2,3-triazol-4-yl)methyl)thiophene-2-carboxamide,
5-Chloro-N-((1-(2-fluoro-4-(3-methyl-2-oxo-tetrahydropyrimidin-1(2H)-yl)phenyl)-1H-1,2,3-triazol-4-yl)methyl)thiophene-2-carboxamide,
5-Chloro-N-((1-(2-fluoro-4-(2-oxopiperidin-1-yl)phenyl)-1H-1,2,3-triazol-4-yl)methyl)thiophene-2-carboxamide,
5-Chloro-N-((1-(3-fluoro-4-(2-oxopyridin-1(2H)-yl)phenyl)-1H-1,2,3-triazol-4-yl)methyl)thiophene-2-carboxamide,
5-Chloro-N-((1-(4-(3-hydroxy-2-oxopyridin-1(2H)-yl)phenyl)-1H-1,2,3-triazol-4-yl)methyl)thiophene-2-carboxamide,
5-Chloro-N-((1-(4-(3-(2-hydroxyethoxy)-2-oxopyridin-1(2H)-yl)phenyl)-1H-1,2,3-triazol-4-yl)methyl)thiophene-2-carboxamide,
5-Chloro-N-((1-(4-(3-(2-methoxyethoxy)-2-oxopyridin-1(2H)-yl)phenyl)-1H-1,2,3-triazol-4-yl)methyl)thiophene-2-carboxamide.
5-Chloro-N-((1-(4-(3-(2-(dimethylamino)ethoxy)-2-oxopyridin-1(2H)-yl)phenyl)-1H-1,2,3-triazol-4-yl)methyl)thiophene-2-carboxamide,
5-Chloro-N-((1-(4-(3-(2-(dimethyl(dimethylamino)amino)ethoxy)-2-oxopyridin-1(2H)-yl)phenyl)-1H-1,2,3-triazol-4-yl)methyl)thiophene-2-carboxamide,
5-Chloro-N-((1-(4-(2-oxo-3-(2-(piperidin-1-yl)ethoxy)pyridin-1(2H)-yl)phenyl)-1H-1,2,3-triazol-4-yl)methyl)thiophene-2-carboxamide,
5-Chloro-N-((1-(4-(2-oxo-3-(3-(piperidin-1-yl)propoxy)pyridin-1(2H)-yl)phenyl)-1H-1,2,3-triazol-4-yl)methyl)thiophene-2-carboxamide,
5-Chloro-N-((1-(4-(3-(2-(methylthio)ethoxy)-2-oxopyridin-1(2H)-yl)phenyl)-1H-1,2,3-triazol-4-yl)methyl)thiophene-2-carboxamide,
5-Chloro-N-((1-(4-(3-(2-(methylsulfinyi)ethoxy)-2-oxopyridin-1(2H)-yl)phenyl)-1H-1,2,3-triazol-4-yl)methyl)thiophene-2-carboxamide,
5-Chloro-N-((1-(4-(3-(2-(methylsulfonyl)ethoxy)-2-oxopyridin-1(2H)-yl)phenyl)-1H-1,2,3-triazol-4-yl)methyl)thiophene-2-carboxamide,
5-Chloro-N-((1-(4-(3-(2-morpholinoethoxy)-2-oxopyridin-1(2H)-yl)phenyl)-1H-1,2,3-triazol-4-yl)methyl)thiophene-2-carboxamide,
N-((1-(4-(3-(2-(1H-Imidazol-1-yl)ethoxy)-2-oxopyridin-1(2H)-yl)phenyl)-1H-1,2,3-triazol-4-yl)methyl)-5-chlorothiophene-2-carboxamide,
5-Chloro-N-((1-(4-(3-((1-methyl-1H-imidazol-2-yl)methoxy)-2-oxopyridin-1(2H)-yl)phenyl)-1H-1,2,3-triazol-4-yl)methyl)thiophene-2-carboxamide,
5-Chloro-N-((1-(4-(5-hydroxy-2-oxopyridin-1(2H)-yl)phenyl)-1H-1,2,3-triazol-4-yl)methyl)thiophene-2-carboxamide,
5-Chloro-N-((1-(4-(5-(2-(dimethylamino)ethoxy)-2-oxopyridin-1(2H)-yl)phenyl)-1H-1,2,3-triazol-4-yl)methyl)thiophene-2-carboxamide,
5-Chloro-N-((1-(4-(2-oxo-5-(2-(piperidin-1-yl)ethoxy)pyridin-1(2H)-yl)phenyl)-1H-1,2,3-triazol-4-yl)methyl)thiophene-2-carboxamide, 5-Chloro-N-((1-(4-(5-(2-morpholinoethoxy)-2-oxopyridin-1(2H)-yl)phenyl)-1H-1,2,3-triazol-4-yl)methyl)thiophene-2-carboxamide, 5-Chloro-N-((1-(4-(5-nitro-2-oxopyridin-1(2H)-yl)phenyl)-1H-1,2,3-triazol-4-yl)methyl)thiophene-2-carboxamide, N-((1-(4-(4-Amino-2-oxopyrimidin-1(2H)-yl)phenyl)-1H-1,2,3-triazol-4-yl)methyl)-5-chlorothiophene-2-carboxamide, 5-Chloro-N-((1-(4-(2,4-dioxo-3,4-dihydropyrimidin-1(2H)-yl)phenyl)-1H-1,2,3-triazol-4-yl)methyl)thiophene-2-carboxamide, N-((1-(4-(4-Amino-5-fluoro-2-oxopyrimidin-1(2H)-yl)phenyl)-1H-1,2,3-triazol-4-yl)methyl)-5-chlorothiophene-2-carboxamide, 5-Chloro-N-((1-(4-(3-methyl-2,4-dioxo-3,4-dihydropyrimidin-1(2H)-yl)phenyl)-1H-1,2,3-triazol-4-yl)methyl)thiophene-2-carboxamide, 5-Chloro-N-((1-(4-(2-oxopiperazin-1-yl)phenyl)-1H-1,2,3-triazol-4-yl)methyl)thiophene-2-carboxamide, 5-Chloro-N-((1-(4-(4-methyl-2-oxopiperazin-1-yl)phenyl)-1H-1,2,3-triazol-4-yl)methyl)thiophene-2-carboxamide, 5-Chloro-N-((1-(4-(4-isopropyl-2-oxopiperazin-1-yl)phenyl)-1H-1,2,3-triazol-4-yl)methyl)thiophene-2-carboxamide, 4-(4-(4-((5-Chlorothiophene-2-carboxamido)methyl)-1H-1,2,3-triazol-1-yl)phenyl)-3-oxopiperazine-1-carboxamide, 5-Chloro-N-((1-(4-(3-hydroxy-2-oxopyrazin-1(2H)-yl)phenyl)-1H-1,2,3-triazol-4-yl)methyl)thiophene-2-carboxamide, 5-Chloro-N-((1-(4-(4-(2-(dimethylamino)ethyl)-2,3-dioxo-3,4-dihydropyrazin-1(2H)-yl)phenyl)-1H-1,2,3-triazol-4-yl)methyl)thiophene-2-carboxamide, 5-Chloro-N-((1-(4-(3-hydroxy-6-oxopyridazin-1(6H)-yl)phenyl)-1H-1,2,3-triazol-4-yl)methyl)thiophene-2-carboxamide, 2-((1-(4-(2-Oxopyridin-1(2H)-yl)phenyl)-1H-1,2,3-triazol-4-yl)methylcarbamoyl)benzoic acid, N-((1-(2-(3-Oxopiperazin-1-yl)-4-(2-oxopyridin-1(2H)-yl)phenyl)-1H-1,2,3-triazol-4-yl)methyl)thiophene-2-carboxamide, 5-Chloro-N-((1-(4-(1-methyl-4,5-dihydro-1H-imidazol-2-yl)phenyl)-1H-1,2,3-triazol-5-yl)methyl)thiophene-2-carboxamide, 5-Chloro-N-((1-(4-(N,N-dimethylcarbamimidoyl)phenyl)-1H-1,2,3-triazol-5-yl)methyl)thiophene-2-carboxamide, 5-Chloro-N-((1-(4-(imino(pyrrolidin-1-yl)methyl)phenyl)-1H-1,2,3-triazol-5-yl)methyl)thiophene-2-carboxamide, 5-Chloro-N-((1-(4-(imino(piperidin-1-yl)methyl)phenyl)-1H-1,2,3-triazol-5-yl)methyl)thiophene-2-carboxamide, N-((1-(4-Carbarnoylphenyl)-1H-1,2,3-triazol-5-yl)methyl)-5-chlorothiophene-2-carboxamide, 5-Chloro-N-((1-(4-(methylsulfonyl)phenyl)-1H-1,2,3-triazol-5-yl)methyl)thiophene-2-carboxamide, 5-Chloro-N-((1-(4-(2-oxopyridin-1(2H)-yl)phenyl)-1H-1,2,3-triazol-5-yl)methyl)thiophene-2-carboxamide, 5-Chloro-N-((1-(4-(pyridin-2-ylthio)phenyl)-1H-1,2,3-triazol-5-yl)methyl)thiophene-2-carboxamide, 5-Chloro-N-((1-(6-(pyrrolidin-1-yl)pyridin-3-yl)-1H-1,2,3-triazol-4-yl)methyl)thiophene-2-carboxamide, 1-(5-(4-((5-Chlorothiophene-2-carboxamido)methyl)-1H-1,2,3-triazol-1-yl)pyridin-2-yl)piperidine-4-carboxylic acid, N-((1-(6-(Azepan-1-yl)pyridin-3-yl)-1H-1,2,3-triazol-4-yl)methyl)-5-chlorothiophene-2-carboxamide, 5-Chloro-N-((1-(6-(4-methyl-1,4-diazepan-1-yl)pyridin-3-yl)-1H-1,2,3-triazol-5-yl)methyl)thiophene-2-carboxamide, N-((1(6-(1,4-Diazepan-1-yl)pyridin-3-yl)-1H-1,2,3-triazol-5-yl)methyl)-5-chlorothiophene-2-carboxamide, 5-Chloro-N-((1-(6-(4-methylpiperazin-1-yl)pyridin-3-yl)-1H-1,2,3-triazol-5-yl)methyl)thiophene-2-carboxamide, 5-Chloro-N-((1-(6-(piperazin-1-yl)pyridin-3-yl)-1H-1,2,3-triazol-5-yl)methyl)thiophene-2-carboxamide, 5-Chloro-N-((1-(3-(2-oxopyridin-1(2H)-yl)phenyl)-1H-1,2,3-triazol-4-yl)methyl)thiophene-2-carboxamide, 5-Chloro-N-((1-(4-methyl-3-oxo-3,4-dihydro-2H-benzo[β][1,4]oxazin-7-yl)-1H-1,2,3-triazol-4-yl)methyl)thiophene-2-carboxamide, 5-Chloro-N-((1-(3-methoxy-4-(2-oxopyridin-1(2H)-yl)phenyl)-1H-1,2,3-triazol-4-yl)methyl)thiophene-2-carboxamide, and 5-Chloro-N-((1-(5-(2-oxopyridin-1(2H)-yl)quinolin-8-yl)-1H-1,2,3-triazol-4-yl)methyl)thiophene-2-carboxamide, or a pharmaceutically acceptable salt, ester thereof.

16. A composition comprising a pharmaceutically acceptable excipient and a compound of claim 1 or 15.

* * * * *

UNITED STATES PATENT AND TRADEMARK OFFICE
CERTIFICATE OF CORRECTION

PATENT NO. : 7,696,352 B2  Page 1 of 2
APPLICATION NO. : 11/620615
DATED : April 13, 2010
INVENTOR(S) : Bing-Yan Zhu et al.

It is certified that error appears in the above-identified patent and that said Letters Patent is hereby corrected as shown below:

IN THE CLAIMS

In Column 135, Claim 6, Line 49, please replace "$R^6$ $R^{6a}$" with -- $R^6$ is $R^{6a}$ --.

In Column 136, Claim 7, Line 5, please replace " 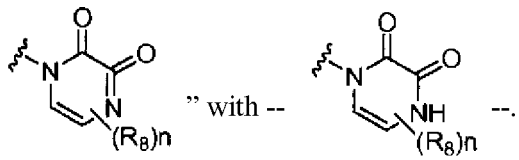 --.

In Column 140, Claim 14, Line 15, please replace " 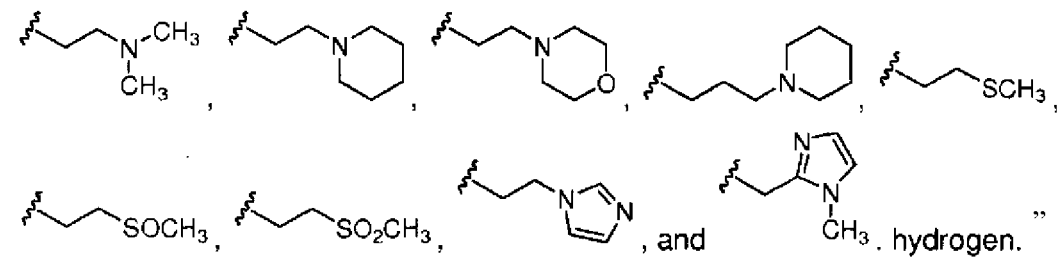

with -- 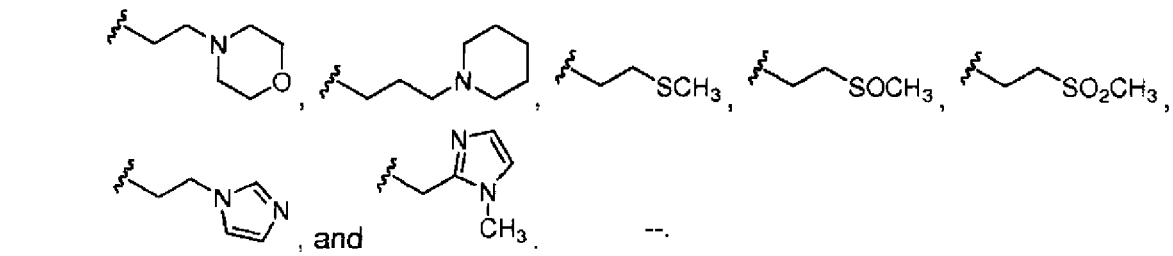

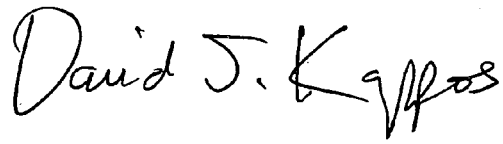 --.

Signed and Sealed this

Nineteenth Day of October, 2010

David J. Kappos
*Director of the United States Patent and Trademark Office*

CERTIFICATE OF CORRECTION (continued)
U.S. Pat. No. 7,696,352 B2

In Column 141, Claim 15, Line 9, please replace "2-methoxybiphenyl-4-yl" with
-- 2'-methoxybiphenyl-4-yl --.

In Column 141, Claim 15, Line 30, please replace
"boxamide,   N-((1-(4-Carbamoylphenyl)-1H-1-1,2,3-" with
-- boxamide,
N-((1-(4-Carbamoylphenyl)-1H-1,2,3- --.

In Column 141, Claim 15, Line 42, please replace "((1-(4-N-methylpropionamido)phenyl)"
with -- ((1-(4-(N-methylpropionamido)phenyl) --.

In Column 142, Claim 15, Line 8, please replace "1(2-H)-yl)phenyl" with
-- 1(2H)-yl)phenyl --.

In Column 142, Claim 15, Line 43, please replace "methylsulfinyi" with -- methylsulfinyl --.

In Column 144, Claim 15, Line 2, please replace "1H-1    ,2,3-triazol-5-yl)methyl" with
-- 1H-1,2,3-triazol-5-yl)methyl --.

In Column 144, Claim 15, Line 7, please replace "4-Carbarnoylphenyl" with
-- 4-Carbamoylphenyl --.